(12) United States Patent
Merriman et al.

(10) Patent No.: US 11,624,725 B2
(45) Date of Patent: *Apr. 11, 2023

(54) METHODS AND APPARATUS FOR MEASURING ANALYTES USING POLYMERASE IN LARGE SCALE MOLECULAR ELECTRONICS SENSOR ARRAYS

(71) Applicant: Roswell Biotechnologies, Inc., San Diego, CA (US)

(72) Inventors: Barry L. Merriman, San Diego, CA (US); Paul W. Mola, San Diego, CA (US); Chulmin Choi, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/073,693

(22) PCT Filed: Jan. 27, 2017

(86) PCT No.: PCT/US2017/015465
§ 371 (c)(1),
(2) Date: Jul. 27, 2018

(87) PCT Pub. No.: WO2017/132586
PCT Pub. Date: Aug. 3, 2017

(65) Prior Publication Data
US 2019/0041355 A1 Feb. 7, 2019

Related U.S. Application Data

(60) Provisional application No. 62/288,360, filed on Jan. 28, 2016.

(51) Int. Cl.
*G01N 27/41* (2006.01)
*H01L 21/764* (2006.01)
(Continued)

(52) U.S. Cl.
CPC .......... *G01N 27/4145* (2013.01); *B82Y 15/00* (2013.01); *G01N 27/4146* (2013.01);
(Continued)

(58) Field of Classification Search
CPC ...... B82Y 15/00; B82Y 40/00; C12Q 1/6825; C12Q 1/6869; G01N 27/26; G01N 27/327;
(Continued)

(56) References Cited

U.S. PATENT DOCUMENTS 4,923,586 A 5/1990 Katayama et al.
5,082,627 A 1/1992 Stanbro
(Continued)

FOREIGN PATENT DOCUMENTS

CN 1795376 6/2006
CN 101231287 7/2008
(Continued)

OTHER PUBLICATIONS

Strobel, S. et al., Nanotechnology 2007, 18, paper 295201, 5 pages.*
(Continued)

*Primary Examiner* — Arlen Soderquist
(74) *Attorney, Agent, or Firm* — Spectrum IP Law Group LLC

(57) ABSTRACT

In various embodiments of the present disclosure, a molecular electronics sensor array chip comprises: (a) an integrated circuit semiconductor chip; and (b) a plurality of molecular electronic sensor devices disposed thereon, each of said sensor devices comprising: (i) a pair of nanoscale source and drain electrodes separated by a nanogap; (ii) a gate elec-
(Continued)

trode; and (iii) a bridge and/or probe molecule spanning the nanogap and connecting the source and drain electrodes, wherein the molecular electronic sensor devices are organized into an electronically addressable, controllable, and readable array of sensor pixels.

25 Claims, 85 Drawing Sheets

(51) Int. Cl.
  *B82Y 15/00* (2011.01)
  *H01L 29/10* (2006.01)
  *H01L 29/41* (2006.01)
  *G01N 27/414* (2006.01)
  *H01L 29/417* (2006.01)
  *H01L 51/05* (2006.01)
  *H01L 51/00* (2006.01)
  *C12Q 1/6869* (2018.01)

(52) U.S. Cl.
  CPC ........ *H01L 21/764* (2013.01); *H01L 29/1033* (2013.01); *H01L 29/41725* (2013.01); *C12Q 1/6869* (2013.01); *G01N 27/4148* (2013.01); *H01L 51/0093* (2013.01); *H01L 51/0558* (2013.01)

(58) Field of Classification Search
  CPC ........... G01N 27/3272; G01N 27/3276; G01N 27/3278; G01N 27/4145; G01N 27/4146; G01N 27/4148; G01N 33/48721; G01N 33/5438; H01L 21/764; H01L 29/1033; H01L 29/41725; H01L 51/0093; H01L 51/0558; H01M 4/02; H01M 4/92; H01M 4/94; Y02E 60/10; Y02E 60/50
  USPC ................ 422/82.01–82.4, 98; 436/149–150
  See application file for complete search history.

(56) References Cited

U.S. PATENT DOCUMENTS

| | | | |
|---|---|---|---|
| 5,194,133 A | 3/1993 | Clark et al. | |
| 5,366,140 A | 11/1994 | Koskenmaki et al. | |
| 5,414,588 A | 5/1995 | Barbee, Jr. | |
| 5,486,449 A | 1/1996 | Honso et al. | |
| 5,532,128 A | 7/1996 | Eggers et al. | |
| 5,583,359 A | 12/1996 | Ng et al. | |
| 5,639,507 A | 6/1997 | Galvagni et al. | |
| 5,646,420 A | 7/1997 | Yamashita | |
| 5,767,687 A | 6/1998 | Geist | |
| 5,871,918 A | 2/1999 | Thorp et al. | |
| 5,881,184 A | 3/1999 | Guidash | |
| 5,955,379 A * | 9/1999 | Lennox | G01N 33/5438 435/7.1 |
| 5,965,452 A * | 10/1999 | Kovacs | B01J 19/0046 204/412 |
| 5,982,018 A | 11/1999 | Wark | |
| 6,051,380 A | 4/2000 | Sosnowski et al. | |
| 6,060,023 A | 5/2000 | Maracas | |
| 6,094,335 A | 7/2000 | Early | |
| 6,107,080 A * | 8/2000 | Lennox | C12Q 1/003 436/806 |
| 6,110,354 A | 8/2000 | Saban | |
| 6,123,819 A | 9/2000 | Peeters | |
| 6,130,037 A * | 10/2000 | Lennox | G01N 33/54373 435/7.37 |
| 6,144,023 A | 11/2000 | Clerc | |
| 6,165,335 A * | 12/2000 | Lennox | C12Q 1/003 436/908 |
| 6,238,927 B1 | 5/2001 | Abrams et al. | |
| 6,300,141 B1 * | 10/2001 | Segal | G01N 33/5438 204/422 |
| 6,440,662 B1 | 8/2002 | Gerwen et al. | |
| 6,464,889 B1 | 10/2002 | Lee et al. | |
| 6,506,564 B1 | 1/2003 | Mirkin et al. | |
| 6,537,747 B1 | 3/2003 | Mills, Jr. et al. | |
| 6,670,131 B2 | 12/2003 | Hashimoto | |
| 6,673,533 B1 | 1/2004 | Wohlstadter et al. | |
| 6,716,620 B2 | 4/2004 | Bashir et al. | |
| 6,749,731 B2 | 6/2004 | Kobori | |
| 6,762,050 B2 | 7/2004 | Fukushima et al. | |
| 6,764,745 B1 | 7/2004 | Karasawa et al. | |
| 6,790,341 B1 | 9/2004 | Saban | |
| 6,824,974 B2 | 11/2004 | Pisharody et al. | |
| 6,861,224 B2 | 3/2005 | Fujita et al. | |
| 6,916,614 B1 | 7/2005 | Takenaka et al. | |
| 6,958,216 B2 | 10/2005 | Kelley | |
| 7,015,046 B2 | 3/2006 | Wohlstadter et al. | |
| 7,075,428 B1 | 7/2006 | Oleynik | |
| 7,169,272 B2 | 1/2007 | Fritsch et al. | |
| 7,183,055 B2 | 2/2007 | Van Der Weide | |
| 7,189,435 B2 | 3/2007 | Tuominen et al. | |
| 7,202,480 B2 | 4/2007 | Yokoi et al. | |
| 7,208,077 B1 | 4/2007 | Albers et al. | |
| 7,276,206 B2 | 10/2007 | Augustine et al. | |
| 7,399,585 B2 | 7/2008 | Gau | |
| 7,432,120 B2 | 10/2008 | Mascolo et al. | |
| 7,470,533 B2 | 12/2008 | Xu et al. | |
| 7,507,320 B2 | 3/2009 | Hwang et al. | |
| 7,531,120 B2 | 5/2009 | Van Rijn et al. | |
| 7,579,823 B1 | 8/2009 | Ayliffe | |
| 7,691,433 B2 | 4/2010 | Kronholz et al. | |
| 7,785,785 B2 | 8/2010 | Pourmand et al. | |
| 7,834,344 B2 | 11/2010 | Mascolo et al. | |
| 7,851,045 B2 | 12/2010 | Gandon et al. | |
| 7,886,601 B2 | 2/2011 | Merassi et al. | |
| 7,901,629 B2 | 3/2011 | Calatzis et al. | |
| 7,943,394 B2 | 5/2011 | Flandre et al. | |
| 8,241,508 B2 | 8/2012 | D'Urso | |
| 8,313,633 B2 | 11/2012 | Li et al. | |
| 8,351,181 B1 | 1/2013 | Ahn | |
| 8,591,816 B2 | 11/2013 | Calatzis et al. | |
| 8,652,768 B1 | 2/2014 | Huber et al. | |
| 8,753,893 B2 | 6/2014 | Liu et al. | |
| 8,927,464 B2 | 1/2015 | Aizenberg et al. | |
| 8,940,663 B2 | 1/2015 | Iqbal et al. | |
| 9,070,733 B2 | 6/2015 | Rajagopal et al. | |
| 9,108,880 B2 | 8/2015 | Jin et al. | |
| 9,139,614 B2 | 9/2015 | Medintz | |
| 9,306,164 B1 | 4/2016 | Chang et al. | |
| 9,829,456 B1 | 11/2017 | Merriman et al. | |
| 9,956,743 B2 | 5/2018 | Jin et al. | |
| 10,036,064 B2 | 7/2018 | Merriman et al. | |
| 10,125,420 B2 | 11/2018 | Jin et al. | |
| 10,151,722 B2 | 12/2018 | Jin et al. | |
| 10,508,296 B2 | 12/2019 | Merriman et al. | |
| 10,526,696 B2 | 1/2020 | Jin et al. | |
| 10,584,410 B2 | 3/2020 | Jin et al. | |
| 10,597,767 B2 | 3/2020 | Merriman et al. | |
| 10,712,334 B2 | 7/2020 | Choi et al. | |
| 2002/0016306 A1 * | 2/2002 | Hutchison | B82Y 10/00 514/44 R |
| 2002/0022223 A1 | 2/2002 | Connolly | |
| 2002/0090649 A1 | 7/2002 | Chan et al. | |
| 2002/0098500 A1 * | 7/2002 | Saraf | H01L 51/0595 435/6.11 |
| 2002/0119572 A1 * | 8/2002 | Jacobson | C12N 13/00 435/466 |
| 2002/0137083 A1 | 9/2002 | Kobori et al. | |
| 2002/0138049 A1 | 9/2002 | Allen et al. | |
| 2002/0142150 A1 | 10/2002 | Baumann et al. | |
| 2002/0142477 A1 | 10/2002 | Lewis et al. | |
| 2002/0146742 A1 * | 10/2002 | Wybourne | C07H 21/00 435/7.1 |
| 2002/0168667 A1 * | 11/2002 | Kinoshita | G01N 33/54366 435/6.11 |
| 2002/0172963 A1 | 11/2002 | Kelley et al. | |
| 2002/0184939 A1 | 12/2002 | Yadav | |
| 2003/0025133 A1 | 2/2003 | Brousseau | |
| 2003/0040000 A1 | 2/2003 | Connolly et al. | |

(56) References Cited

U.S. PATENT DOCUMENTS

| | | |
|---|---|---|
| 2003/0040173 A1* | 2/2003 | Fonash ............... F16K 99/0003 438/622 |
| 2003/0064390 A1 | 4/2003 | Schülein et al. |
| 2003/0077625 A1* | 4/2003 | Hutchison ............ C07H 21/00 435/7.1 |
| 2003/0087296 A1 | 5/2003 | Fujita et al. |
| 2003/0109031 A1* | 6/2003 | Chafin ................ C12Q 1/6834 506/3 |
| 2003/0141189 A1* | 7/2003 | Lee ..................... C12Q 1/6869 204/600 |
| 2003/0141276 A1* | 7/2003 | Lee ....................... B82Y 10/00 216/8 |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1* | 3/2004 | Freeman ............. G01N 33/5438 435/5 |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0166673 A1* | 8/2004 | Hutchison ............ B82Y 30/00 438/686 |
| 2004/0209355 A1 | 10/2004 | Edman et al. |
| 2004/0209435 A1 | 10/2004 | Patridge et al. |
| 2004/0229247 A1* | 11/2004 | DeBoer ............... B01J 19/0046 435/6.12 |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Komilovich et al. |
| 2005/0151541 A1 | 7/2005 | Brinz et al. |
| 2005/0156157 A1* | 7/2005 | Parsons ................ G11C 13/02 257/20 |
| 2005/0164371 A1* | 7/2005 | Arinaga .............. G01N 27/3278 435/287.1 |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0081835 A1* | 4/2006 | Hutchison ............ B82Y 10/00 257/17 |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1* | 8/2007 | Curry ..................... G01Q 70/12 73/105 |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1* | 1/2008 | Li ...................... G01N 27/4145 257/40 |
| 2008/0098815 A1 | 5/2008 | Merassi et al. |
| 2008/0149479 A1* | 6/2008 | Olofsson ............... B82Y 30/00 204/403.14 |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0305432 A1* | 12/2009 | Liotta ................ G01N 33/54373 436/501 |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0101956 A1* | 4/2010 | Choi ..................... C12Q 1/6825 204/547 |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0201381 A1* | 8/2010 | Iqbal .................... C12Q 1/6825 324/663 |
| 2010/0206367 A1 | 8/2010 | Jeong et al. |
| 2010/0227416 A1* | 9/2010 | Koh ..................... C12Q 1/6837 436/501 |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci et al. |
| 2011/0065588 A1* | 3/2011 | Su ........................ C12Q 1/6874 506/2 |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0224091 A1* | 9/2011 | Panchapakesan ...... B82Y 15/00 506/9 |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1* | 5/2012 | Gao ..................... G01N 33/5438 506/9 |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1* | 12/2012 | Eichen ................. C12Q 1/6816 436/501 |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |

(56) References Cited

U.S. PATENT DOCUMENTS

| | | |
|---|---|---|
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0027775 A1 | 1/2014 | Quick et al. |
| 2014/0048776 A1 | 2/2014 | Huang et al. |
| 2014/0054788 A1* | 2/2014 | Majima ............ H01L 21/76838 |
| | | 257/773 |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1* | 10/2014 | Chou ...................... B03C 5/026 |
| | | 356/72 |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0006089 A1* | 1/2015 | Pagels ............. G01N 33/54386 |
| | | 702/19 |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0065353 A1* | 3/2015 | Turner ............... G01N 27/3278 |
| | | 506/2 |
| 2015/0068892 A1 | 3/2015 | Ueno et al. |
| 2015/0077183 A1 | 3/2015 | Ciubotaru |
| 2015/0132835 A1* | 5/2015 | Pagels ............. G01N 33/48792 |
| | | 435/287.2 |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0268186 A1* | 9/2015 | Pagels .................... G16H 10/40 |
| | | 205/792 |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0290957 A1* | 10/2016 | Ram ..................... C12Q 1/6825 |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0038333 A1* | 2/2017 | Turner .................... G11C 19/28 |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1* | 10/2017 | Majima ................... G06N 10/00 |
| 2017/0332918 A1 | 11/2017 | Keane |
| 2018/0014786 A1 | 1/2018 | Keane |
| 2018/0030601 A1* | 2/2018 | Naaman ............... H01G 9/2031 |
| 2018/0031508 A1 | 2/2018 | Jin |
| 2018/0031509 A1 | 2/2018 | Jin |
| 2018/0038815 A1* | 2/2018 | Gu .................. G01N 33/56916 |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |
| 2020/0242482 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |

FOREIGN PATENT DOCUMENTS

| | | |
|---|---|---|
| CN | 102706940 | 10/2012 |
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2008258594 A | 10/2008 |
| JP | 2018-522236 | 8/2018 |
| KR | 20070059880 | 6/2007 |
| KR | 20110104245 | 9/2011 |
| WO | 2002049980 | 6/2002 |
| WO | 2001044501 A3 | 7/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 A1 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |

(56) References Cited

FOREIGN PATENT DOCUMENTS

| WO | 2018136148 | 7/2018 |
|---|---|---|
| WO | 2018200687 | 11/2018 |
| WO | 2018208505 | 11/2018 |
| WO | 2003091458 | 1/2019 |

OTHER PUBLICATIONS

Xu, B. et al, Journal of the American Chemical Society 2003, 125, 16164-16165.*
Xioa, X. et al, Journal of the American Chemical Society 2004, 126, 5370-5371.*
Sek, S. et al., Journal of Physical Chemistry B 2005, 109, 23121-23124.*
Kitagawa, K. et al, Thin Solid Films 2009, 509, 18-26.*
Yeh, J. I. et al, Biosensors and Bioelectronics 2007, 23, 568-574.*
Kim, S. K. et al, Nanotechnology 2009, 20, paper 455502, 7 pages.*
Shinwari, M. et al, Advanced Functional Materials 2010, 20, 1865-1883.*
Scullion, L. et al, Journal of Physical Chemistry C 2011, 115, 8361-8368.*
USPTO; Final Office Action dated Mar. 6, 2020 in U.S. Appl. No. 16/011,065.
USPTO; Notice of Allowance dated Feb. 20, 2020 in U.S. Appl. No. 16/015,049.
USPTO; Non-Final Office Action dated Apr. 13, 2020 in Application No. 16/070,133.
USPTO; Restriction Requirement dated Apr. 8, 2020 in U.S. Appl. No. 16/479,257.
EP; European Search Report dated Jan. 29, 2020 in Application No. 17745013.7.
EP; European Search Report dated Jan. 29, 2020 in Application No. 17750776.1.
EP; European Search Report dated Feb. 7, 2020 in Application No. 17837566.3.
EP; European Search Report dated Mar. 6, 2020 in Application No. 17835231.6.
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Guo et al., "Conductivity of a single DNA duplex bridging a carbon nanotube gap," Nat. Nanotechnol., vol. 3, No. 3, pp. 1-12 (2008).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Pugliese et al., "Processive Incorporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Zafarani et al., "Electrochemical Redox Cycling in a New Nanogap Sensor: Design and Simulation," Journal of Electroanalytical Chemistry, vol. 760, pp. 42-47, (2015).
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
CN; Notice of the First Office Action dated Sep. 2, 2019 in Chinese Application No. 201680049272.8.
EP; European Search Report dated Aug. 2, 2019 in Application No. EP16885434.7.
EP; European Search Report dated Aug. 2, 2019 in Application No. EP17745026.9.
USPTO; Non-Final Office Action dated Feb. 26, 2019 in U.S. Appl. No. 15/050,270.
USPTO; Final Office Action dated Mar. 1, 2019 in U.S. Appl. No. 15/979,135.
USPTO; Non-Final Office Action dated Mar. 6, 2019 in U.S. Appl. No. 16/015,049.
USPTO; Non-Final Office Action dated Mar. 7, 2019 in U.S. Appl. No. 15/944,356.
USPTO; Final Office Action dated Apr. 15, 2019 in U.S. Appl. No. 16/015,028.
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of Am Chem Soc, vol. 129, pp. 1959-1967, (2007).
Khawli et al., "Charge Variants in IgG1-Isolation, Characterization, In Vitro Binding Properties and Pharmacokinetics in Rats," Landes Bioscience, pp. 613-623, (2010).
Schaefer et al., "Stability and Dewetting Kinetics of Thin Gold Films on Ti, TiOx, and ZnO Adhesion Layers," Acta Materialia, vol. 61, pp. 7841-7848, (2013).
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report dated Nov. 9, 2018 in Application No. PCT/US2018/048873.
PCT; Written Opinion dated Nov. 9, 2018 in Application No. PCT/US2018/048873.
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Van Gerwin et al., "Nanoscaled Interdigitated Electrode Arrays for Biochemical Sensors," Sensors and Actuators B, vol. 49, pp. 73-80, (1998).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Javey et al., "Layer-By-Layer Assembly of Nanowires for Three-Dimensional, Multifunctional Electronics," Nano Letters, vol. 7, pp. 773-777, (2007).
Fan et al., "Detection of MicroRNAs Using Target-Guided Formation of Conducting Polymer Nanowires in Nanogaps," Journal of the American Chemical Society, vol. 129, pp. 5437-5443, (2007).
Kitsara et al., "Single Chip Interdigitated Electrode Capacitive Chemical Sensor Arrays," Sensors and Actuators B, vol. 127, pp. 186-192, (2007).
Xu et al., "Fabrication of Complex Metallic Nanostructures by Nanoskiving," American Chemical Society Nano, vol. 1(3), pp. 215-227, (2007).
Berdat et al., "Label-Free Detection of DNA with Interdigitated Micro-Electrodes in a Fluidic Cell," Lab on a Chip, vol. 8, pp. 302-308, (2008).

(56) References Cited

OTHER PUBLICATIONS

Dickey et al., "Electrically Addressable Parallel Nanowires with 30 NM Spacing from Micromolding and Nanoskiving," Nano Letters, vol. 8(12), pp. 4568-4573, (2008).
Singh et al., "3D Nanogap Interdigitated Electrode Array Biosensors," Analytical and Bioanalytical Chemistry, vol. 397, pp. 1493-1502, (2010).
Bhura, "3D Interdigitated Electrode Array (IDEA) Biosensor for Detection of Serum Biomarker," Master Thesis, Portland State University, 68 Pages, (2011).
Ino et al., "Addressable Electrode Array Device with IDA Electrodes for High-Throughput Detection," Lab on a Chip, vol. 11, p. 385-388, (2011).
Bonilla et al., "Electrical Readout of Protein Microarrays on Regular Glass Slides," Analytical Chemistry, vol. 83, pp. 1726-1731, (2011).
Ahn et al., "Electrical Immunosensor Based on a Submicron-Gap Interdigitated Electrode and Gold Enhancement," Biosensors and Bioelectronics, vol. 26, pp. 4690-4696, (2011).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Chen et al., "Fabrication of Submicron-Gap Electrodes by Silicon Volume Expansion for DNA-Detection," Sensors and Actuators A, vol. 175, pp. 73-77, (2012).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Botsialas et al., "A Miniaturized Chemocapacitor System for the Detection of Volatile Organic Compounds," Sensors and Actuators B, Chemical, vol. 177, pp. 776-784, (2013).
Sanguino et al., "Interdigitated Capacitive Immunosensors with PVDF Immobilization Layers," IEEE Sensors Journal, vol. 14(4), pp. 1260-1265, (Apr. 2014).
Van Megan et al., "Submicron Electrode Gaps Fabricated by Gold Electrodeposition at Interdigitated Electrodes," Key Engineering Materials, vol. 605, pp. 107-110, (2014).
MacNaughton et al., "High-Throughput Heterogeneous Integration of Diverse Nanomaterials on a Single Chip for Sensing Applications," PLOS One, vol. 9(10), e111377, 7 Pages, (2014).
Kitsara et al., "Small-Volume Multiparametric Electrochemical Detection at Low Cost Polymeric Devices Featuring Nanoelectrodes," SPIE, vol. 9518, 9 Pages, (2015).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Han et al., "Redox Cycling in Nanopore-Confined Recessed Dual-Ring Electrode Arrays," Journal of Physical Chemistry C, vol. 120, pp. 20634-20641, (2016).
Okinaka et al., ""Polymer" Inclusions in Cobalt-Hardened Electroplated Gold," Journal the of Electrochemical Society, vol. 125, p. 1745, (1978).
Braun et al., "DNA-Templated Assembly and Electrode Attachment of a Conducting Silver Wire," Letters to Nature, vol. 391(6669), pp. 775-778, (Feb. 1998).
Chen et al., "Electrochemical Approach for Fabricating Nanogap Electrodes with Well Controllable Separation," Applied Physics Letters, vol. 86, pp. 123105.1-123105.3, (2005).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Iqbal et al., "Direct Current Electrical Characterization of ds-DNA in Nanogap Junctions," Applied Physics Letter, vol. 86, p. 153901-1-153901-3, (Apr. 2005).
Liu et al., "Controllable Nanogap Fabrication on Microchip by Chronopotentiometry," Electrochimica Acta, vol. 50, pp. 3041-3047, (2005).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reichert et al., "Driving Current Through Single Organic Molecules," Physical Review Letters, vol. 88(17), pp. 176804-1-176804-4, (Apr. 2002).
Reed et al., "Conductance of a Molecular Junction Reports," Science, vol. 278, pp. 252-254, (Oct. 1997).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Kraft, "Doped Diamond: A Compact Review on a New, Versatile Electrode Material," International Journal of Electrochemistry, vol. 2, pp. 355-385, (May 2007).
USPTO; Notice of Allowance dated May 11, 2020 in U.S. Appl. No. 16/073,706.
USPTO; Notice of Allowance dated Jun. 1, 2020 in U.S. Appl. No. 16/076,673.
USPTO; Non-Final Office Action dated Jun. 2, 2020 in U.S. Appl. No. 16/684,338.
USPTO; Non-Final Office Action dated Jun. 15, 2020 in U.S. Appl. No. 16/878,484.
USPTO; Non-Final Office Action dated Jun. 30, 2020 in U.S. Appl. No. 16/479,257.
USPTO; Non-Final Office Action dated Jun. 30, 2020 in U.S. Appl. No. 16/477,106.
EP; European Search Report dated Jun. 18, 2020 in Application No. 16815467.2.
CN; Office Action dated Jun. 5, 2020 in Chinese Patent Application No. 2017800204782.
EP; European Search Report dated Jun. 26, 2020 in Application No. 17874229.2.
Li et al., "Graphene Channel Liquid Container Field Effect Transistor as pH Sensor," Hindawi Publishing Corp., Journal of Nanomaterials 2014.
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, in U.S. Appl. No. 16/152,190.
USPTO; Non-Final Office Action dated Jun. 25, 2019 in U.S. Appl. No. 15/979,135.
USPTO; Final Office Action dated Jun. 19, 2019 in U.S. Appl. No. 16/015,049.
USPTO; Final Office Action dated Jul. 10, 2019 in U.S. Appl. No. 15/050,270.
PCT; International Search Report and Written Opinion dated Jan. 18, 2019 in Application No. PCT/US2018/055264.
EP; European Search Report dated Jan. 30, 2019 in Application No. EP16815467.2.
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cosofret et al., "Microfabricated Sensor Arrays Sensitive to pH and K+ for Ionic Distribution Measurements in the Beating Heart," Analytical Chemistry, vol. 67, pp. 1647-1653, (1995).

(56) References Cited

OTHER PUBLICATIONS

Henry et al., "Microcavities Containing Individually Addressable Recessed Microdisk and Tubular Nanoband Electrodes," Journal of The Electrochemical Society, vol. 146(9), pp. 3367-3373, (1999).
Lin et al., "An Addressable Microelectrode Array for Electrichemical Detection," Analytical Chemistry, vol. 80, pp. 6830-6833, (2008).
Thompson, "Solid-State Dewetting of Thin Films," Department of Materials Science and Engineering, vol. 42, pp. 399-434, (2012).
USPTO; Requirement for Restriction dated Jan. 17, 2017 in U.S. Appl. No. 15/336,557.
USPTO; Advisory Action dated Mar. 14, 2017 in U.S. Appl. No. 15/050,270.
USPTO; Non-Final Office Action dated May 16, 2017 in U.S. Appl. No. 15/336,557.
USPTO; Final Office Action date Dec. 30, 2016 in U.S. Appl. No. 15/050,270.
USPTO; Non-Final Office Action dated Sep. 29, 2017 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Final Office Action dated Jul. 10, 2018 in U.S. Appl. No. 15/050,270.
USPTO; Final Office Action dated Jul. 10, 2018 in U.S. Appl. No. 15/728,400.
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Notice of Allowance dated Oct. 11, 2018 in Application No. 15/796,080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/18950.
PCT; International Search Report and Written Opinion dated Jul. 26, 2017 in Application No. PCT/US2017/017231.
PCT; International Preliminary Report on Patentability dated Aug. 14, 2018 in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Fink et al., "Electrical Conduction Through DNA Molecules," Nature, vol. 398, pp. 407-410, (Jan. 20, 1999).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Bechelany et al., "Synthesis Mechanisms of Organized Nanoparticles: Influence of Annealing Temperature and Atmosphere," Crystal Growth and Design, vol. 10, pp. 587-596, (Oct. 21, 2010).
H. Nishida, et al., "Self-Oriented Immobilization of DNA Polymerase Tagged by Titanium-Binding Peptide Motif," Langmuir, vol. 31, pp. 732-740, (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267, pp. 291-297, (Aug. 10, 1989) (Abstract Only).
Park, S.J. et al., "Array-Based Electrical Detection of DNA with Nanoparticle Probes," Science, vol. 295, pp. 1503-1506, (Feb. 22, 2002).
Urban, M. et al., "A Paralleled Readout System for an Electrical DNA-Hybridization Assay Based on a Micro structured Electrode Array," Review of Scientific Instruments, vol. 74, pp. 1077-1081, (Jan. 2003) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).
Ruttkowski, E. et al., "CMOS Based Arrays of Nanogaps Devices for Molecular Devices," Proceedings of 2005 5th IEEE Conference on Nanotechnology, vol. 1, pp. 438-441, (Jul. 2005) (Abstract Only).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Schrott, W. et al., "Metal Electrodes in Plastic Microfluidic Systems," Microelectronic Engineering, vol. 86, pp. 1340-1342, (Jun. 2009).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).

(56) References Cited

OTHER PUBLICATIONS

Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Chen, X. et al., "Electrical Nanogap Devices for Biosensing," Materials Today, vol. 13, pp. 28-41, (Nov. 2010).
Ghindilis, A. et al., "Real Time Biosensor Platforms Fully Integrated Device for Impedimetric Assays," ECS Transactions, vol. 33, pp. 59-68, (2010).
Su, Y., "Modeling and Characteristic Study of Thin Film Based Biosensor Based on COMSOL," Mathematical Problems in Engineering, Article 581063 (6 Pages), (Apr. 7, 2014).
Blossey, R., "Self-Cleaning Surfaces-Virtual Realities," Nature Materials, vol. 2(5), pp. 301-306, (May 2006).
Cassie, A.B.D. et al., "Wettability of Porous Surfaces," Transitions of the Faraday Society, vol. 40, pp. 546-551, (Jan. 1944) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Coulson S.R. et al., "Super-Repellent Composite Fluoropolymer Surfaces," The Journal of Physical Chemistry B., vol. 104(37), pp. 8836-8840, (Aug. 2000).
Gapin, A.I. et al., "CoPt Patterned Media in Anodized Aluminum Oxide Templates," Journal of Applied Physics, vol. 99(8), pp. 08G902 (1-3), (Apr. 2006).
Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010) (Abstract Only).
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for DNA Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella Pnuemophila," Anal. Chem., vol. 79, pp. 4050-4055, (Jun. 1, 2007).
Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Notice of Allowance dated Oct. 23, 2019 in U.S. Appl. No. 16/250,929.
USPTO; Non-Final Office Action dated Oct. 24, 2019 in U.S. Appl. No. 16/073,706.
USPTO; Notice of Allowance dated Nov. 8, 2019 in U.S. Appl. No. 16/015,028.
USPTO; Non-Final Office Action dated Nov. 5, 2019 in U.S. Appl. No. 16/015,049.
USPTO; Notice of Allowance dated Dec. 11, 2019 in U.S. Appl. No. 15/979,135.
USPTO; Notice of Allowance dated Jan. 6, 2020 in U.S. Appl. No. 15/050,270.
USPTO; Non-Final Office Action dated Jan. 10, 2020 in U.S. Appl. No. 16/076,673.
EP; European Search Report dated Oct. 24, 2019 in U.S. Appl. No. 17/757,146.
USPTO; Non-Final Office Action dated Sep. 22, 2020 in U.S. Appl. No. 16/639,716.
USPTO; Non-Final Office Action dated Nov. 9, 2020 in U.S. Appl. No. 16/731,749.
PCT; International Search Report and Written Opinion dated Jun. 9, 2020 in Application No. PCT/US2020/13218.
PCT; International Search Report and Written Opinion dated Aug. 6, 2020 in Application No. PCT/US2020/25068.
PCT; International Search Report and Written Opinion dated Sep. 4, 2020 in Application No. PCT/US2020/28004.
EP; European Search Report dated Sep. 30, 2020 in Application No. 17893481.6.
JP; Office Action dated Aug. 13, 2020 in Japanese Application No. 2017-566864.
CN; Office Action dated Aug. 14, 2020 in Chinese Patent Application No. 201680083636.4.
Ali et al., "DNA hybridization detection using less than 10-nm gap silicon nanogap structure," Sensors and Actuators A, vol. 199, pp. 304-309 (2013).
Bornholt, et al. "A DNA-Based Archival Storage System," Architectural Support for Programming Languages and Operating Systems, pp. 637-349 (2016).
Chen et al., "Silicon nanowire field-effect transistor-based biosensors for biomedical diagnosis and cellular recording Investigation," Nano Today, Elsevier, Amsterdam NL, vol. 6, No. 2, pp. 131-154 (2011).
European Search Report dated Dec. 14, 2020 in Application No. 18799263.1.
European Search Report dated Dec. 23, 2020 in Application No. 18790713.4.
European Search Report dated Nov. 19, 2020 in Application No. 18739158.6.
Final Office Action dated Dec. 14, 2020 for U.S. Appl. No. 16/684,338.
Final Office Action dated Jan. 11, 2021 for U.S. Appl. No. 16/479,257.
Final Office Action dated Jan. 6, 2021 for U.S. Appl. No. 16/070,133.
Grass et al. "Robust Chemical Preservation of Digital Information on DNA in Silica with Error-Correcting Codes," Angewandte Chemie International Edition, vol. 54, No. 8, pp. 2552-2555 (2015).
Hatcher et al., "PNA versus DNA Effects of Structural Fluctuations on Electronic Structure and Hole-Transport Mechanisms," J. Amer. Chem. Soc. 130, pp. 11752-11761 (2008).
Japanese Office Action dated Dec. 2, 2020 in Application No. 2018-536737.
Korlach et al. "Real-time DNA sequencing from single polymerase molecules," 11, Methods in Enzymology, Academy Press, vol. 472, pp. 431-455 (2010).
Notice of Allowance dated Dec. 7, 2020 for U.S. Appl. No. 16/878,484.
Notice of Allowance dated Nov. 24, 2020 for U.S. Appl. No. 16/477,106.
Office Action dated Dec. 15, 2020 for U.S. Appl. No. 16/831,722.
Office Action dated Dec. 30, 2020 for U.S. Appl. No. 16/652,672.

(56) References Cited

OTHER PUBLICATIONS

Paul et al. "Charge transfer through Single-Stranded Peptide nucleic Acid Composed of Thymine Nucleotides," J. Phys. Chem. C 2008, 112, pp. 7233-7240 (2008).
Shin et al. "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Venkatramani et al. "Nucleic Acid Charge Transfer: Black, White and Gray," Coard Chem Rev., 255(7-8): pp. 635-648 (2011).
Office Action dated Jul. 12, 2021 for CN Application No. 201780020711.7.
Sek, Slawomir, et al. "Conductance of a-Helical Peptides Trapped within Molecular Junctions," J. Phys. Chem. B 2006, 110, 19671-19677.

* cited by examiner

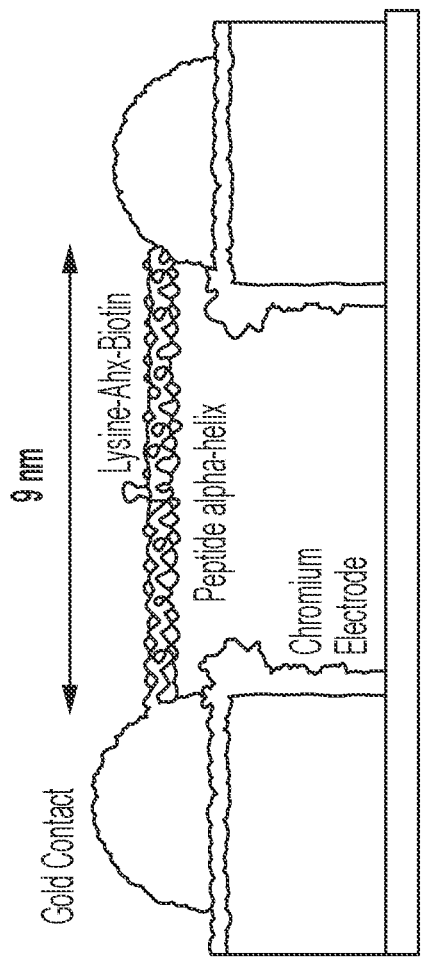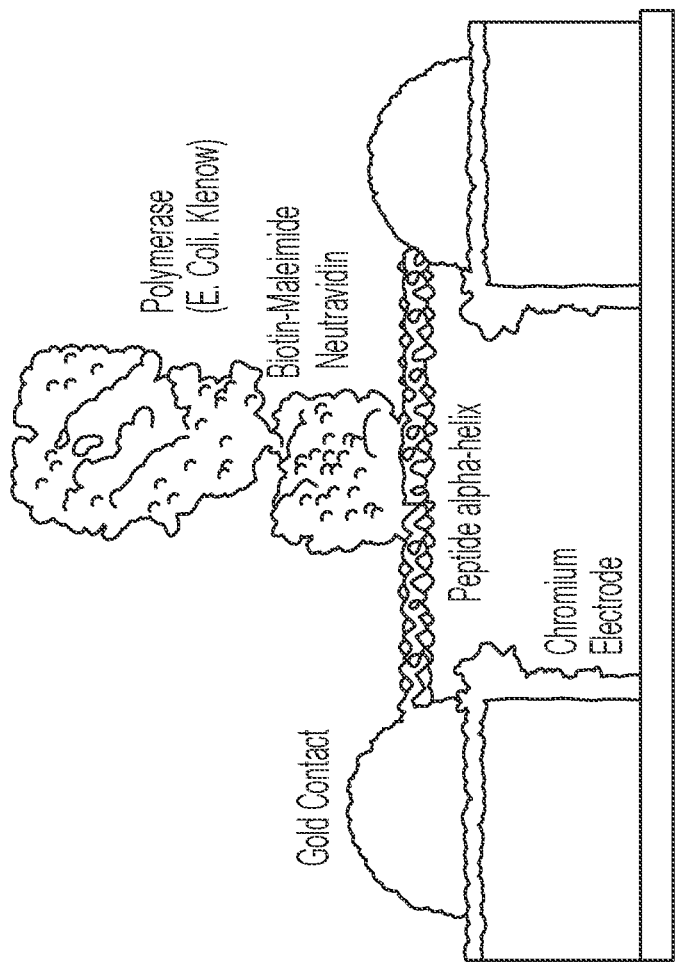
FIGURE 58A
FIGURE 58B

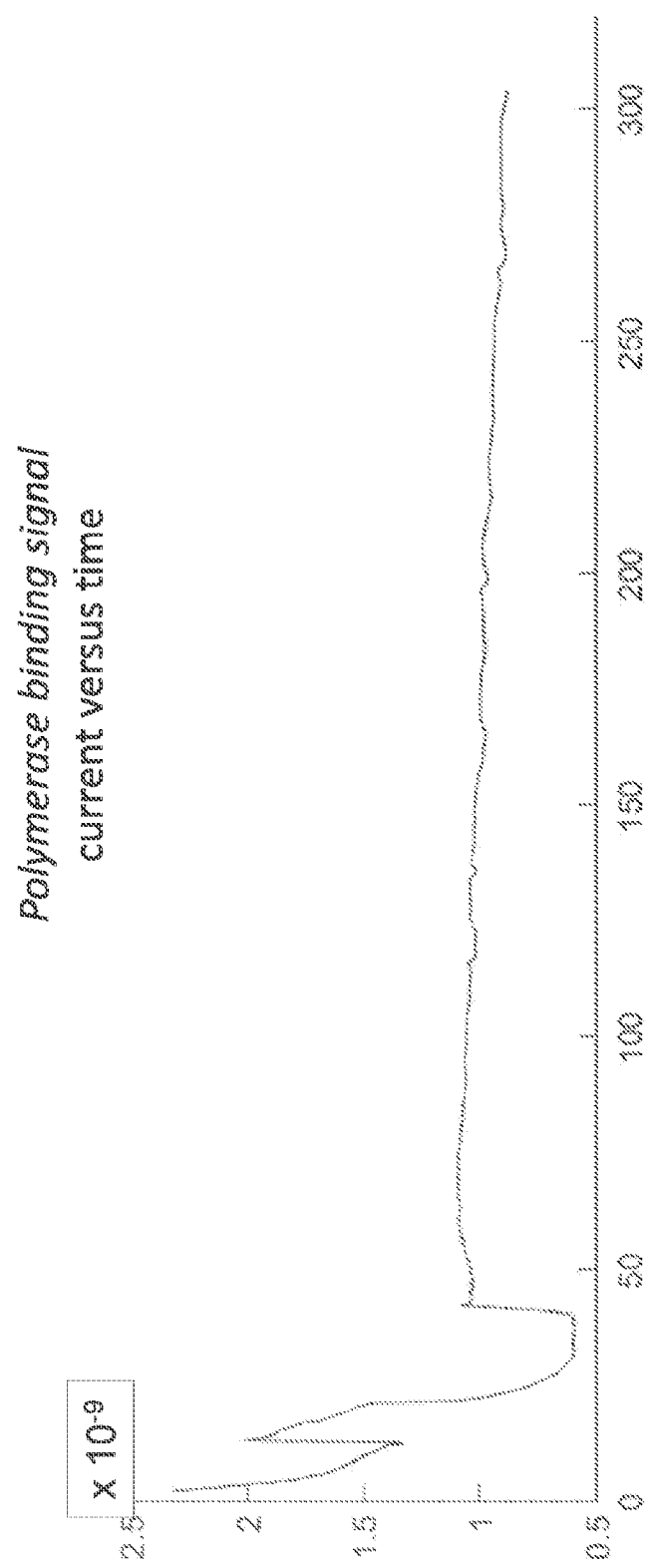

| PARAMETER | VALUE |
|---|---|
| AREA (EST.) | 20 μm$^2$ |
| $R_{ON}$ | 13-15 kΩ |
| $R_{OFF}$ | > 1 TΩ |
| $I_{LEAK}$ (IN) | < 100 fA |
| $I_{LEAK}$ (OUT) | < 5 pA |

FIGURE 66

| PARAMETER | VALUE |
|---|---|
| POWER | 12.6 μW |
| AREA (EST.) | 3,425 μm$^2$ |
| A0 | 83.1 dB |
| GBW | 327 kHz |
| PM | 83.4° |
| 3dB BW | 22.8 kHz |
| INPUT-REFERRED NOISE | 133.9 nV/√Hz |

FIGURE 69

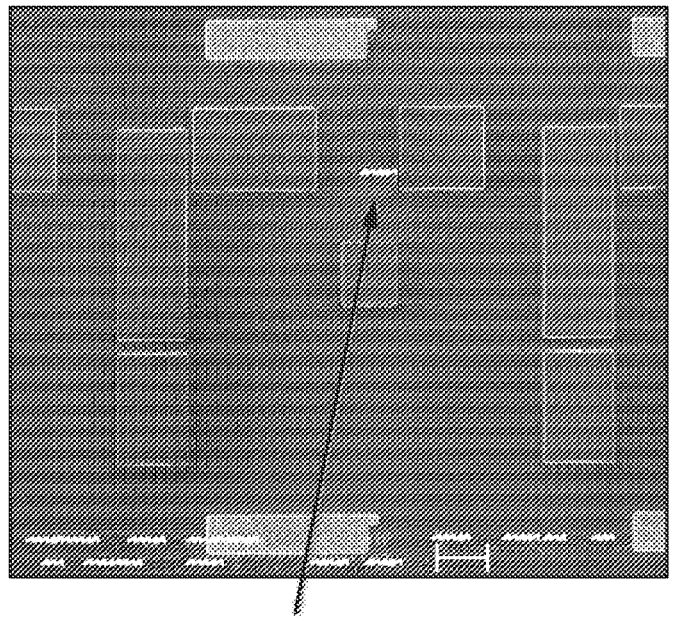
Site for Nano-Electrodes, showing exposed Vias for Source, Gate and Drain nanoelectrodes
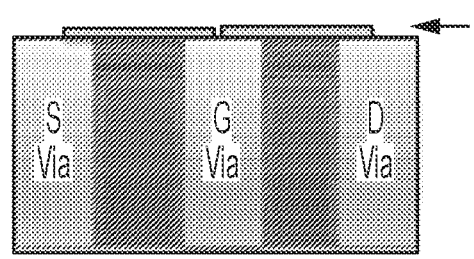
Site Cross Section
Nano electrodes (to be added in post processing)
FIGURE 78B

METHODS AND APPARATUS FOR MEASURING ANALYTES USING POLYMERASE IN LARGE SCALE MOLECULAR ELECTRONICS SENSOR ARRAYS

CROSS-REFERENCE TO RELATED APPLICATIONS

This application is a U.S. national phase filing under 35 U.S.C. § 371 of PCT/US2017/015465 filed on Jan. 27, 2017, which claims priority to U.S. Provisional Application No. 62/288,360, filed on Jan. 28, 2016 and entitled "METHODS AND APPARATUS FOR MEASURING ANALYTES USING LARGE SCALE MOLECULAR ELECTRONICS SENSOR ARRAYS," the disclosures of which are incorporated herein by reference.

FIELD

This invention is generally in the field of bio-nanotechnology and more particularly in the field of molecular electronics sensors.

BACKGROUND

Sensors are discrete systems that undergo a detectable, recordable change of state in response to a particular class of stimuli. When combined a suitable means of interpretation, sensors can be used to characterize or quantify other systems of interest. This concept is indicated generally in FIG. 1.

FIG. 1 illustrates general operation of a sensor to measure a property of a physical system. A suitable sensor device is brought into some form of contact or interaction with a physical system of interest that causes a change in state of the sensor device, followed by some form of read-out or recording of a signal, which can then be subsequently interpreted to define the measured property.

In principle, a spatial array of such sensors allows many such sensing events to be performed in parallel. A spatial array may be in the form of a 1-dimensional, 2-dimensional or even 3-dimensional array. When such parallel measures are performed at a large scale, they can be used to reproduce or infer complex properties of the physical system under evaluation, as shown generally in FIG. 2. In particular, the sensor array can consist of diverse sensor types that inform on various properties of the system simultaneously, as well as similar types of sensors that measure the same property, but from different parts of the complete physical system, at the same time. Thus the sensor array, in conjunction with data reduction and interpretation methods, can achieve measurement of complex system properties that are derived from diverse lower level properties, and diverse parts of the system, nearly simultaneously.

FIG. 2 illustrates that sensor arrays can be used to obtain many measures of a physical system in parallel, which can then be processed and interpreted to determine higher-level measure features of interest of the target physical system. This provides a means of measuring features that depend on diverse properties, and at distributed parts or the overall system.

In the field of bio-analyte measurement, the application of DNA sequencing has attracted a number of large scale sensor array approaches because large numbers of measurements are need to determine the sequence of whole genomes of most organisms, and this is most practically done via some form of parallel sensor array. DNA microarrays were the first successful sensor array approach, in the form of sequencing by hybridization performed on a microarray platform, in the early 2000's. Subsequently, various forms of sensor array-type systems were developed, typically in the form of large scale arrays of DNA templates—single molecule or locally clonally amplified—that were engaged a series of sequencing chemistry detection reactions, utilizing optical reporter techniques and CCD or CMOS image sensors to record results. More fully integrated DNA sequencing sensor arrays were developed, all of which used dedicated arrays of electronic sensors, fully or partially integrated on chip, which directly sensed suitable voltage or current signatures related to the sequence of DNA fragments undergoing analysis.

FIG. 3 illustrates that a molecular electronic sensor element in accordance to the present disclosure is assembled as a single molecule bridging between two electrode terminals. These devices are of nanometer scale, as indicated.

An object of this invention is to provide sensor array systems that can be manufactured as semiconductor chips, along with methods of using such sensor arrays to produce accurate measurements of analytes or other measurements of interest. More specifically, sensor array chips designs that can be manufactured in large part through CMOS processes, and methods that are based on synthesis of the results of highly parallel, single-molecule sensing. The invention includes a variety of preferred embodiments that can support specific novel applications.

SUMMARY

In various embodiments of the present disclosure, a molecular electronics sensor array chip is disclosed, which includes an integrated circuit semiconductor chip and a plurality of molecular electronic sensor devices disposed thereon, with each of the sensor devices including (i) a pair of nanoscale source and drain electrodes separated by a nanogap; (ii) a gate electrode; and (iii) a bridge or probe molecule spanning the nanogap and connecting the source and drain electrodes. The plurality of sensor devices are organized into an array of sensor pixels. In certain aspects, the sensor devices include a bridge molecule and a probe molecule, wherein the probe molecule is bound to the bridge molecule that spans the nanogap. In certain embodiments, a chip may include hundreds up to hundreds of millions or more of the sensor devices. Voltages may be used to monitor and/or facilitate a molecular self-assembly process, whereby each bridge and/or probe molecule self-assembles on to each source and drain electrode pair. Device voltages may be used to monitor and/or facilitate molecular self-assembly of each bridge and/or probe molecule to each source and drain electrode pair, including the use of a voltage-directed reset to restore the sensor to a pre-molecular state as may be needed for successive trials.

In various embodiments, the probe molecule may be a binding probe for an analyte including, but not limited to, DNA, RNA, or proteins. In other aspects, the probe molecule may be an enzyme, a DNA hybridization probe, DNA polymerase, or RNA polymerase. In various embodiments, the probe molecules are DNA polymerase and the bridge molecule comprises double stranded DNA, a peptide, a protein alpha helix, or a native or engineered IgG antibody, spanning specific affinity contact points on each electrode pair.

In various embodiments, an array architecture is discloses. For example, each sensor pixel of a chip may include a readout capacitor or readout resistor connected to each sensor device. In certain aspects, each sensor pixel may further include a transistor-based output switch and/or a transistor-based reset switch. In various embodiments, each sensor pixel may further include a row select line and a column readout line connected thereto, and the array of sensor pixels may have an integrated row select column-readout array architecture, with the row select lines used to energize the sensor pixels. In some examples, the row select lines control the output switches. Each sensor pixel may include a row-reset line and a column-reset line for controlling each reset switch. Each reset switch may be controlled by a combination of the row select line and the column-reset line, such as to provide direct control over the reset of each sensor pixel.

In various embodiments of the present disclosure, a process for measuring signals of incorporation for a multiplicity of replicate primed DNA fragments applied to a chip is disclosed. The method includes providing at least one molecular electronics sensor array chip as disclosed here, applying a mixture of dNTPs and specific base terminators to the molecular electronics sensor array chip, and measuring the specific base locations along the fragment. In some instances, at least four (4) molecular electronics sensor array chips are utilized, such as one for each base reaction. Such a process may be used to perform a digital fragment length assay.

In various aspects of the present disclosure, a chip-based analyzer system is disclosed. A chip-based analyzer system, such as for sample analysis, includes at least one of the molecular electronics sensor array chips disclosed herein, a motherboard in which the at least one molecular electronics sensor array chip is integrated, a liquid handling system configured to control introduction of at least the sample to the plurality of molecular electronic sensor devices, at least one signal processor, and a CPU. The chip-based analyzer system may also include at least one of a mass storage device, a system DRAM, and an auxiliary control computer, and it may be integrated into a multi-modality bio-analyzer, thereby producing a multi-modality integrated report from the sample. The analyzer may also be configured to be hand-held, wearable or even implantable. The type of analysis may include, but is not limited to, DNA fingerprinting, genotyping, or DNA sequencing. These types of analyses find use, for example, in healthcare and law enforcement.

In various embodiments of the present disclosure, a process for analyzing a bio-sample is disclosed. The method includes providing a chip-based analyzer system such as disclosed above, collecting the bio-sample from a subject (e.g. any living or dead organism or a soil or water sample from the environment), processing the bio-sample through the chip-based analyzer system to obtain data relevant to an analysis of the bio-sample, and transferring the data to a storage server or to the cloud.

In various examples, the bio-sample is collected from a subject in conjunction with information pertaining to the subject, and analyzed to produce an integrated report comprising both the information pertaining to the subject and the data relevant to the analysis of the bio-sample. In certain aspects, the subject is a human, an animal, a plant, an insect, a bacteria, a soil sample, a water sample, or a material specimen comprising biomaterials. The analysis may be a genetic analysis that produces a DNA fingerprint, genotyping, or DNA sequencing. Bio-samples may be collected from a multiplicity of subjects, and the data obtained aggregated to form a database. For human or veterinary subjects, the analysis may be DNA sequencing and the data can be transferred to a precision report (e.g. a report used by a practitioner) that relates to the subject's health and/or healthcare program. In certain examples, the analysis yields DNA fingerprinting and the data is transferred to a precision report that relates to identification of the subject, such as may be required in law enforcement. In other embodiments, the subject is the environment, and the chip-based analyzer is used to provide distributed, remote monitoring of the environment or an analysis of a soil or water sample, for purposes such as in pollution monitoring.

In various embodiments of the present disclosure, a process for selecting an enzyme based on sensor-derived quantitative performance is disclosed. The method includes providing at least one molecular electronics sensor array chip as disclosed herein, and establishing a multiplicity of enzymes as the probe molecules. The process may also include selecting a probe molecule based on sensor-derived quantitative performance.

In various embodiments, a process for estimating a quantity or low-dimensional feature of a sample analyte is disclosed. The method includes providing at least one molecular electronics sensor array chip as disclosed herein, and applying a data fitting process to the data to determine a best fit for the quantity. In the process, the fitting processes may include at least one of an average, least squares fit, L1 optimization, cost functional optimization, maximum likelihood, and/or compressive sensing technique.

In various embodiments of the present disclosure, a process to physically capture targets based on their quantitative sensor-derived measures is disclosed. The process includes providing at least one molecular electronics sensor array chip as disclosed herein and applying the targets to the molecular electronics sensor array chip. In this process, undesirable targets are electronically ejected and flushed from the chip, and desired targets are retained and then electronically ejected for collection.

In various embodiments of the present disclosure, a CMOS chip is disclosed. The CMOS chip includes an integrated circuit semiconductor chip, a plurality of molecular electronic sensor devices disposed on the chip, with each of the sensor devices including (i) a pair of nanoscale source and drain electrodes separated by a nanogap; (ii) a gate electrode; and (iii) a bridge or probe molecule spanning the nanogap and connecting the source and drain electrodes, and any one of a row select module, a column-decoder module, and an I/O module. The sensor devices may be organized into an array of sensor pixels. In certain embodiments, the CMOS chip may be mounted in packaging providing electrical pinouts that provide high-bandwidth I/O, with the chip encased in a molded plastic flow cell that provides for the introduction of liquid reagents or analytes for convenient exposure to the array of sensor pixels.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

FIGS. 58A and 58B illustrate an embodiment of a sensor based on a peptide alpha-helix bridge molecule;

FIGS. 59A, 59B, 59C and 59D set forth data from s Sequence Sensing Experiment using the alpha-helix peptide bridge;

FIG. 66 summarizes exemplary parameters for pixel switch performance;

FIG. 69 provides parameters for pixel amplifier performance;

FIGS. 78A and 78B are electron microscope images of a finished CMOS chip and pixel.

DETAILED DESCRIPTION

Figure 1:
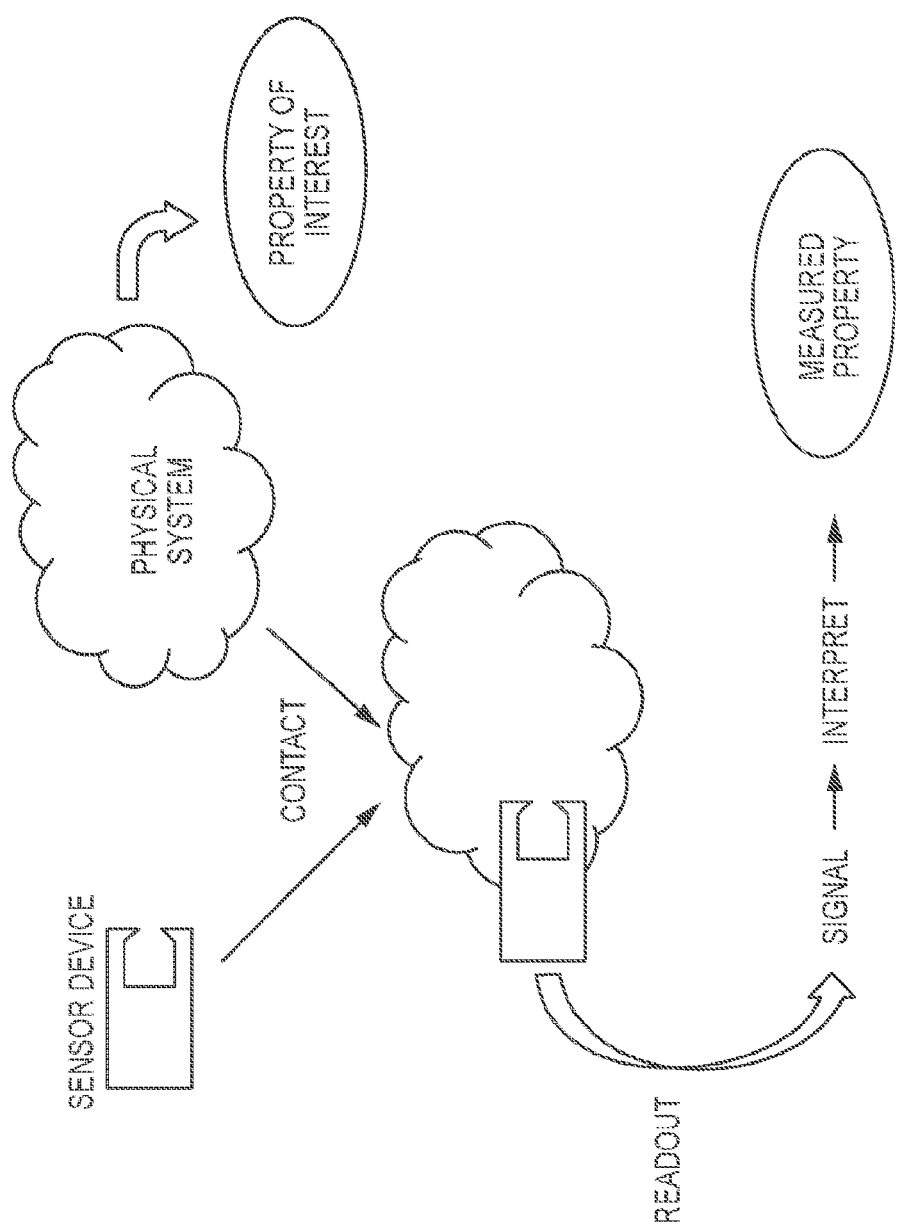
FIG. 1 illustrates general operation of a sensor to measure a property of a physical system.
Figure 2:
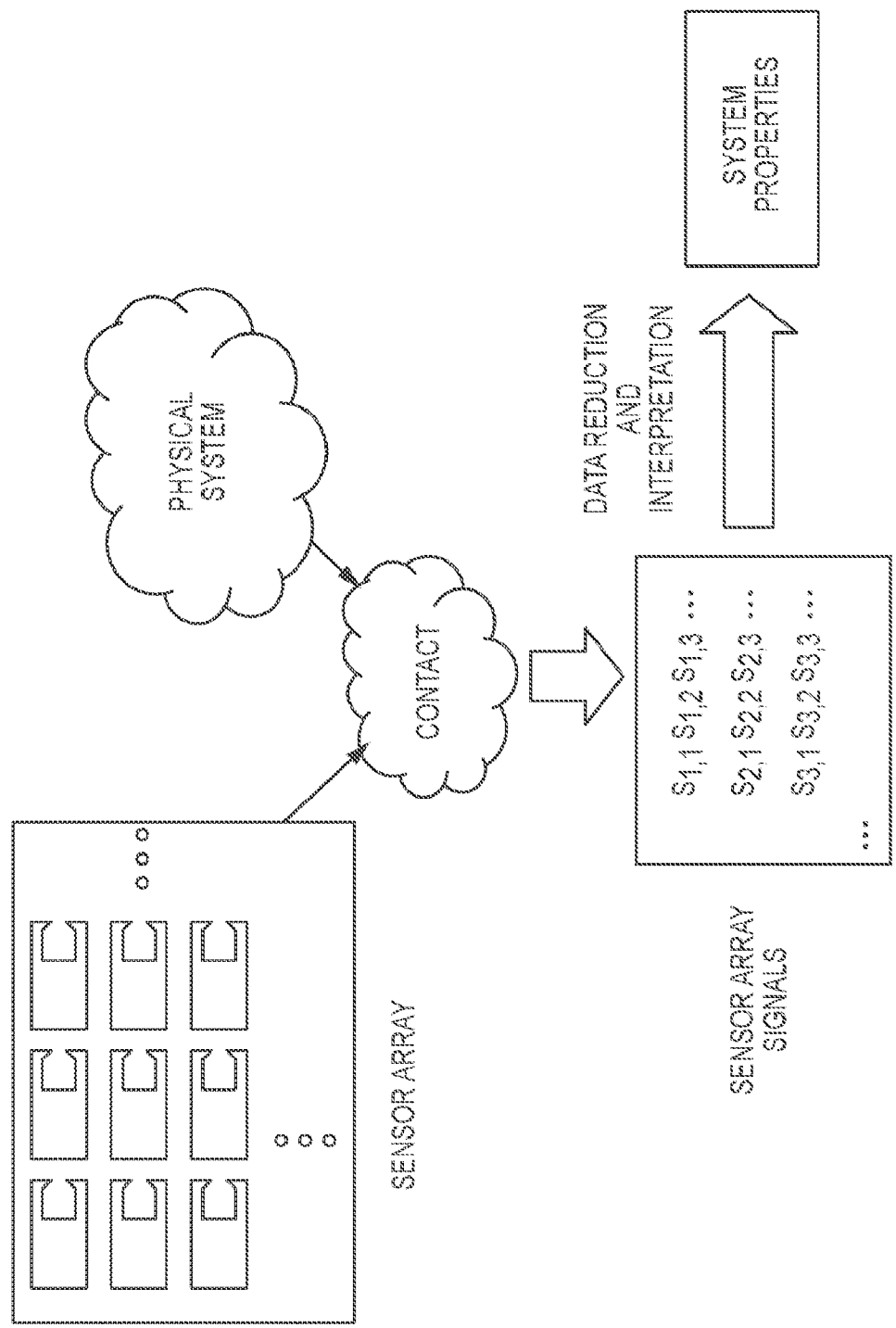
FIG. 2 illustrates that sensor arrays can be used to obtain many measures of a physical system in parallel, which can then be processed and interpreted to determine higher-level measure features of interest of the target physical system.
Figure 3:
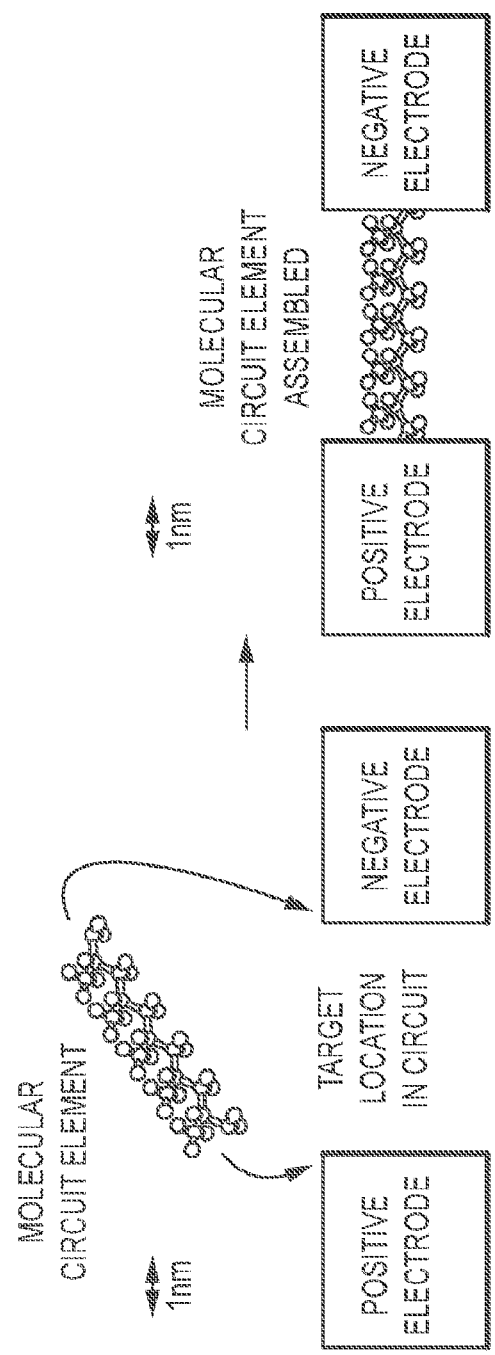
FIG. 3 illustrates a typical molecular electronic element sensor comprising a single molecule bridging between two electrode terminals.

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

The scope of the present disclosure encompasses general forms of a molecular electronics sensors that are useful elements for sensor array applications. This consists of a probe molecule coupled into a three terminal device comprising source and drain electrodes, and a gate electrode for additional voltage control.

Definitions

Any term not expressly defined should be given the common meaning known to a person skilled in the art.

As used herein, the term "analyte" refers to a chemical entity, such as DNA, RNA, or a protein that may be the subject of an analysis, such as to determine the identity or amount of the chemical entity, or it may refer to a reagent used in an analysis.

As used herein, the acronym "CMOS" refers to "conductive metal oxide semiconductor," which is a particular method used for constructing integrated circuits.

As used herein, the acronym "FPGA" refers to a "field programmable gate array," which is an integrated circuit designed to be configured by a third party after manufacturing, i.e. in the "field."

As used herein, the acronym "GPU" refers to a "graphics processing unit," which is a circuit that rapidly manipulates and alters memory to speed up the making of images in a frame buffer. A GPU is often used together with a CPU to accelerate various applications.

As used herein, the acronym "DSP" refers to "digital signal processor," and "DSP chip" refers to a digital signal processor chip, which is a specialized microprocessor for measuring, filtering and processing analog signals.

As used herein, the acronym "ASIC" refers to "application specific integrated circuit," and "ASIC chip" refers to an ASIC in the form of a chip.

As used herein, the term "CPU" refers to a "central processing unit," which is the computer circuitry that carries out the instructions of a computer program, and the term "Multicore CPUs" refers to a component with two or more independent CPUs.

As used herein, the term "N^6 primers" refers to short oligodeoxyribonucleotides in random sequence with up to $4^6$ different sequences. The term may also be denoted as "[d(N)6]."

As used herein, the acronym "LNA" refers to "locked nucleic acids," which are a type of nucleic mimetic, also referred to as "inaccessible RNA" having an extra bridge connecting the 2' and 4' carbons.

As used herein, the acronym "PNA" refers to "peptide nucleic acids," which are artificially synthesized polymers similar to DNA or RNA, but instead having a backbone of repeating N-(2-aminoethyl)-glycine units.

As used herein, the acronym "SNP" refers to "single nucleotide polymorphism," which is a common type of genetic variations among persons.

As used herein, the term "SNP genotyping" refers to a type of genotyping that measures genetic variations of single nucleotide polymorphisms (SNPs) between members of a species.

As used herein, the term "subject" refers to, in a non-limiting way, a human, a non-human animal (or herein, "animal"), a plant, a bacterium, a virus, an amoeba, a fungi, a yeast, a soil sample, a water sample, or an air sample, or any other sample either known to contain or that could contain biological materials. In the broadest sense, a subject is a living or dead organism (marine or terrestrial), the environment, or a sample of the environment (e.g. a water sample from a stream or river or a soil sample).

As used herein, the term "polymerase" refers to an enzyme that catalyzes the formation of a polymer, such as DNA or RNA. "DNA polymerase" participates in the polymerization of nucleotides into DNA. "RNA polymerase" participates in the polymerization of nucleotides into RNA.

As used herein, the acronym "SMU" refers to "source/monitor unit," which is a device capable of forcing a voltage and a current while simultaneously measuring voltage and current.

As used herein, the acronym "VIA" refers to "vertical interconnect access," meaning an electrical connection between layers in an electronic circuit.

In various aspects of the present disclosure, a molecular electronics sensor array chip comprises an integrated circuit semiconductor chip and a plurality of molecular electronic sensor devices disposed thereon and organized into an array of sensor pixels, Each sensor device comprises a pair of nanoscale source and drain electrodes separated by a nanogap, a gate electrode, and a bridge and/or probe molecule spanning the nanogap and connecting the source and drain electrodes. The plurality of sensor devices may comprise only bridge molecules, only probe molecules, or both bridge and probe molecules.

Within the scope of the present disclosure, the plurality of sensor devices may be organized on the chip using any scalable array architecture, such as one that allows chips spanning several orders of magnitude to be designed by setting a scale parameter within a parameterized family of designs.

In various embodiments of chip architecture, each sensor pixel may further comprise a readout capacitor or readout resistor connected to each sensor device. Also, each sensor pixel may further comprise a transistor-based output switch and/or a transistor-based reset switch. In various aspects, each sensor pixel may be connected to a row select line and a column readout line, and with the array of sensor pixels integrated into a row select/column readout architecture, the row select lines can be used to energize the sensor pixels.

In various embodiments, a row select/column-readout array architecture allows for the row select lines to control the output switches. Each sensor pixel may further comprise a row-reset line and a column reset line for controlling each resent switch. In certain embodiments, each reset switch may be controlled by a combination of the row select line and the column-rest line, such as to provide direct control over the reset of each sensor pixel.

A molecular electronics sensor array chip in accordance to the present disclosure may comprise at least 100 sensor devices. In other variations, a chip may comprise at least 10,000, at least 100,000, at least 1,000,000, at least 10,000,000, or at least 100,000,000 or more sensor devices.

The molecular electronics sensor array chip of claim may be fabricated in stages, such as by using a CMOS process for the electronics, nanolithography for the nano-electrodes, and molecular self-assembly for attachment of the molecular elements. The nanolithography method may comprise nano-imprint lithography. In certain aspects, the molecular electronics sensor array chip may be fabricated entirely by CMOS technology, or implemented in a CMOS chip.

In various embodiments, voltages are used to monitor and/or facilitate a molecular self-assembly of each bridge and/or probe molecule to each source and drain electrode pair. For example, device voltages can be used to monitor and/or facilitate molecular self-assembly of each bridge and/or probe molecule to each source and drain electrode pair, including the use of a voltage-directed reset to restore the sensor to pre-molecular state as needed for successive trials.

In various embodiments of a molecular electronics sensor array chip, the probe molecule may comprise an enzyme, such as for example, a DNA or RNA polymerase, or a DNA hybridization probe. In certain aspects, the probe molecules may comprise binding probes of protein, peptide, aptamer or hapten form. In other variations of the chip, the probe molecules may comprise DNA polymerase and the bridge molecule may comprise double stranded DNA, a peptide, a protein alpha helix, or a native or engineered IgG antibody, spanning specific affinity contact points on each electrode pair. Such chips can be applied to measure signals of incorporation for a multiplicity of primed DNA fragments applied to the molecular electronics sensor array chip.

In various embodiments, a molecular electronics sensor array chip in accordance to the present disclosure may further comprise hybridization probes used to perform a digital hybridization assay. The probes provide for SNP genotyping or gene expression measurement for genome mapping of a set of fragments, or provide a set of designed universal hybridization tags for decoding assays that yield tag-based readout. In certain aspects, combinitorical decoding hybridizations are used in conjunction with identifying probes on the array that are combinatorically encoded.

In various embodiments, the molecular electronics sensor array chip may further comprise single base extension hybridization probes used to perform a digital single base extension sequencing assay, or binding probes to perform a digital binding assay. In certain aspects, hybridization assays use sensor-voltage controlled attraction and repulsion of DNA to accelerate hybridization and improve measurement fidelity or to obtain an electronic melting point curve to characterize the binding.

In various embodiments, a probe molecule may comprise a binding probe for a particular analyte. An analyte may comprise at least one of DNA, RNA and a protein. In certain embodiments, the concentration of the analyte may be determined.

In various embodiments of a molecular electronics sensor array chip, sensor-voltages are used to produce attraction, repulsion, functional changes, and changes to local ionic environment, in regards to the probe molecule, bridge and its target.

In various embodiments, features of the nano-electrodes in a molecular electronics sensor array chip are designed using simple line and spot patterning for maximal resolution in patterning systems used in chip fabrication.

In various embodiments of the present disclosure, a process for measuring signals of incorporation for a multiplicity of replicate primed DNA fragments applied to a chip comprises: (a) providing a molecular electronics sensor array chip; (b) applying a mixture of dNTPs and specific base terminators to the molecular electronics sensor array chip; and (c) measuring the specific base locations along the fragment. In certain embodiments, this process may comprise the use of at least four (4) molecular electronics sensor array chips, such as one for each base reaction. These processes can be used to perform a digital fragment length assay, or applied to a set of marker fragments comprising a DNA fingerprint, such as usable for identification. Such processes may involve a survey of diverse parameters for the probe-target interaction across the array, thereby ascertaining parameter settings for optimal operation.

In various embodiments of the present disclosure, a chip-based analyzer system for sample analysis comprises at least one molecular electronics sensor array chip such as disclosed above, integrated into a motherboard. Such a chip-based analyzer system may further comprise a liquid handling system, at least one signal processor, a solid state storage buffer, data storage, at least one CPU, a system DRAM and a mass storage device. Such analyzer systems may further comprise data transfer capabilities, and may interface with an auxiliary control computer. In such a system, sample preparation, minimal data processing and data transfer may be integrated into one compact within the system, such that it is suitable for use in mobile, portable, hand-held or embeddable applications. In certain examples, the sample comprises a biological sample (a bio-sample) taken from a subject, such as a human. A bio-sample may be collected from a subject in conjunction with information pertaining to the subject (e.g. if a human subject, age, height, weight, etc.), and analyzed to produce an integrated report comprising both the information pertaining to the subject and the data relevant to the analysis of the bio-sample. Such reports are useful in the health profession.

In various embodiments of the present disclosure, a bio-sample for analysis in a chip-based analyzer system may be, for example, a human, an animal, a plant, an insect, a bacteria, a soil sample, a water sample, or any other material specimen comprising at least something of interest to analyze, such as any biomaterial. In various examples, the analysis may comprise a genetic analysis producing a DNA fingerprint, genotyping, or DNA sequencing. A DNA fingerprint thus obtained may be useful in a identification process, such as in law enforcement. In some aspects, bio-samples may be collected from a multiplicity of subjects, and then the data aggregated to form a database that can be referenced at some time in the future. Such a database may comprise machine learning on the database to produce a knowledge base capable of providing precision reports. DNA sequencing thus obtained can be transferred in the form of precision reports that relate to healthcare.

In various embodiments, a chip-based analyzer may be integrated into a multi-modality bio-analyzer, thereby producing a multi-modality integrated report from a sample, such as a bio-sample. The chip-based analyzer may provide genetic analysis, such as, but not limited to, DNA fingerprinting, genotyping, and DNA sequencing. In some embodiments, the chip-based analyzer is configured to be hand-held, wearable, or implantable. In certain aspects, a chip-based analyzer may provide distributed, remote monitoring of the environment. Such environmental monitoring may be used for pollution monitoring and control.

Figure 4:
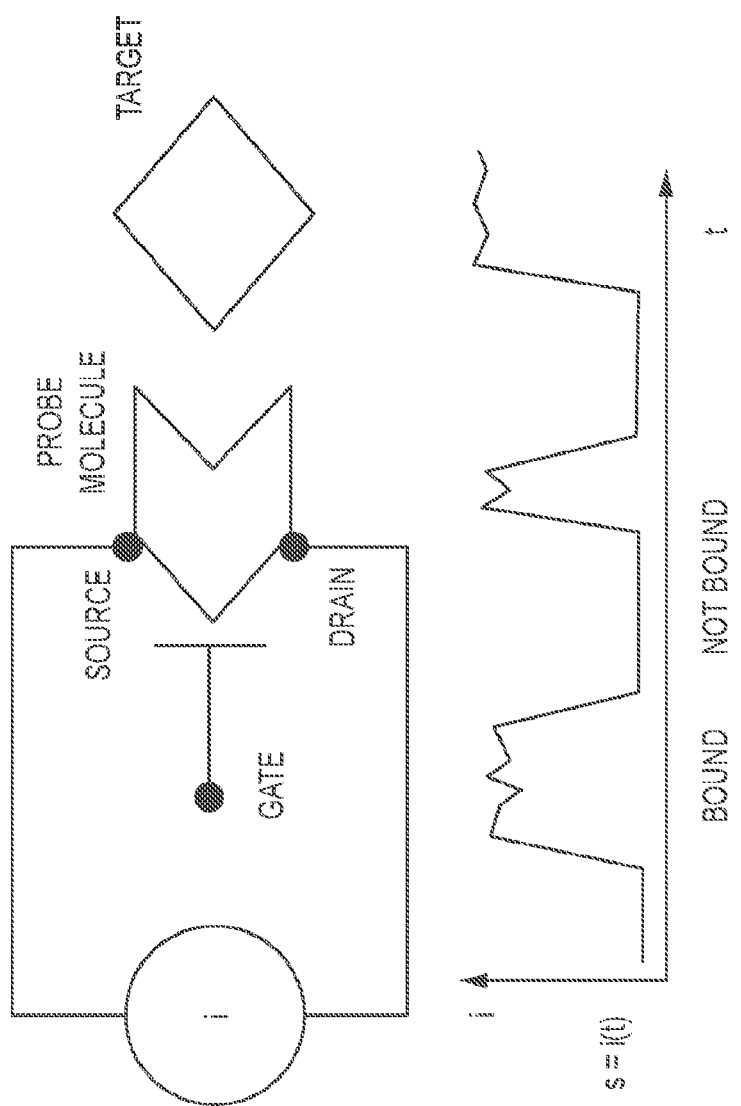
FIG. 4 illustrates a schematic of one preferred form of a molecular electronics circuit for measuring probe-target interactions.

A preferred schematic embodiment of a molecular electronics circuit for measuring probe-target interactions is shown in FIG. 4, wherein the probe molecule is coupled between source and drain electrodes as a primary circuit element, and the overall circuit is configured with a meter measuring an electrical property (such as current in the circuit under applied source-drain and gate voltages, or voltage under applied currents), and where the measured trace is thereby related to the interaction of the probe with its target. This configuration is preferred when the probe-target complex conformations substantially alter the conduction of charge through/around the complex. The measured property S(t) as a time trace reflects the underlying probe-target interactions, due to the conformational changes that result, as well as the variable properties as an electrical component during this processing.

Figure 5:
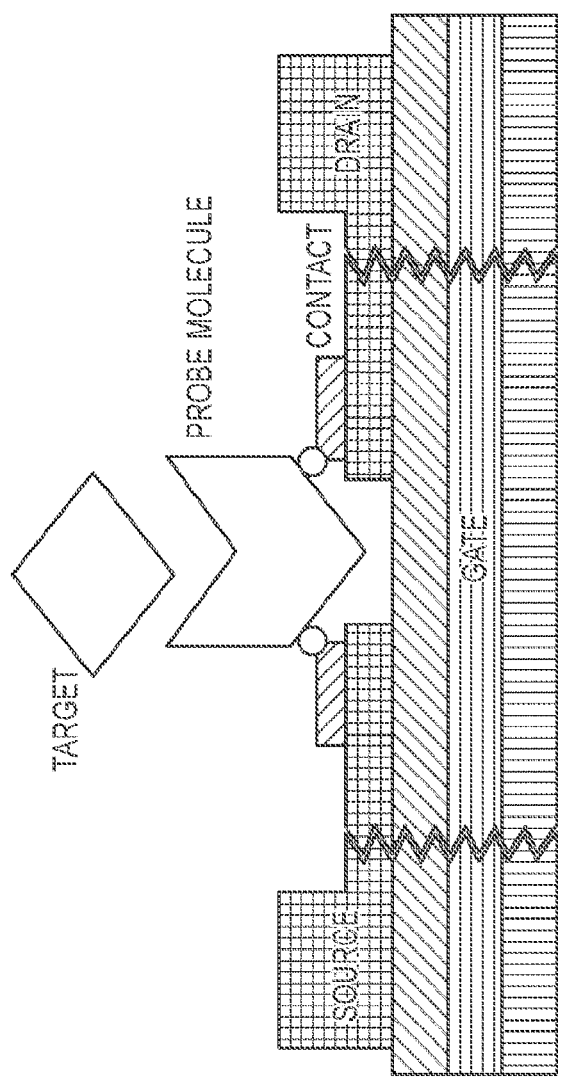
FIG. 5 illustrates an embodiment of local electrode configuration relative to standard source-drain gate geometries used in semiconductor transistor devices.

With reference now to FIG. 5, a local electrode configuration is illustrated in a more detailed form, relative to standard source-drain and gate geometries used in semiconductor transistor devices. In this non-limiting embodiment, the probe molecule is coupled in as a secondary or parallel circuit element, which may have both conducting and gating activity relative to a primary conductive element, and wherein the overall circuit is configured with a meter for measuring an electrical property (such as current in the circuit under applied voltages, or voltage under applied currents), and where measured trace is thereby related to the probe-target interaction. This configuration is preferred when the probe-target conformational changes can apply variable gating voltages to the primary conducting element, acting principally as another gate electrode applying sequence-dependent gate voltages.

Figure 6:
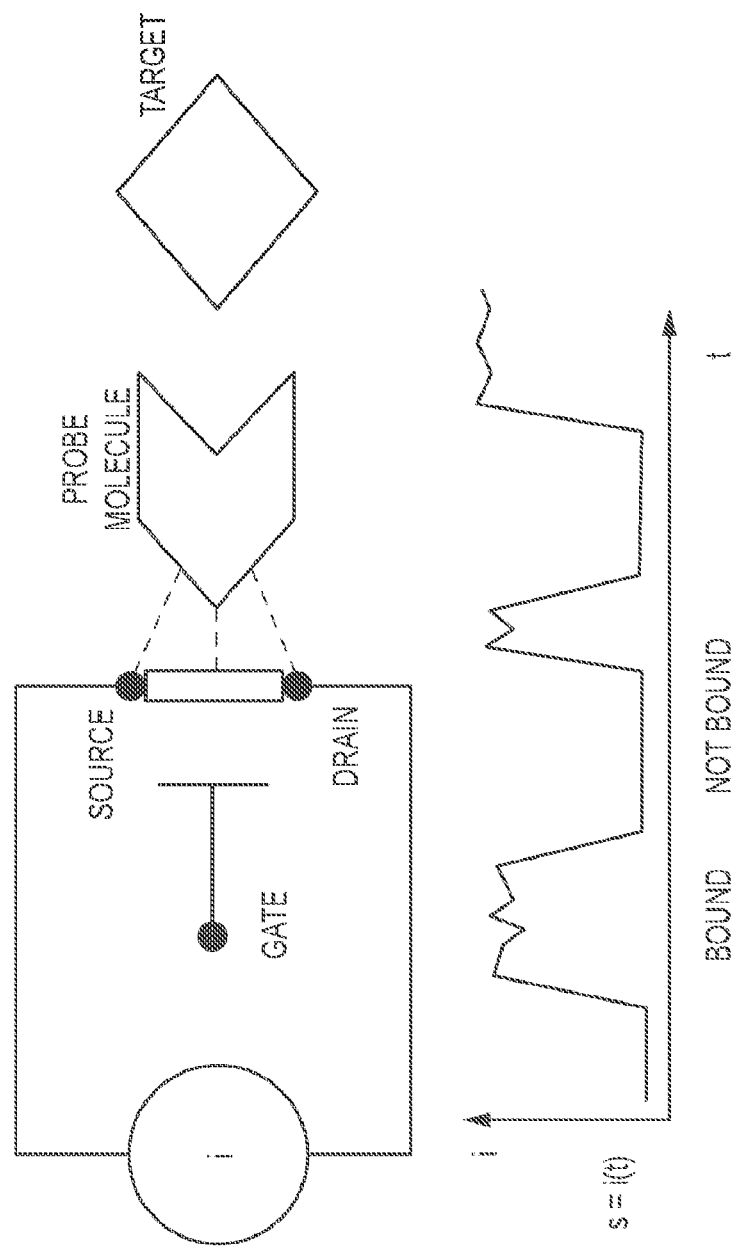
FIG. 6 illustrates a schematic of another preferred form of a molecular electronics circuit for measuring probe-target interaction.

FIG. 6 illustrates a schematic of another preferred form of a molecular electronics circuit for measuring probe-target interaction. A probe molecule is coupled as a secondary element to a primary conducting element between source and drain electrodes, to form a circuit in which the probe may provide gating function as well as conduction. The circuit includes a meter for measuring an electrical property, such as current under applied source-drain and gate voltages, or a similar system property (such as voltage at constant applied current). The measured property S(t) as a time trace reflects the underlying probe-target interaction.

Figure 7:
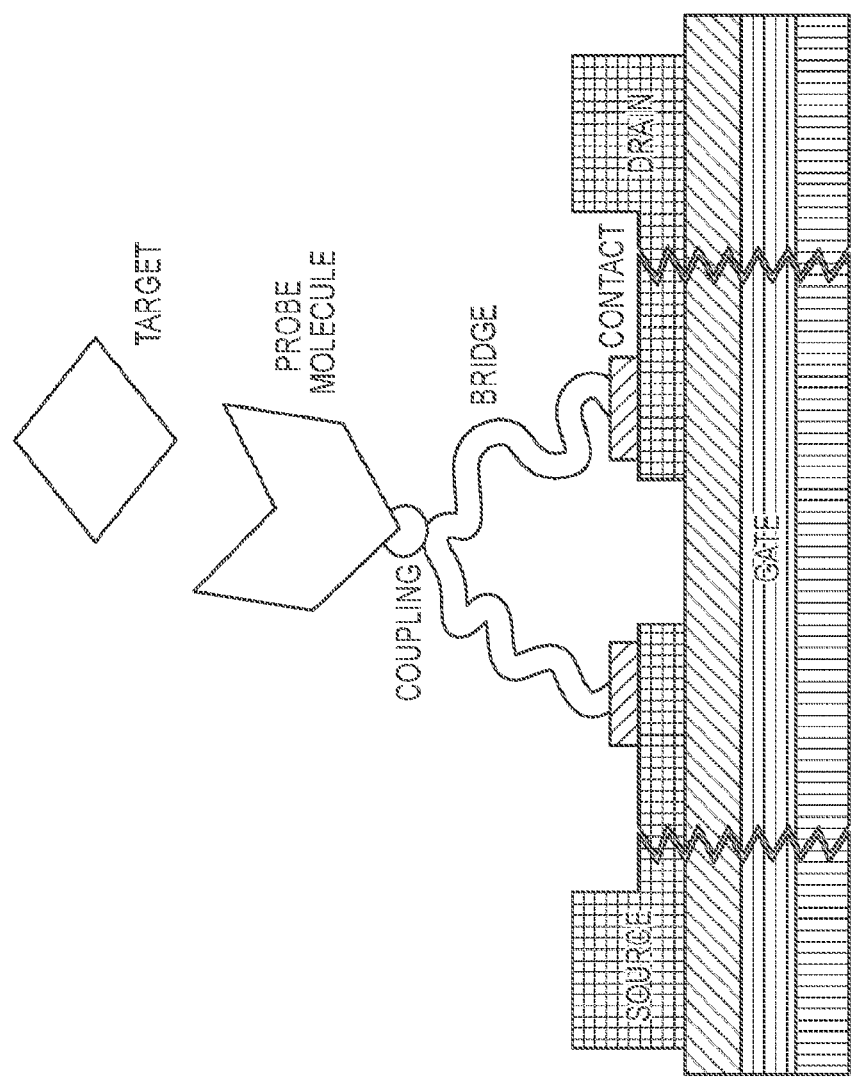
FIG. 7 depicts the schematic of FIG. 4, in a more detailed preferred embodiment with a source-drain-gate geometry from semiconductor devices, a molecular bridge between electrodes, and a coupling point or conjugation group that couples the enzyme to the bridge.

FIG. 7 illustrates the schematic of FIG. 4, in a more detailed embodiment with a source-drain-gate geometry from semiconductor devices, and a molecular bridge between electrodes as the primary conducting element, and a coupling point or conjugation group that couples the enzyme to the bridge, as one means of ensuring proximity, and potentially electrical connection. As illustrated, the probe molecule is tethered to ensure proximity and/or a conductive connection between probe molecule and bridge.

Figure 8:
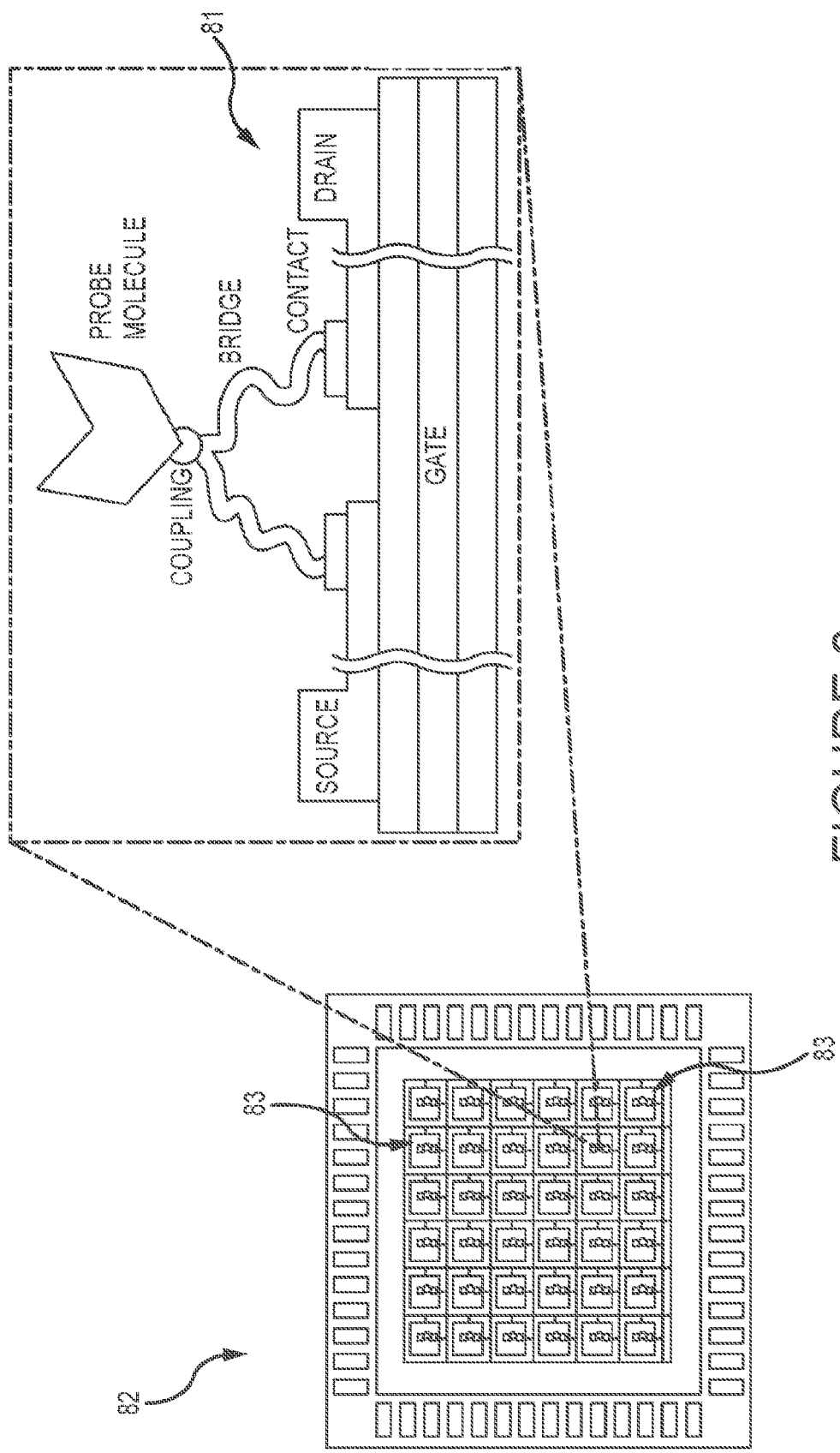
FIG. 8 illustrates an embodiment of a chip-based sensor array configuration.

FIG. 8 illustrates an embodiment of a chip-based sensor array configuration. For all such sensors as outlined herein, any may be organized as a sensor array chip, such as indicated in FIG. 8, which is able to read out the sensor signals on the array at a high sampling rate or frame rate, so that they may be effectively read in parallel while undergoing exposure to a common solution of analytes. In various embodiments, these sensor array chips may comprise any number of sensors, from 100's to 1000's to millions to billions or more of such sensors.

In various embodiments, chip formats can comprise the following key elements of functionality: (1) support for electronically controlled self-assembly, disassembly (reset/erase), reassembly and calibration of the molecular elements into the sensor circuitry, and of the sensors on the array; (2) support for rapid sampling of all sensors in the array, and transfer of such data off chip, so that many sensors can be effectively monitored in parallel; and (3) a scalable array architecture, so that chips with sensor counts spanning several orders of magnitude can be designed simply by setting an array size parameter in a parameterized family of circuit designs.

Array chips can be fabricated through a hierarchy of processes, in which much or all of the electronic circuitry and electrode array is made via CMOS processes, the nano-electrode features are made using a nanolithography process, and the molecular components are assembled using molecular self-assembly techniques. In an embodiment, these self-assembly techniques are directed or accelerated by use of the voltage controls on the electronics, such as the local gate voltage. In various embodiments, the nano-electrodes are also made using CMOS fabrication processes operating at or below 16 nm, and preferably at or below 10 nm, semiconductor device fabrication node. Alternatively, nano-imprint lithography can efficiently fabricate the array of nano-electrodes, imprinting an entire chip nano-electrode pattern from each impression.

Array chips can be incorporated into a complete system that supports an application of the sensor chip, including integrated liquid handling and data transfer, data analysis, and data storage.

As illustrated in FIG. 8, a chip-based sensor array configuration may include. molecular electronic sensors 81 configured into an array on a semiconductor chip 82, with suitable input/output pins 83 (illustrated as the small block shapes on the ends of source and drain electrodes, on opposite ends of the gap). The typical dimensions of such a chip are indicated as the 1 mm scale, while the dimensions of the sensor are down at the 10 nm scale. The array architecture can further be scalable, allowing chips to comprise 100's to thousand to millions to billions of sensors based on a common circuit design. The I/O pins and architecture support electronic control over assembly, and calibration of sensors, and the elimination or resetting thereof, as well as the high speed sampling and readout of the sensor signals, so that they can effectively be read in parallel at a high frame rate.

Figure 9:
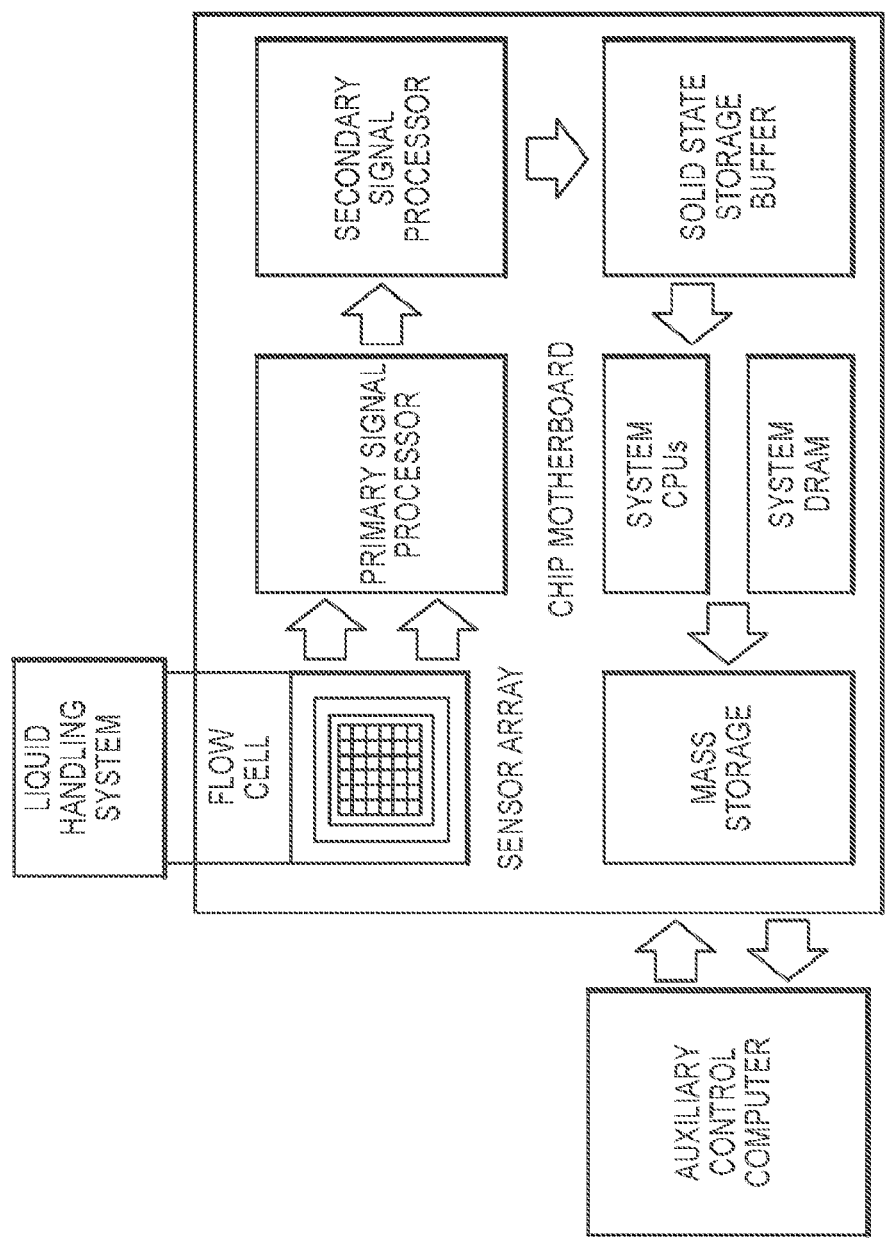
FIG. 9 illustrates an embodiment of a chip-based analyzer system.

An embodiment of a high level system has the general form shown in FIG. 9. As illustrated, a motherboard houses the chip, encased in suitable flow cell, and connected to a liquid transfer system. Data from the chip is transferred to a primary data processing unit, for high speed reduction, and, potentially, to a second such processor for further reduction. Such processors can, in various embodiments, comprise any of FPGAs, GPUs, or DSP chips, or custom ASIC chips, or multicore CPUs. After this initial data processing, the reduced data is stored in a fast, short term storage buffer, preferentially solid state drive memory, subsequent to being passed to the CPUs for further processing, and then longer term storage, as well as transfer to an auxiliary computer for further processing, or transfer to another computer or storage server.

FIG. 9 illustrates an exemplary chip-based analyzer system. The sensor array chip is integrated into a system that supports efficient analysis of samples. An exemplary embodiment of such a system is shown, and comprises: a liquid handling system, which may comprise pumps and valves to control the introduction of sample and reagents to the sensor; a first signal processor and optionally a second signal processor; a solid state high-speed storage buffer; and at least one system CPU. In various aspects, data from the one or more signal processors may be buffered through the high-speed buffer, with short-term storage as necessary, for CPU-based processing and longer-term storage, such as in an on-board mass storage device as shown. The system may further comprise a dynamic random access memory device (DRAM) as shown. The CPU-based processing may reduce and/or otherwise process the sensor data. An auxiliary computer may be used for controlling the system and to provide a user interface, along with having the ability to transfer data to an off-system storage device or to the cloud. Data may be transferred from the system for purposes of further analysis and/or for reporting.

Figure 10:
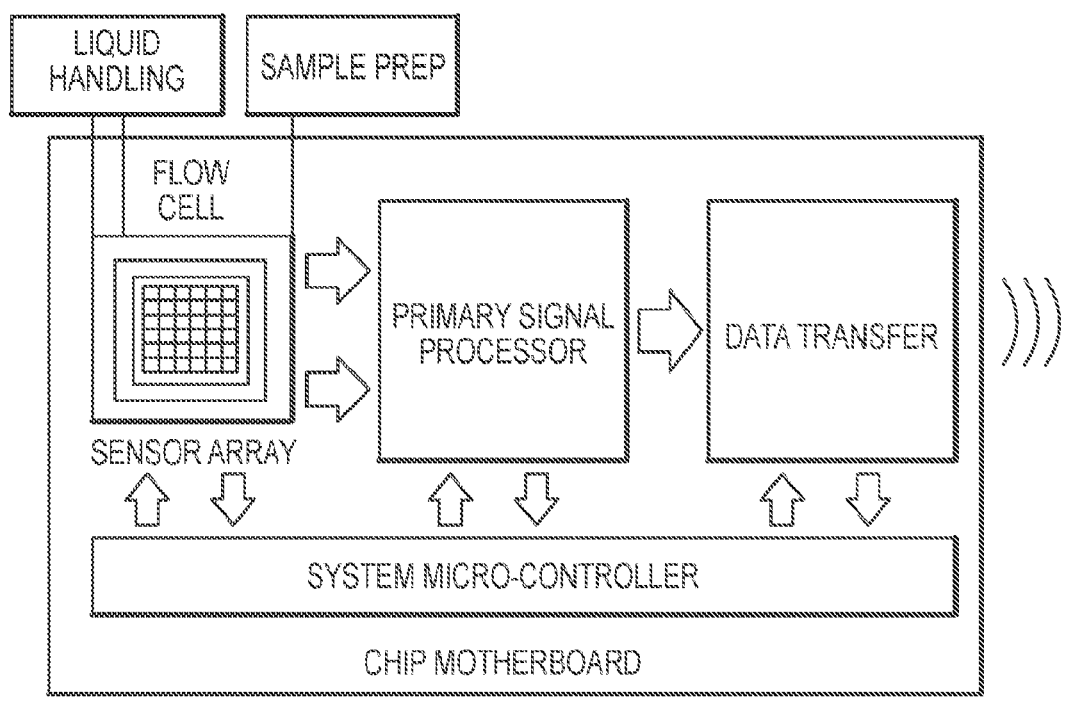
FIG. 10 illustrates an embodiment of a compact chip-based analyzer system.

In various aspects, an integrated system can be highly compact by limiting the on-board functionality and integrating in various critical functions. An example of such a compact system is shown in FIG. 10, wherein sample preparation has been integrated into the system, all critical system functions are on one motherboard, and there is wireless/cellular data transfer to move sensor data off system to a server, or to a cloud based storage resource. Such compact, integrated systems enable desktop systems, mobile systems, portable systems, point-of-use, hand-held or wearable systems. They further enable extreme minimization of the platform, such as would be required for embedded use in multi-functional instruments, in space, or in vivo.

FIG. 10 illustrates an exemplary compact chip-based analyzer system as an integrated system that provides a more compact form factor and integrated workflow. Such a system may have integrated sample preparation and wireless data transfer, such as to minimize the need for external equipment, automate workflows, and also to minimize the need for on-system electronics, computation and storage, and to make the system more portable and embeddable into a more extensive system that performs other measures and functions.

Figure 11:
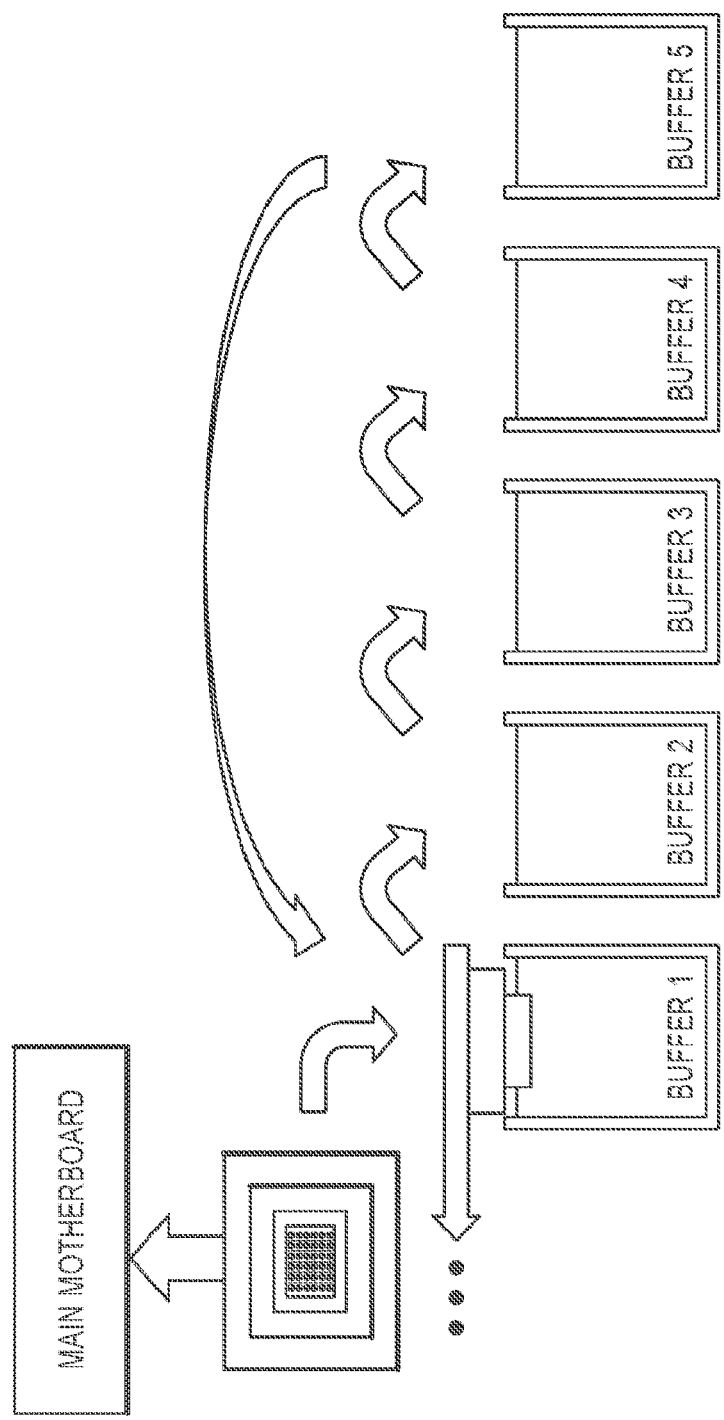
FIG. 11 illustrates an embodiment of a high efficiency dipping liquid handling system.

For the integrated systems, an alternative to a pumping system for liquid handling is a chip dipping system, such as shown for example in FIG. 11. In this system, the chip is broken out onto a mini-motherboard, with a data transfer connection back to the main motherboard that allows for the chip to be physically moved between baths of the different solutions required for sequential exposures, while still sending and receiving data. For example, a series of one or more solutions needs to be exposed to the chip sensor surface in the application of DNA sequencing. In contrast to sequential pumping of such solutions into a flow cell encasing the chip as indicated in FIG. 9, the chip is instead dipped into each solution required, and mechanically transferred between such solutions, as shown in FIG. 11. This provides the advantages of faster changing of solutions for increased speed of performing the requisite exposures, as well as more economical use of buffers, since they are not eliminated as waste after each exposure. In other embodiments, the data transfer connection is flexible electrical cable that supports a high-speed data transfer protocol (such as a ribbon connector or coaxial cable, or, more specifically, such as cables to be used with the Infiniband, SCSI, Gigabit Ethernet or 10-base T data transfer methodologies), or a wireless/cellular communications link and associated high-speed wireless protocols (such as Wi-Fi or Bluetooth, or more specifically, such as the IEEE 802.11-B/G/N/AC/AX wireless protocols, or 3G, 4G, LTE or Wi-Max cellular communications protocols).

FIG. 11 illustrates an exemplary high-efficiency dipping liquid handling system. With the sensor chip configured on a movable mini-board, these chips undergo automated dipping into the different solutions required for a given processing application. This allows for very high-speed exposures to solutions, rapid change of solution and conservation of buffers for more rapid and efficient processing of samples. Such solutions may also be at different temperatures, for energy efficient, rapid thermal cycling. The mini-board may be connected to the main-board through flexible cable or a wireless connection.

Figure 12:
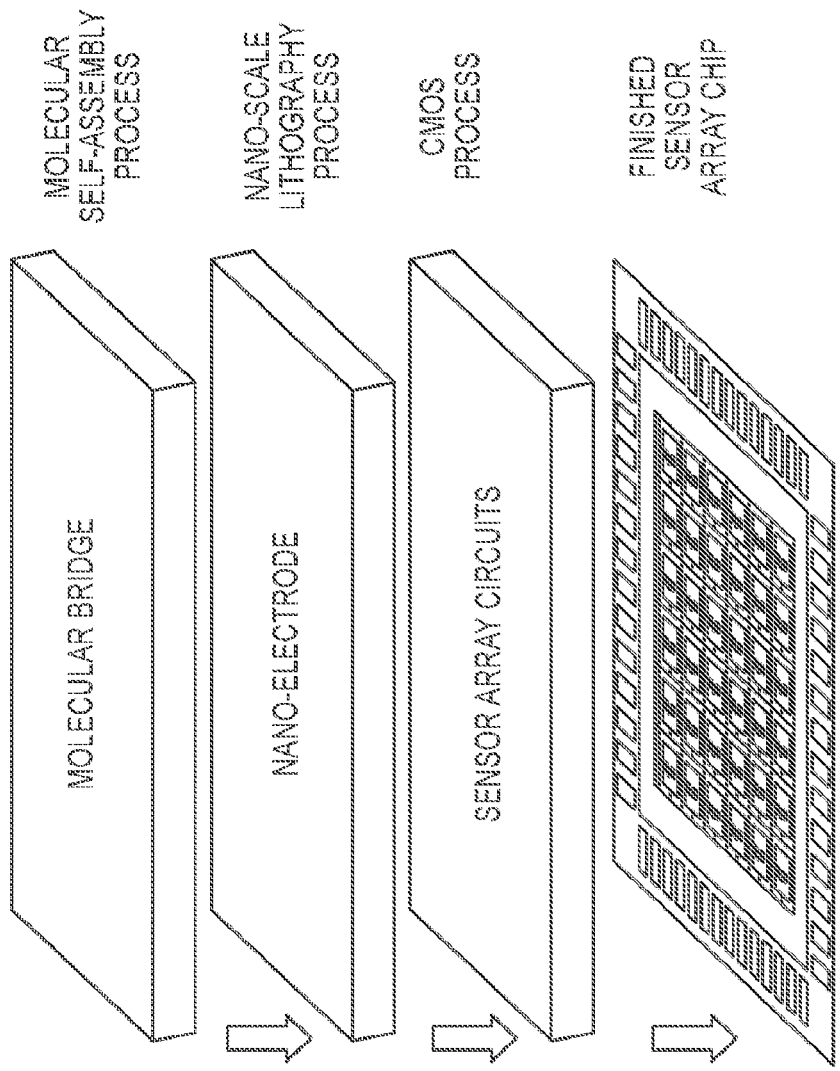
FIG. 12 illustrates exemplary processing stages of chip production.

Referring now to FIG. 12, chips can be manufactured through a hierarchy of processes, among which CMOS processes are used for the majority or all of the electronics. In an embodiment, and as illustrated in FIGS. 14 through 25, such a chip has a sensor circuitry array architecture that supports the power, timing, logical control, readout, and processing and transfer of data on/off chip (Input/Output or I/O). This layer of circuitry is preferably fabricated using a CMOS process, in order to leverage the existing semiconductor manufacturing infrastructure. Disposed on top of this layer are the critical nano-electrodes as indicated in FIGS. 6 and 7. The process involved making electrodes and gaps and contact features on a nanometer scale, preferably at or below 20 nm, and preferably at or below 10 nm. In a preferred embodiment, these electronic elements would also be made all or in part through CMOS processes, relying on fabrication nodes of 16 nm, and preferably 14 nm or 10 nm, which are capable of producing such appropriately sized features. Parts of the device not manufacturable in CMOS can be made by other nano-lithography methods, and preferably either by short wavelength or phase shift mask or multiple patterning methods of photolithography, or nano-imprint lithography, either of which provide more parallel patterning than e-beam lithography or ion-beam milling. The final aspects of the device, illustrated in FIGS. 6 and 7, are the molecular components. These are preferably established using means of molecular self-assembly in solution phase processing, directed by or enhanced by special material contact points, and also preferably through the use of the voltage controls of the electronic elements, such as the gate voltage or source-drain voltage, to influence the charged molecules and/or the local ionic conditions of the solution.

FIG. 12 illustrates exemplary processing stages for chip production. The finished chip requires major fabrication steps, the majority preferably accomplished by CMOS fabrication, such as the array and sensor circuitry, and potentially the nano-electrode fabrication. Electrode fabrication may then require further processing by any one of a diversity of nano-lithography methods, preferably nano-imprint lithography. The molecular components are established by self-assembly techniques, which may include voltage-enhanced self-assembly processes that make use of the chip electronic circuitry.

Figure 13:
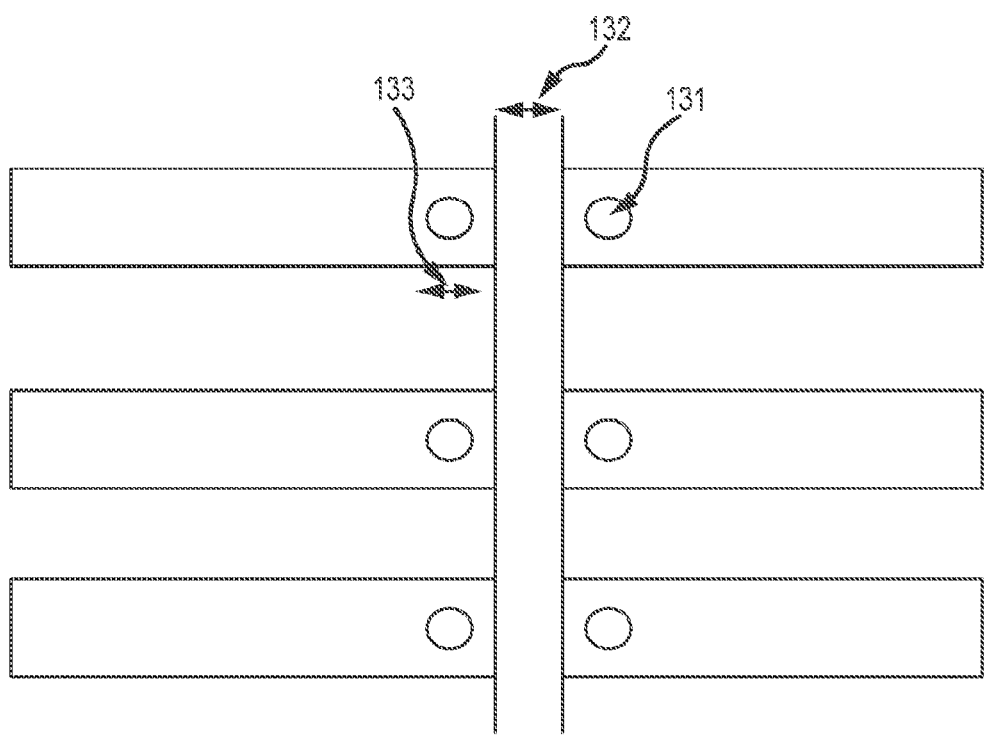
FIG. 13 illustrates embodiments of minimal dimension/high-resolution features comprising simples shapes such as line or dot.

Fabrication of the nano-electrodes and nano-contact points can be made compatible with CMOS processes, such as through the use of very simple patterning of electrode layout and simple patterning for the smallest scale features, the nano-contacts and nano-gaps. Specifically, nano-gaps should be aligned to be part of a long linear pattern feature, and circles for the nano-contact pattern features, as indicated in FIG. 13. In a preferred embodiment, the nano-gap would be patterned as a single linear trench spanning many electrode pairs. In another embodiment, contact points would be patterned as pairs of spots or disks.

FIG. 13 further illustrates that the minimal dimension/high-resolution features should have simple shapes 131 (e.g. line or dot) that are compatible with high-resolution photolithographic patterning and the highest resolution modes of various other patterning methods. Here in particular, the electrode gap 132 should be a long linear feature across many electrodes, and the nano-contact should be based on point-like or spot-like patterning 133.

Figure 14:
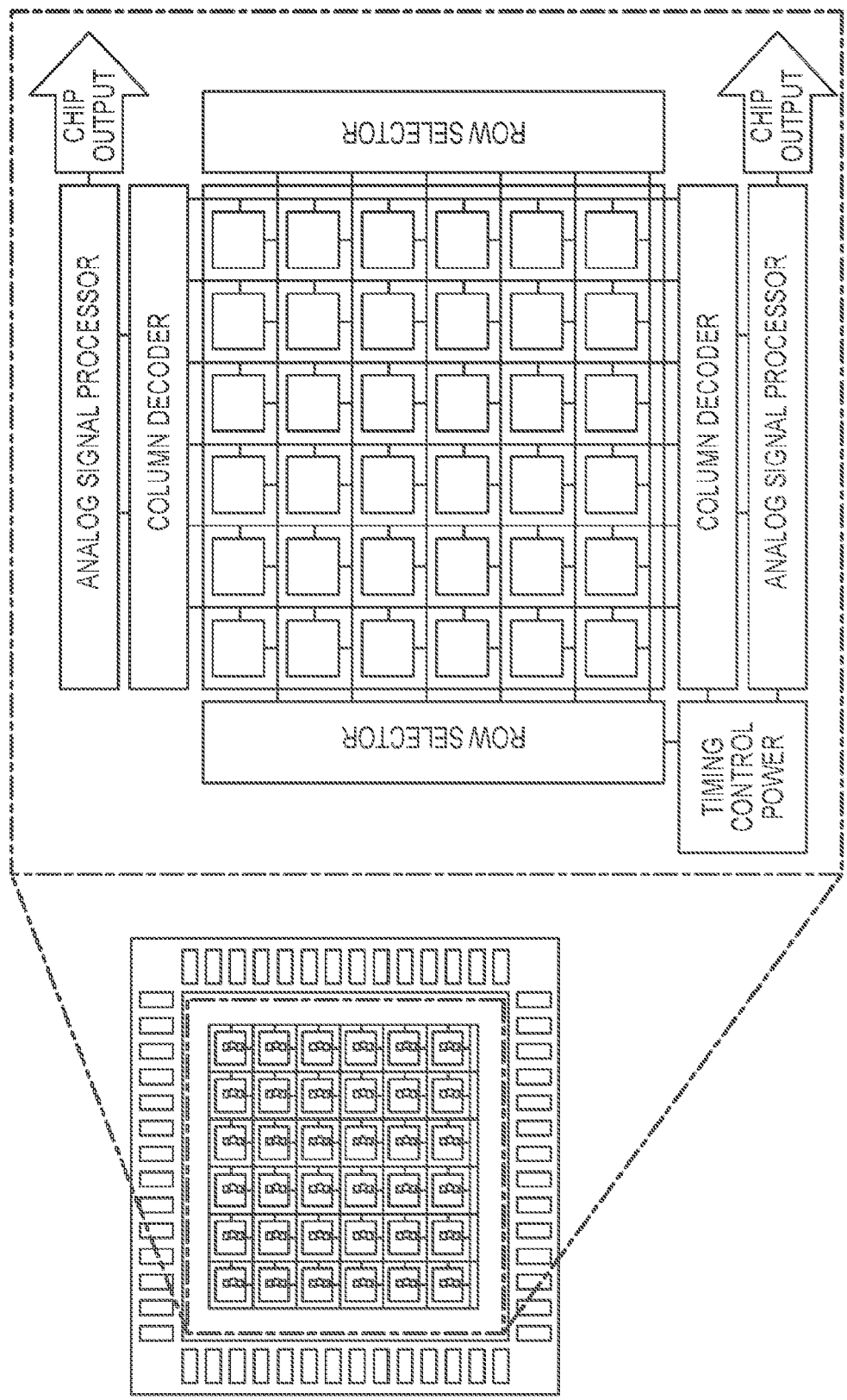
FIG. 14 illustrates an embodiment of sensor array chip architecture.

With reference now to FIG. 14, a chip may comprise a standard packaging with pinouts, such as a semiconductor chip based on a detailed architecture in which the sensor elements are organized into an array of "sensor-pixels." FIG. 14 illustrates an embodiment of sensor array chip architecture. The chip in a preferred embodiment has an architecture that leverages the elements that have been well developed for CMOS imager chips, which includes a sensor array, row and column selector and decoders, and sub-systems for timing, control, power, and analog signal processing or analog to digital signal processing, as well as I/O. Other elements of the organization, commonly used on chips, such as CMOS imager chips, are present, although such standard features preferably include circuit designs to support the real-time sample rates and signal strengths required for chip applications.

For such applications, all pixels may need to be sampled at a frequency of at least 10 Hz, preferably at least 100 Hz, and more preferably at 1 kHz. Some applications require sampling at 10 kHZ, 100 kHz and even 1 MHz. In addition, fundamental current levels in the sensors of FIGS. 6 and 7 may be in 1 pico-Amp to 1-nano-Amp range, and sampling circuits must be designed to support these low currents as well. In some preferred embodiments, the pixels must be able to accumulate current/voltage signal for a substantial fraction of the time. That is, they cannot be overly "shuttered" and potentially miss real-time signal features. Preferably, they collect current-based data for at least 50% of the time, and preferably for at least 80% of the time, and in some applications, over 95% of the time, to avoid missing key aspects of real-time signals. Various embodiments may provide for pixels that collect and hold information nearly 100% of the time. The basic circuits must be specially designed to support these requirements.

In various aspects, sensor pixel design for such a chip is based on the primary sensor, such as in FIGS. 6 and 7, through the following series of circuit architecture constructions and extensions that enable embodiment of as a sensor pixel in such a chip, and also enable use of CMOS processes for such chip fabrication, i.e. adhering to the limited range of circuit elements that can be efficiently fabricated by such processes.

Figure 15:
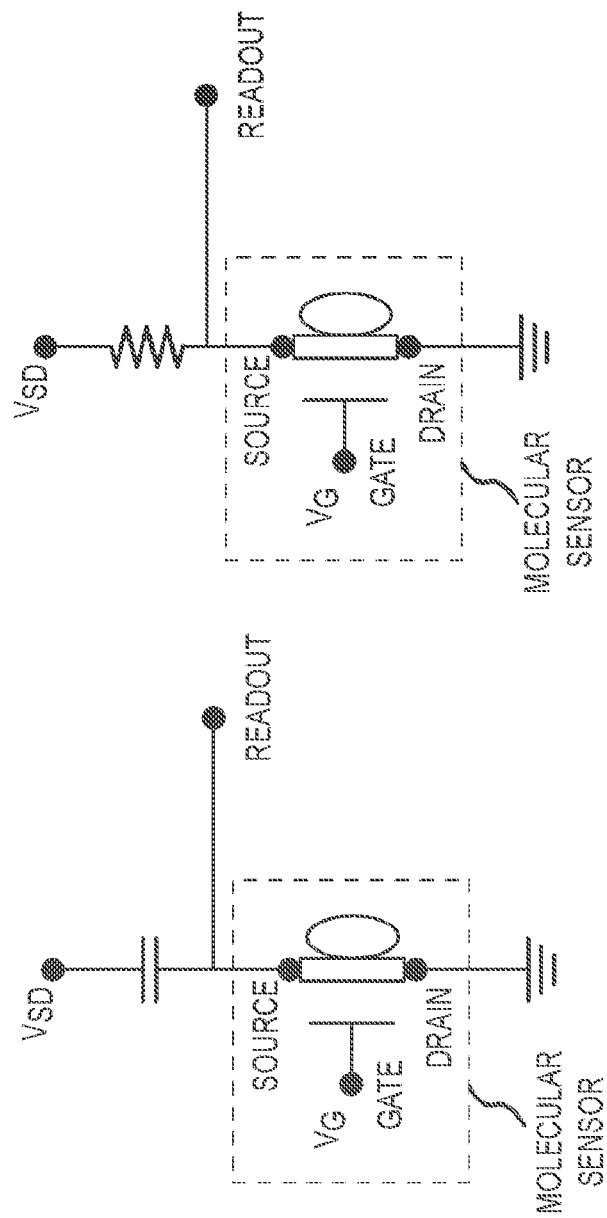
FIG. 15 illustrates embodiments of basic sensor measuring circuits.

For deployment as a sensor array, the basic sensor devices such as indicated in FIGS. 4, 5, 6, and 7, must be embedded in a basic measurement circuit, with a readout voltage accessible by a readout line. FIG. 15 illustrates two embodiments of basic sensor measuring circuits. The sensor element, in certain embodiments, is embedded in basic measuring circuits that define an output voltage relative to a current collection capacitor, or a voltage-dividing resistor. Such basic architectures are augmented with additional circuitry to support the array architecture, as well as enhance the quality and signal-to-noise ratio of the measures. In the preferred embodiment, these architectures are implemented in integrated semiconductor circuits, and in particular CMOS circuits.

In one form in FIG. 15, a capacitor is added inline with the driving source-drain voltage in order to collect and transduce the sensor current into a readout voltage. In another preferred form, a resistor is instead put inline in order to convert sensor current to a voltage for readout. In order to be compatible with CMOS semiconductor fabrication, such capacitive or resistive elements may be implemented as is standard for such elements in CMOS, using transistors or junctions between differently doped regions. For example, the resistor shown could be implemented as a transistor, as could the capacitor, in accord with standard practices of translating common abstract circuit elements into integrated circuits and CMOS devices. In addition, the parameters of the capacitor or resistor must be chosen for compatibility with the voltage and current levels required for such devices in various applications. These parameters include voltages such as in the range of 0.1 to 10 Volts, and currents in the range of 1 pico-Amp to 1 nano-Amp. In some cases, current levels can be as low as 1 femto-Amp. Readout frequencies, which are typically in the range of 0.1 kHz to 100 kHz, also determine the requirements for the capacitive and resistive elements.

The basic measurement circuits are preferably embedded in circuits that have the functionality required to perform as a pixel in a sensor array. Such pixels are to be coupled into an array of conductive lines for output of the measurement voltages, as well as well as conductive control lines that determine which pixel voltages are being read out through the limited number of output lines, as well as potentially controlling the resetting the measurement circuits between readout events.

Figure 16:
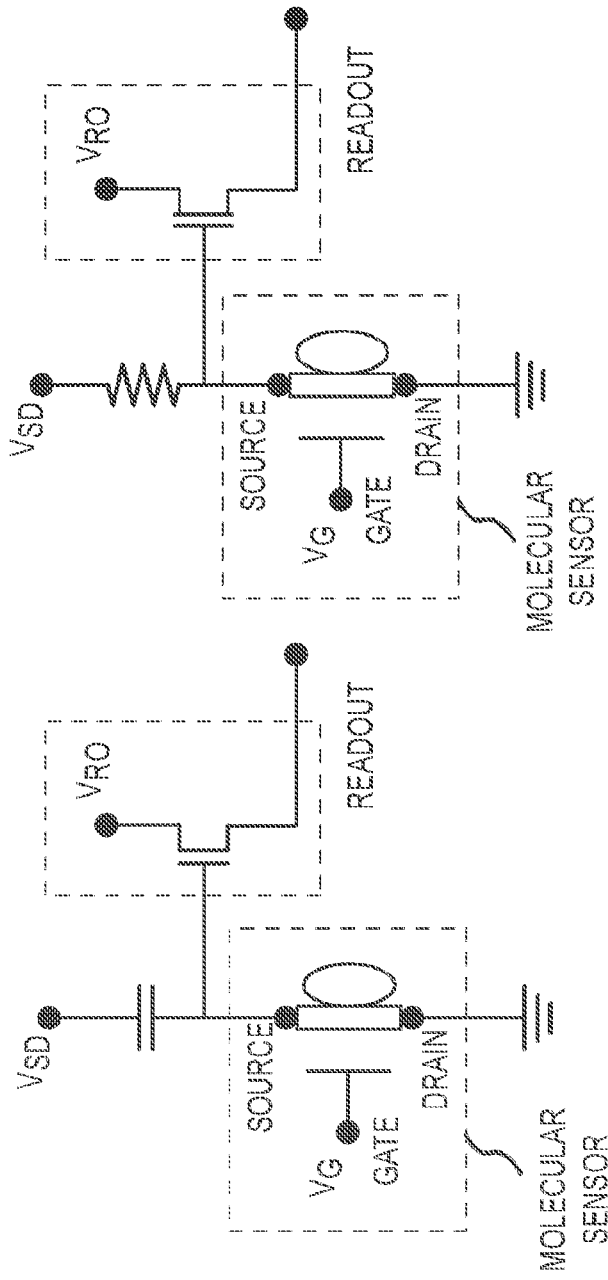
FIG. 16 illustrates the addition of a readout switch to the basic measuring circuit embodiment of FIG. 15.

FIG. 16 illustrates the addition of a readout switch (transistor) to the basic measuring circuits in FIG. 15, in order to isolate the measuring circuitry from the output (readout) lines, and thereby improve signal quality.

Figure 17:
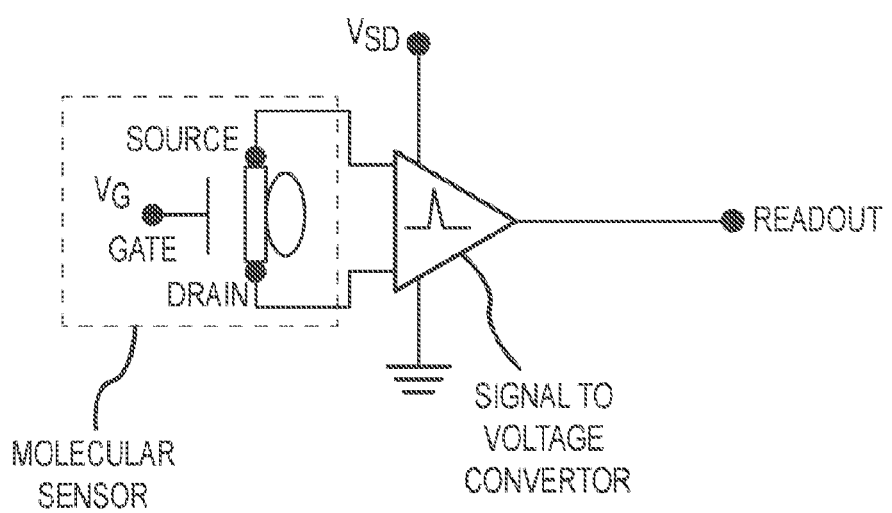
FIG. 17 illustrates a representation of sensor circuitry for a sensor pixel.

FIG. 17 illustrates a representation of sensor circuitry for a sensor pixel. This illustration encapsulates the details of the local molecular sensor circuitry to facilitate understanding of how such sensor pixels are integrated into an array circuit architecture. Here, the basic sensor pixel has a readout line and a powering voltage that drives the measurement circuit. The general transducing element in the array circuitry of FIG. 16 can be described using the signal to voltage convertor symbol, as used in FIG. 17, which is understood to represent either of such specific measurement circuits, as well as other circuitry that may be added to achieve such transduction. Other circuitry to achieve transduction include, but are not limited to, additional transistor or diode circuits or semiconductor process features, such as p-n junction diodes or barriers, or other desirable changes in doping or strain, and the like, which improve signal to noise ratios. All such techniques are embodiments within this general circuit symbol, for describing the array circuit architecture more simply and efficiently.

Figure 18:
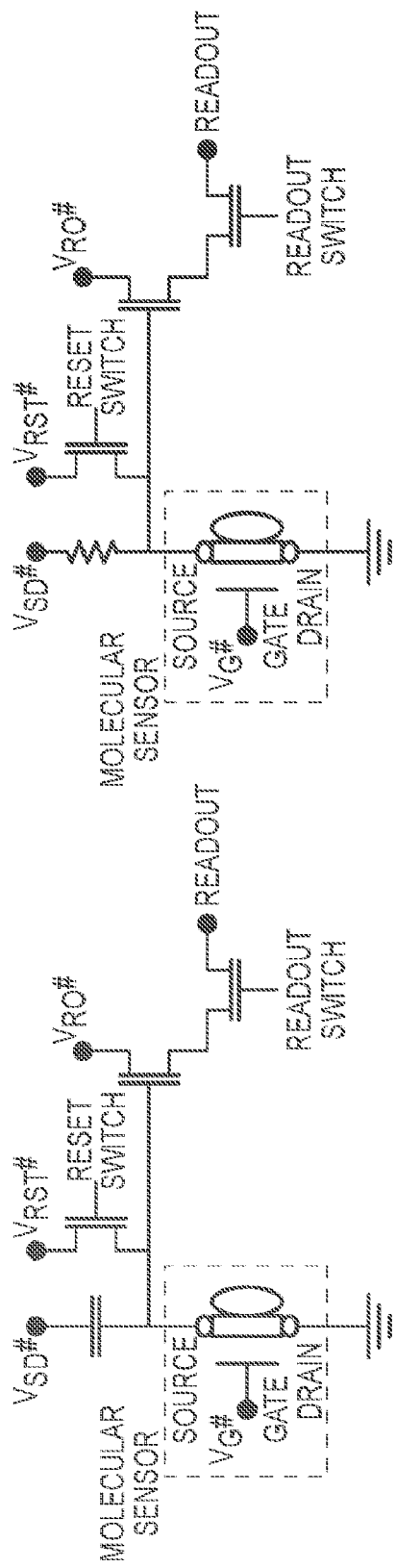
FIG. 18 illustrates additional exemplary local circuit details.

FIG. 18 illustrates examples of additional local circuit details. These particular embodiments further enhance the performance of the local sensor circuitry of FIGS. 15 and 16, with the addition of a reset switch/transistor used to set a defined initial voltage prior to making a voltage measurement. Such a reset switch, when activated, will reset the voltage at the measurement point to a known reference level by releasing any stored charge as needed. This provides a known reference state, improving the ability to identify or subtract noise or voltage drift from the measured signal values.

Figure 19:
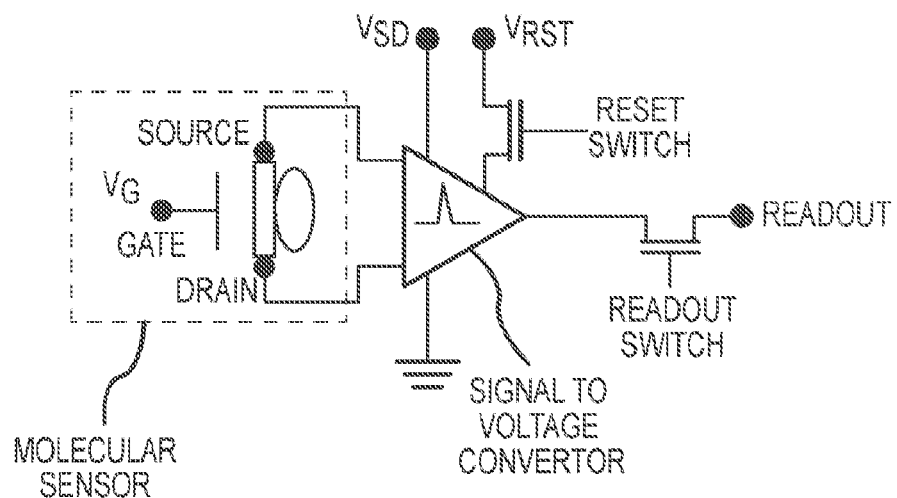
FIG. 19 illustrates an embodiment of sensor circuitry for a sensor pixel.

FIG. 19 illustrates a representation of sensor circuitry for a sensor pixel. This illustration encapsulates the details of the local sensor circuitry exemplified in FIG. 17, but teaches that in certain embodiments the sensor pixel has a reset switch and a readout switch, as well as a voltage that drives the pixel operation. For the purpose of describing the pixel array architecture, the array circuitry, such as exemplified in FIG. 19, can be simultaneously described using a signal-transducing element of the form indicated in FIG. 17, which is understood to represent either of such specific measurement circuits.

Figure 20:
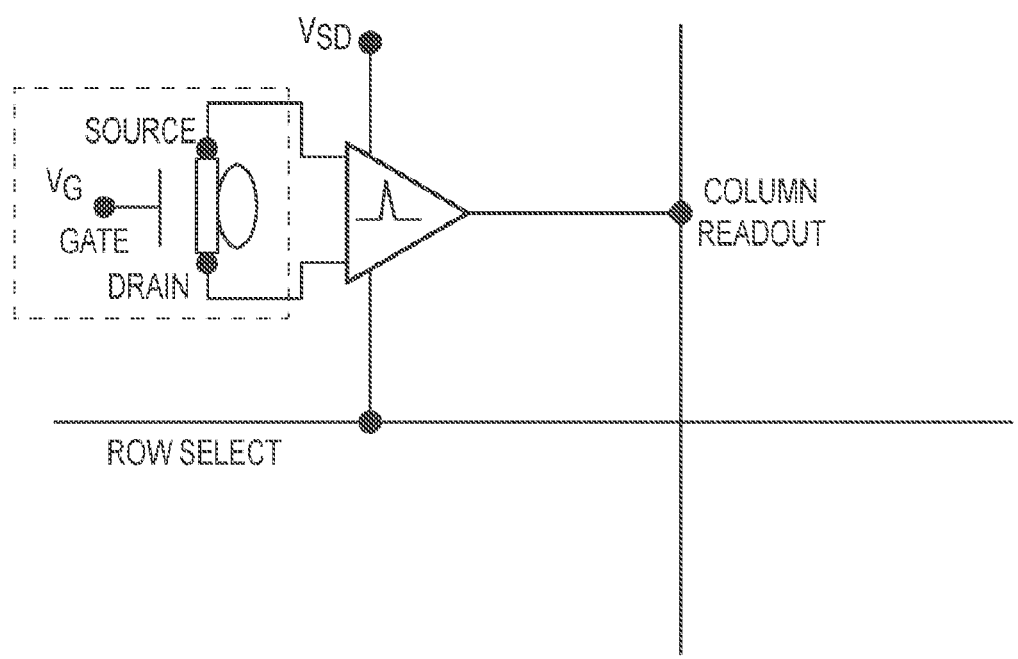
FIG. 20 illustrates an exemplary basic array architecture for a sensor pixel.

FIG. 20 illustrates an example of basic array architecture for a sensor pixel. In this case, the basic pixel is integrated with the row select line energizing the pixel, and a column readout line that acquires the output voltage. In this embodiment, a signal on the row select line will energize the pixel measurement circuit, resulting in a valid measurement signal appearing on the readout line for that pixel column, thereby presenting the readout signal from that pixel on the line. This embodiment minimizes the number of transistors required to achieve an arrayed sensor pixel, which favors the ability to have more sensors per unit of area on a chip. The total number of transistors per pixel generally will limit how many sensors can possible be fabricated on a given chip area, since there are space limits and transistor size limits, based on the relevant design rules for the fabrication or process under consideration. Thus, in some embodiments, minimizing the transistor count per pixel is an important circuit design goal, and is generally an important consideration in design in order to achieve maximum pixel-count scaling for a particular array architecture.

Figure 21:
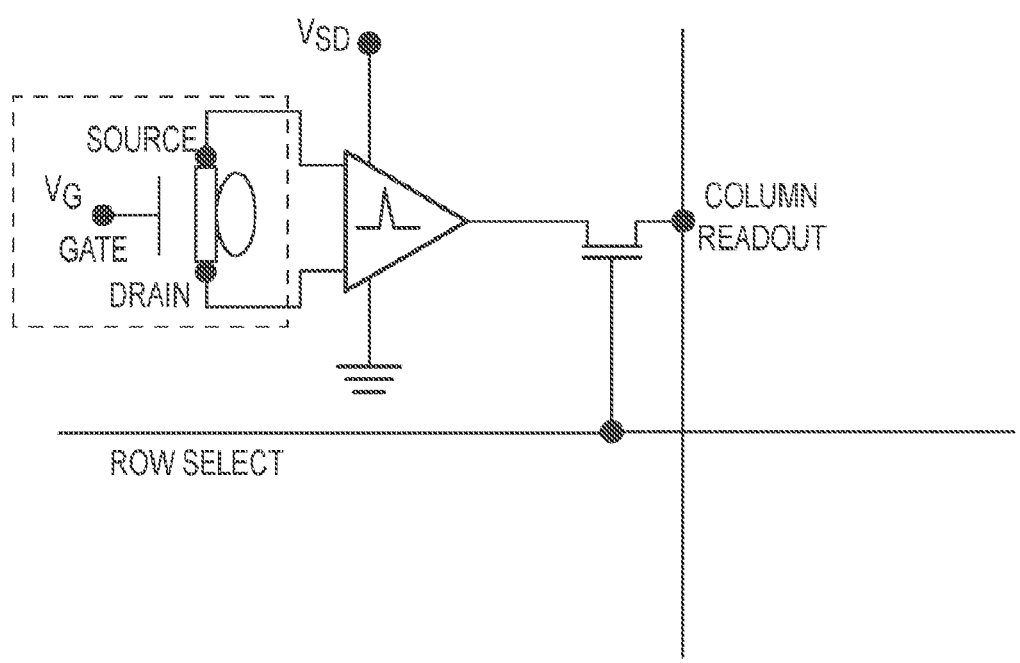
FIG. 21 illustrates a further preferred basic array architecture for a sensor pixel.

FIG. 21 illustrates additional exemplary basic array architecture for a sensor pixel. This configuration extends the architecture exemplified in FIG. 20 by wiring the row select to control the readout, providing sensor isolation when not being selected for reading. This approach to coupling the above sensor pixel devices into a pixel array, where the row select line controls a switch for the column readout and the pixel is energized separately from the row select signal, is more robust. This better isolates the signal output from the measuring performance of the pixel, improving signal quality. In this embodiment, the pixel is always energized, and a signal on the row select line will flip on the switch (transistor) that presents the readout signal from that pixel to the line. In a certain embodiment this requires an additional transistor switch for each pixel sensor element in the array. This transistor count increase is not desirable, but is a tradeoff to achieve more informative signals. In various embodiments, such switch/control transistors are to be made as small as possible, at the limits of the physical design rules for the process, in order to be able to fit more sensors per unit of chip array area. In other embodiments, such switches will be designed to reduce power consumption, noise, or drift.

Figure 22:
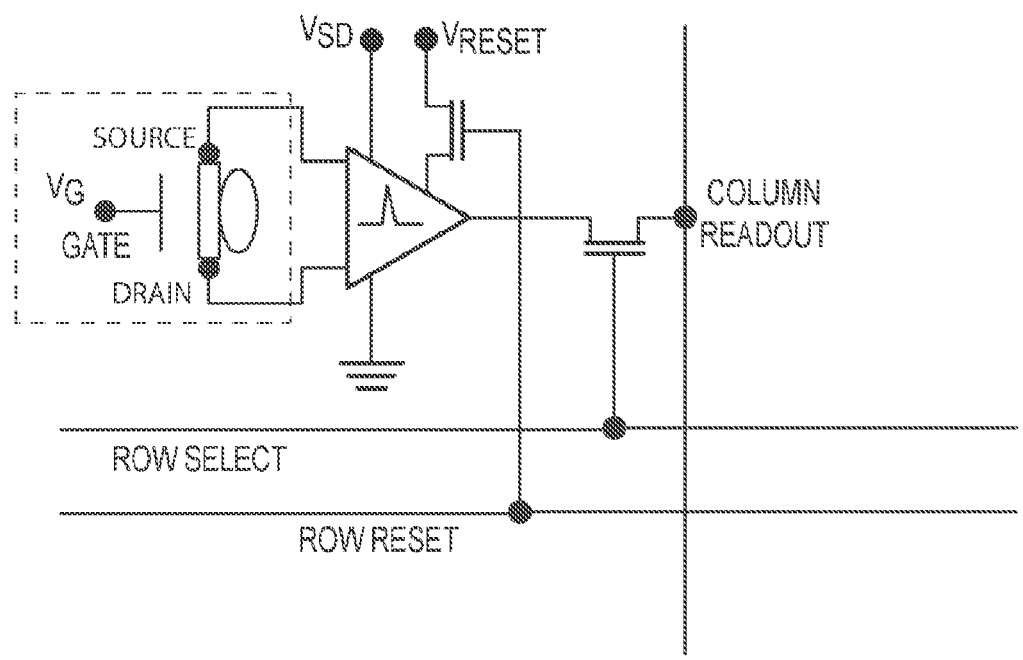
FIG. 22 illustrates another preferred basic array architecture for a sensor pixel that extends the exemplary architecture of FIG. 21 by including a row reset line.

Referring now to FIG. 22, an embodiment of a basic array architecture for a sensor pixel is illustrated. This configuration extends the architecture of FIG. 21 by including a row reset line, so that rows of pixels can be reset to a known state after reading. This is a more robust means of coupling the above sensor pixel devices into a pixel array, where there is an additional reset line along the row such that every pixel in the row can be reset after they are read out.

Figure 23:
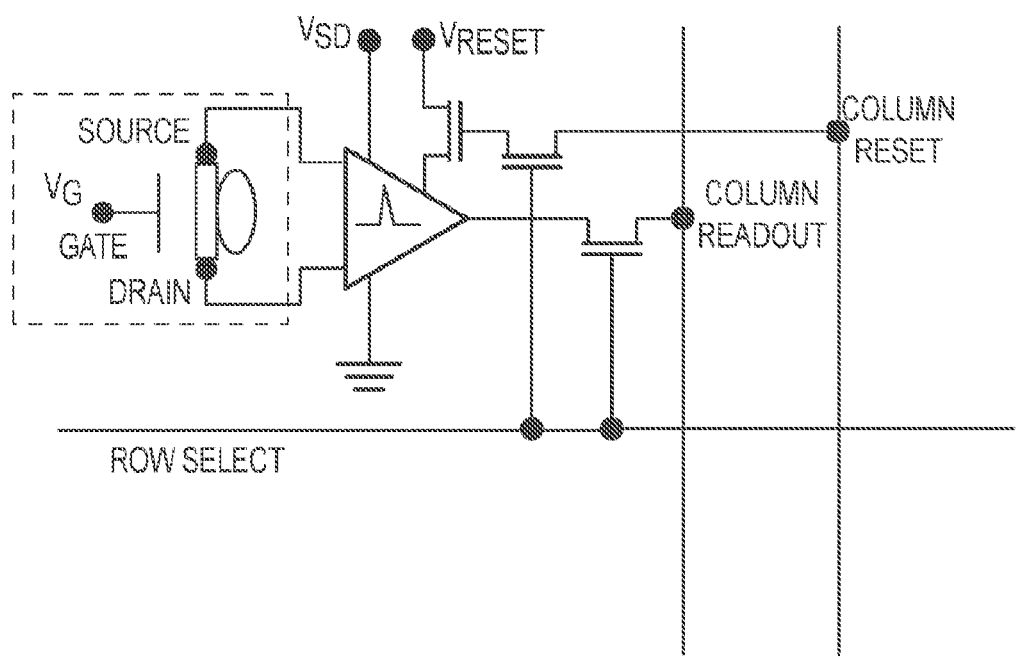
FIG. 23 illustrates another preferred basic array architecture for a sensor pixel, which is an alternative to the exemplary architecture of FIG. 22.

FIG. 23 illustrates another preferred basic array architecture for a sensor pixel, and in particular for coupling the above described sensor pixel devices into a pixel array. This embodiment comprises a column line controlling the reset, in conjunction with the row select line. This configuration allows pixels along the reading row to be resent independently, thereby allowing more flexibility in the time order of when pixels are read out and reset in the array. The configuration also allows for individually addressable pixels.

Figure 24:
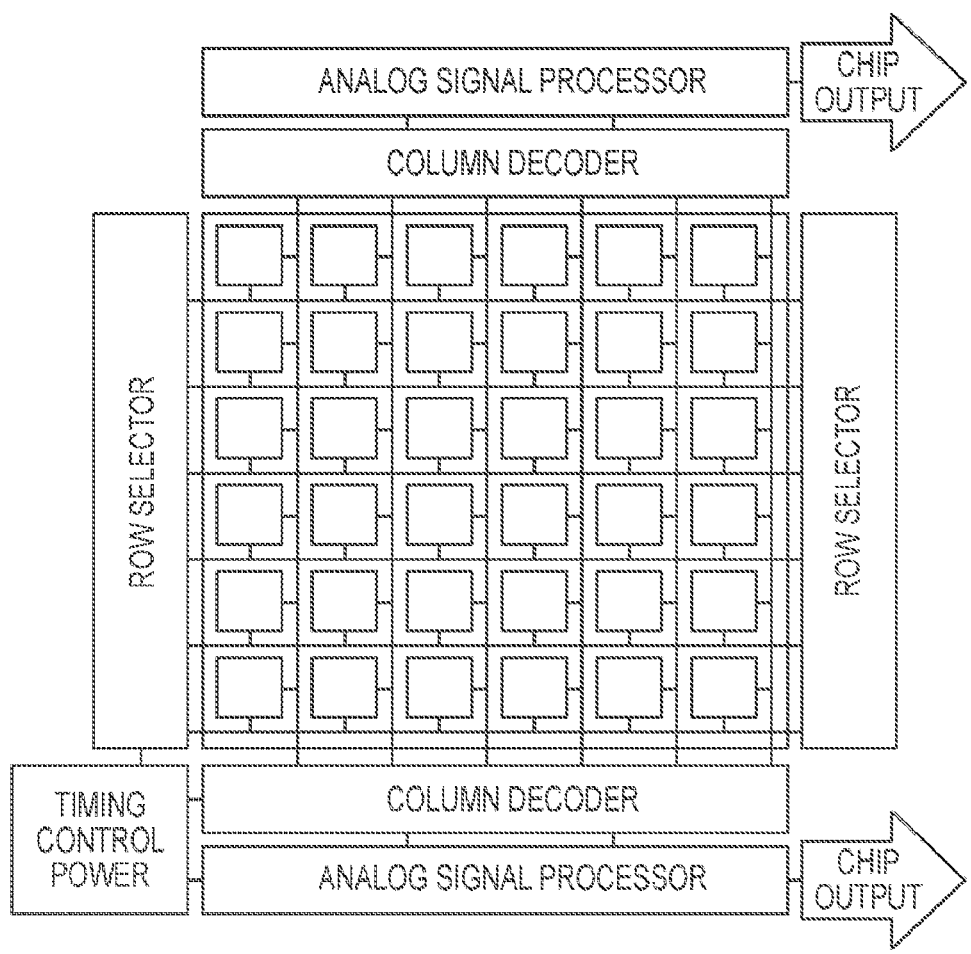
FIG. 24 illustrates an embodiment of overall chip architecture for a sensor pixel array.

FIG. 24 illustrates an overall chip architecture for a sensor pixel array and how the array of row select lines and column readout lines (e.g. the local pixel connections indicated in FIGS. 20-23) are related to the higher level chip architecture. These high level architectural elements are similar to those used in CMOS imager sensor arrays. Here, major functional blocks control the row selection and readout process. Further, there are blocks for timing, control logic, power, and other common chip functions. In this particular embodiment, row lines do not intersect with the column lines in the circuit architecture.

In other embodiments, there can be additional control lines implemented in other layers of the CMOS chip, such as those that could supply the sensors with specific reference voltages, as well as the appropriate lines and logic to control access to these. This additional architecture can play a role in sensor chip performance or control, or can support the voltage-related processing required for directed molecular self-assembly of the sensors. Further, various nano-fabrication techniques may require a voltage applied to the nano-electrodes, such as to direct nanoscale electrodeposition of materials in a voltage-directed fashion, and this additional architecture can assist here as well. Thus, seeing these advantages, CMOS chips often have up to 10 or more layers of line layouts supporting such chip-wide needs, and this will be the preferred means of achieving array-wide needs for the sensor array chips as well.

Figure 25:
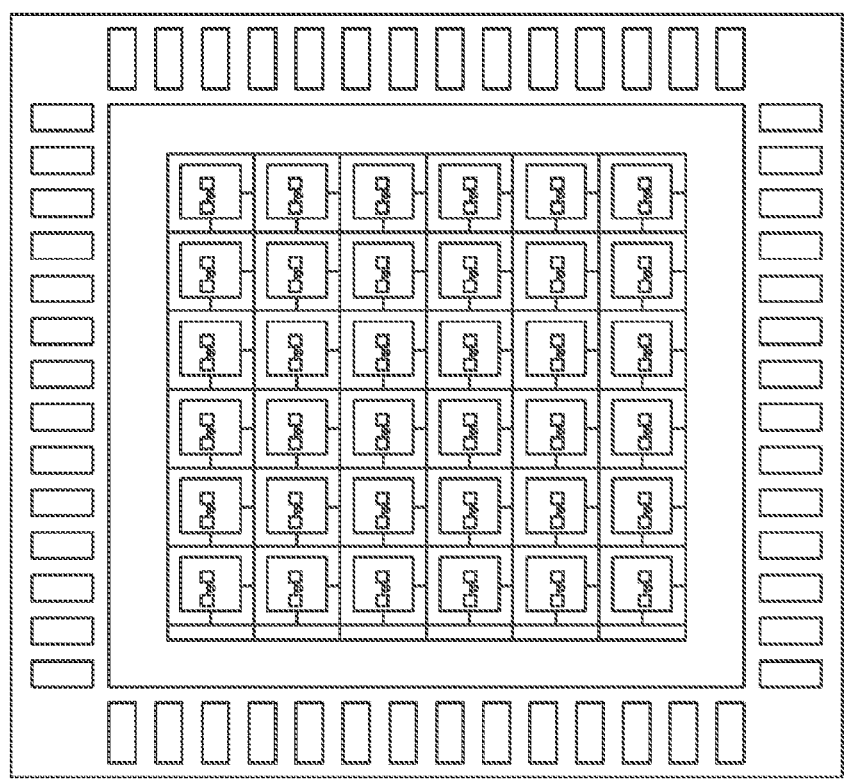
FIG. 25 illustrates an embodiment of a packaged sensor array chip.

FIG. 25 illustrates a packaged sensor array chip, indicating how the chip of FIG. 24 is integrated into standard packaging with data I/O pinouts, in a manner compatible with the final packaging in a flow cell. In this embodiment, the semiconductor chip is to be packaged so that it is mounted in packaging that provides an interface to pinouts for use within standard circuit boards and connectors, in order to interface with other system-level electronics for signal processing, data transfer, and storage. This facilitates integration into larger electronics processing systems, and the use of standard electronics components in such systems. The sensor array format and chip, combined with this unique class of sensor pixels, enables novel applications and methods for characterizing an analyte or analytes. The following now addresses these array-based methods and applications.

Massively Parallel Sequencing Methods

Figure 26:
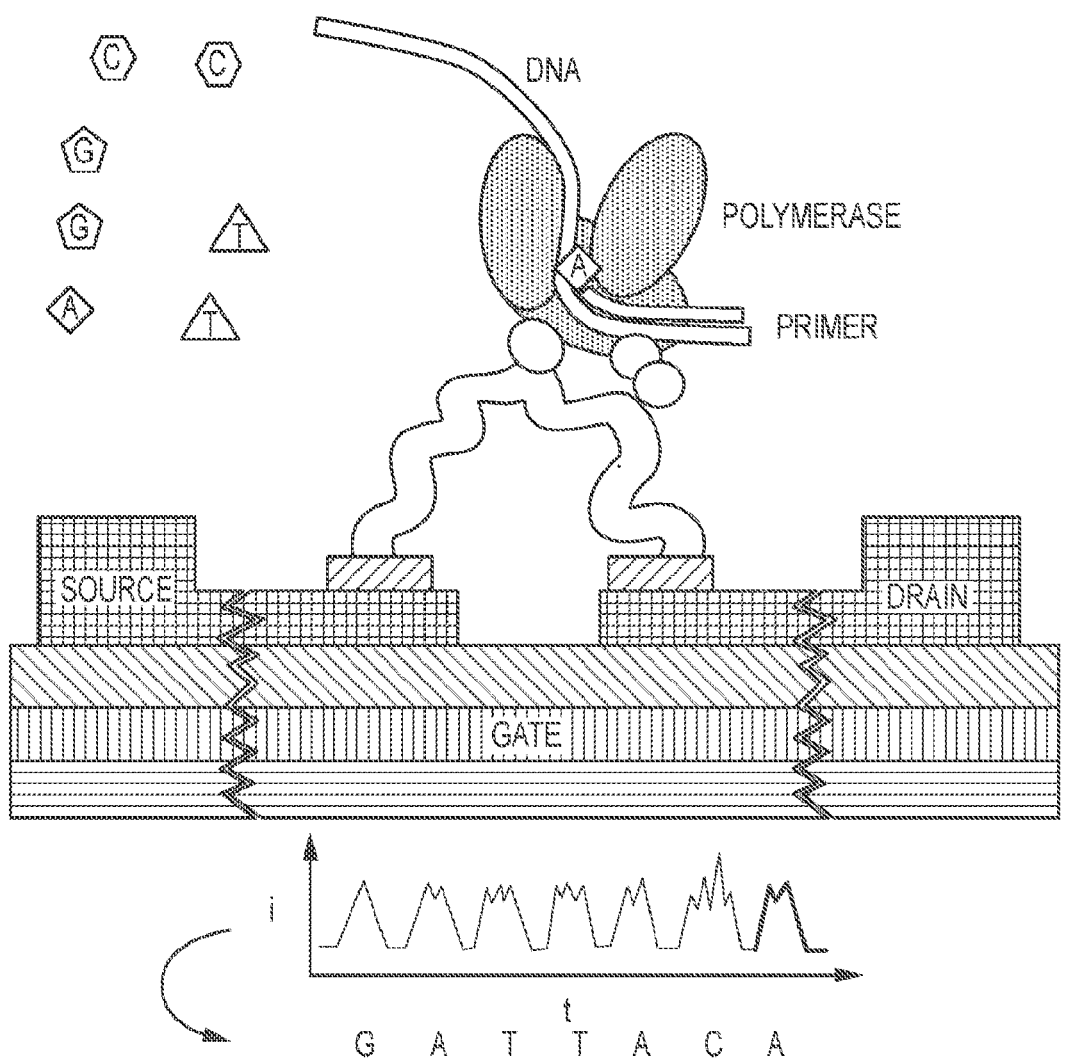
FIG. 26 illustrates one preferred embodiment of DNA sequencing, wherein the probe comprises a polymerase enzyme.

In a particular embodiment for DNA sequencing, shown in FIG. 26, the probe comprises a polymerase enzyme, bound to a template DNA molecule that has a single-stranded portion suitably primed for synthesis of a complementary strand, and the interaction target is the substrate for the enzyme-DNA complex. The extension of the primed single stranded DNA template is fed by nucleotide-triphosphates (dNTPs) in a suitable buffer. The incorporation process illustrated is incorporation of the nucleotide A, producing a corresponding identifiable feature in the measured current trace. In the interaction here, the dNTPs are polymerized, or incorporated, into the growing complementary strand. The sensor signals here may identify the base incorporation events as signal spikes, and can also distinguish which base is incorporated as well, and such signals can, in turn, provide the basis for various sequencing chemistries that determine the DNA sequence. In the embodiment set forth in FIG. 26, the signals fully distinguish among the different the bases, and thus the sequence of bases of the DNA fragment can be deduced. This can be performed in a massively parallel form on such a chip, with a different DNA molecule being read at each site, and this provides the basis for making a massively parallel DNA sequencing system, when combined with the system level processing indicated in FIGS. 9 and 10. The chip based sensor array provides a new level of economy and manufacturability to this process, beyond that afforded by the isolated sensors, or less integrated assemblages of sensors. A similar method is accomplished for RNA sequencing by using an RNA polymerase enzyme as the probe rather than a DNA polymerase enzyme.

Terminator Sequencing

Figure 27:
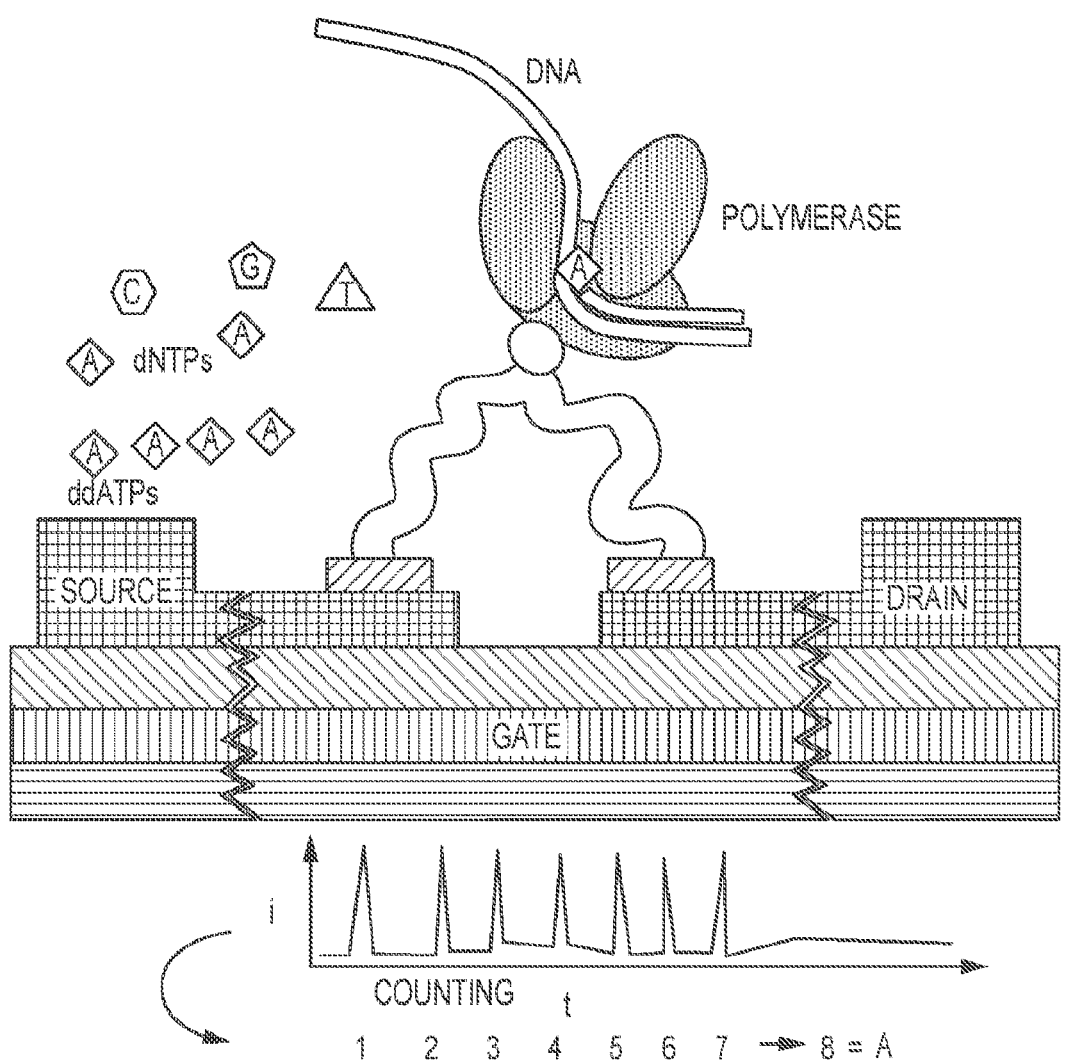
FIG. 27 illustrates a preferred embodiment of terminator sequencing, wherein only a single base terminator is used in a given reaction.
Figure 28:
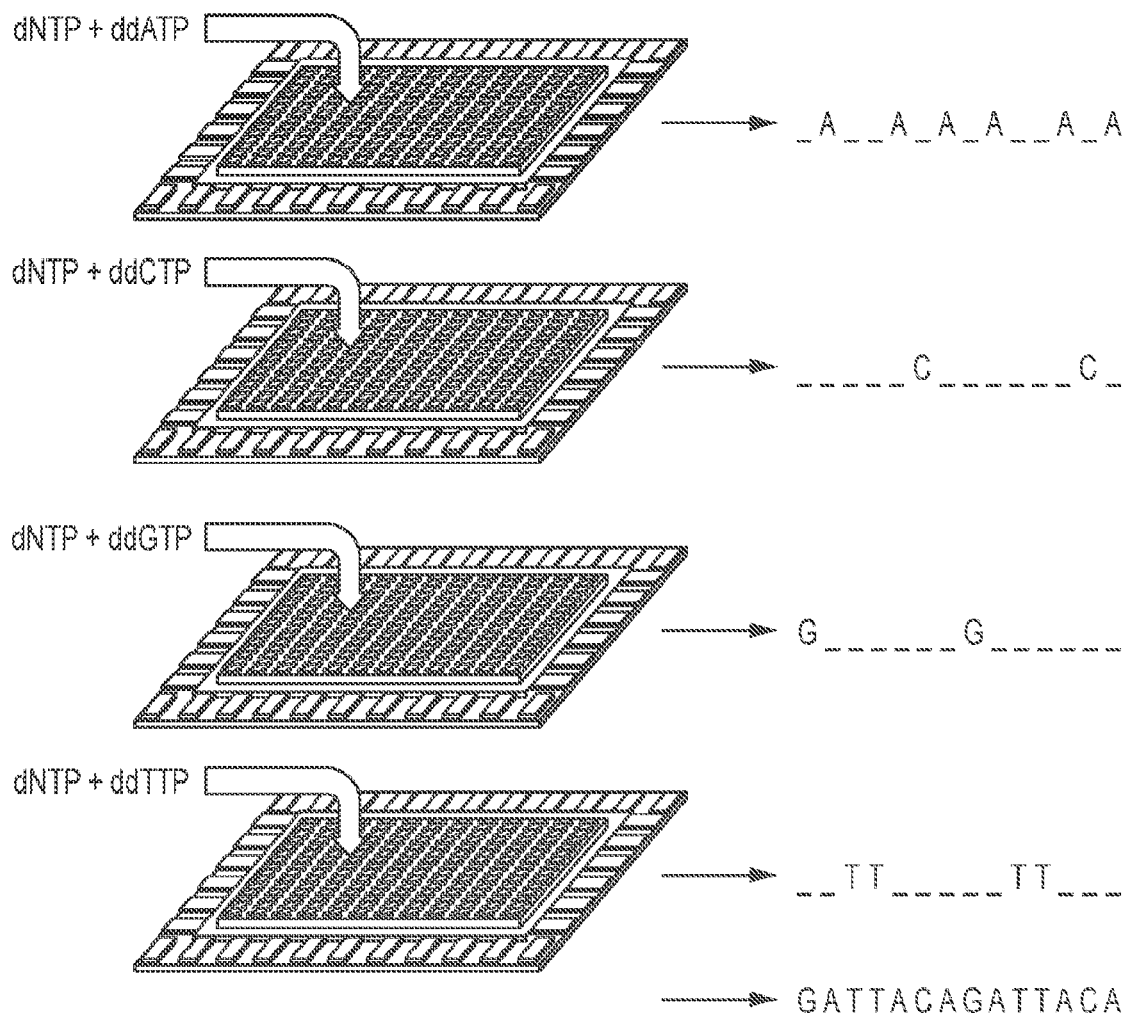
FIG. 28 illustrates a preferred embodiment of terminator sequencing, wherein a replicated template of interest is loaded into each chip indicated, and all A termination data is accumulated from one run on a parallel sensor array to determine the full sequence of the template in question.

In another embodiment for sequencing, the chip can be used to perform efficient terminator sequencing, as indicated in FIGS. 27 and 28. FIG. 27 illustrates an embodiment of terminator sequencing where only a single base terminator, a di-deoxy adenosine triphosphate termination (ddATP), is used in a given reaction. In this mode, when the reaction terminates, it is implied that the base in question is A, the terminator, and the count of the number of incorporation spikes gives the position of this A in the template. Repeating many runs for A with replicate templates will randomly determine all A locations in the template, and performing similar series of runs for the other terminator bases C, G, T, respectively, will determine the respective locations of all these bases in the template, thereby determining the entire sequence. In the sequencing embodied in FIG. 27, it is assumed that each individual incorporation event is present in the signal as a discrete spike or feature. As shown there, the primed configuration is exposed to a solution that contains a mixture of all 4 base dNTPs, plus (for the base to be specifically interrogated, e.g. A) the specific corresponding di-deoxy terminator, (e.g., in this case, ddATP). Upon exposure to this solution, spikes of incorporation will result until such a point a ddATP terminator is incorporated, after which point the incorporation spikes cease. The terminator base characteristically may or may not produce a typical spike. FIG. 27 embodies the case where it characteristically does not. The resulting count of such normal incorporation spikes determines base position at which the terminator A was located. In a given realization of this, said location will have been selected at random among all the A incorporation locations possible along the template, dependent on the random event of whether the ddATP versus dATP is incorporated at any such site. When this reaction is performed on a sensor chip array loaded with replicated templates, a randomly sampled set of locations of said base in the template will be obtained in massively parallel fashion, from the sensor array output signal trains of all array pixels, and with high statistical confidence this will cover all locations of said A base in the template, as long as sufficiently many reads are obtained from the chip sensors. This will be the case if the sensor array contains substantially more sensors than the length of the DNA template, and if the appropriate proportions of terminator nucleotides are used such that terminated fragments of all lengths are expected to be generated in multiple numbers in the overall experimental run. Thus one such chip run will reliably determine the location of all A bases in the fragment. Running other chips for the other bases will therefore provide the information to determine the entire sequence.

FIG. 28 illustrates a further embodiment of terminator sequencing, where the 4 separate reactions are run, one for each of A, C, G, and T such that full terminator sequencing of a fragment is achieved through processing the data from four single chip runs. In this case, a replicated template of interest is loaded into each chip indicated, and all A termination data is accumulated from one run on a parallel sensor array, as indicated in the top series of FIG. 28, and similarly for the C-, G-, and T-termination reactions, and the single base results from each are accumulated (at the bottom of FIG. 28) to determine the full sequence of the template in question.

In the context of a complete sensor system, such as indicated in FIG. 9, the system may comprise four (4) chips on the motherboard, and these four chips may be introduced through the solutions of the liquid processing system as indicated in FIG. 28. Such a system that supports data processing from the 4 chips. Each chip, once fully established with primed templates, requires just a single solution of dNTP and ddXTP, wherein X is the respective base to be interrogated, (out of A, C, G, T). Data are collected and processed from each chip, and then combined to determine the underlying sequencing. In some cases, only a most likely underlying sequence is determined based on the observed data, such as when there is noise of any kind confounding the signal analysis.

Determination of the Number of Sensors Required

The number of sensors required is a function of the fragment length and mix of terminators to non-terminators. As an example, if the template length is L=100 bases, and this template is supplied in replicate to Ns=10,000 sensors in an array, and the ddATP to dNTP ratio in solution is such that the probability of a ddATP being incorporated at any given A is f=1% (ideally, f=concentration of ddATP relative to concentration of dATP, ignoring incorporation biases), then the expected number of reads that would inform on an A at a particular location i in the template, N[A, i], based on elementary statistics, is given approximately as:

$$N[A,i]=Ns\, f\, \mathrm{Exp}[-m[A,i]f],$$

wherein, m[A,i] is the number of non-A bases occurring before the position i in the template. This number of expected reads of A at location i is smallest at the end of the sequence, i=L, and assuming a typical sequence composition where ~3/4 of all bases are non-A's, then is approximately, (with some minor re-writing):

$$N[A,L]=(Ns/L)(Lf\mathrm{Exp}[-(3/4)(Lf)]).$$

The latter part of this expression, u Exp[−C u], u=L f, C=(3/4), is a quantity that is on the order of 1, and is maximized if u=1/C, with maximum value Exp[−1]/C, or L f=4/3, such that (4/3) Exp[−1]=0.50 here, in which case, at this optimal concentration of terminators, f=(4/3) 1/L= 1.3/L, =1.3% in this example, the expected number of observation of A near end of the template is:

$$N[A,L]0.5\times(Ns/L).$$

Since it is needed that N[A,L]>>1, then Ns>>L, i.e. the number of sensors is much bigger than the length of the template DNA being sequenced. Quantitatively, if it is desirable to observe each A location an expected 10 times, then it is needed that:

$$Ns\sim 20\times L$$

Or, for L=100 base fragment, Ns=2,000 sensors to get expectation of at least 10 observations of every A location in the fragment, especially those at the end. Thus, to perform, for example the sensor chip version of the original PhiX genome sequencing performed by Sanger (on slab gel) in introducing classical terminator sequencing, since that is a DNA template with 5,386 bases, it would take a Ns~110,000 sensor array. The concentration of terminators used in this case would be approximately f=(4/3) 1/5386=0.00025 (or 0.025%).

Further note from this detailed analysis that the length of the template that can be sequenced this way is limited mainly by the number of sensors, whereas classical Sanger sequencing is limited foremost by the fragment size resolution limits of gel separation systems. For example, long range PCR can produce replicate templates up to 50 kb in length, L=50,000, and these could be read with a 1 Million sensor array, in under 1 hour given the processing speeds of the polymerase, as long as it does not tend to release the template prior to traversing its full length. Such fragments could not be read by the classical terminator sequencing process. In another preferred embodiment, long fragments can also be read in this chip methodology by using multiple priming sites in respectively different chip reactions, given that all the reading is relative to the initial priming site used to prime the sensor polymerases on the chip.

In a further embodiment, multiple primers that uniquely correspond to different DNA fragments of tracts to be interrogated are used, which distinguish by some detectable signal or signature from the primer. This enables each sensor to identify the specific local primer present, and thereby also which DNA sequence tract is being interrogated. Such primers can be therefore be multiplexed into a single reaction. In particular, in one preferred embodiment, long fragments can be interrogated in parallel using multiple primers along the fragment. In another embodiment, a pool of multiple replicate fragments, amplified by a pool of respective primers, can be interrogated and deconvoluted in accordance to the primer identification teaching. Thus, such a method can be used for multiplex sequencing of panels of PCR products, presented as a pooled DNA mixture, and amplified with an associated primer pool. This in particular enables the possibility of an assay that consists of multiplex capture (by PCR or otherwise) of a set of fragments, followed by multiplex terminator sequencing on a chip, using just 4 one chip reactions such as indicated in FIG. 28. In other embodiments, the primers may contain a detectable label that assists in determining which fragment is being sequenced at the sensor in question. In another aspect, primers may contain a tail sequence containing a combinatorial hybridization code that is decoded by a series of hybridization reactions against the sensor array with primers in place, with the hybridization results measurable and measured by the affiliated sensor. The hybridization oligos used for such a decoding process can, in some embodiments, be modified with groups that enhance their detection and differentiation in the decoding hybridization reactions. In one embodiment, such tails on the primers would be 60-mer DNA sequences, which constitute a series of 6 10-mer code words, with each word from a set of N options that rely on N highly distinguishable labels on the oligos. This provides encoding of N^6 primers, and could readily encode hundreds to millions of primers, to be decoded in just 6 hybridization reactions. Many generalizations of this are possible, based on the length of the tail and the code words, including use of error detecting or correcting codes, such as employing consistency constraints on combinations of code words ("parity bits", etc.) to improve the accuracy of decoding or reject erroneous decodings.

Massively Parallel Hybridization Assays

Figure 29:
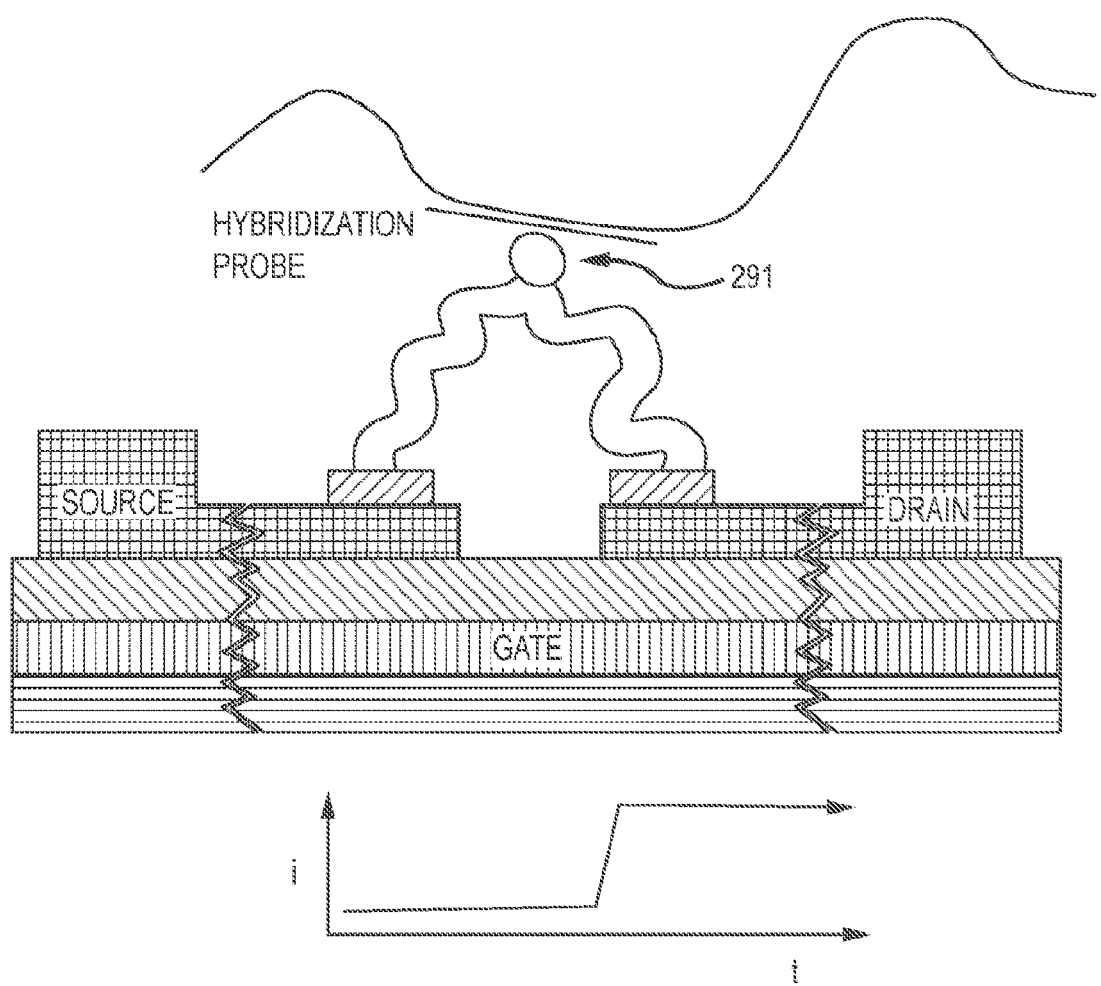
FIG. 29 illustrates an embodiment of a DNA hybridization probe usage in a molecular sensor, in place of an attached enzyme, and the detection of hybridization by monitoring a circuit parameter such as current.
Figure 30:
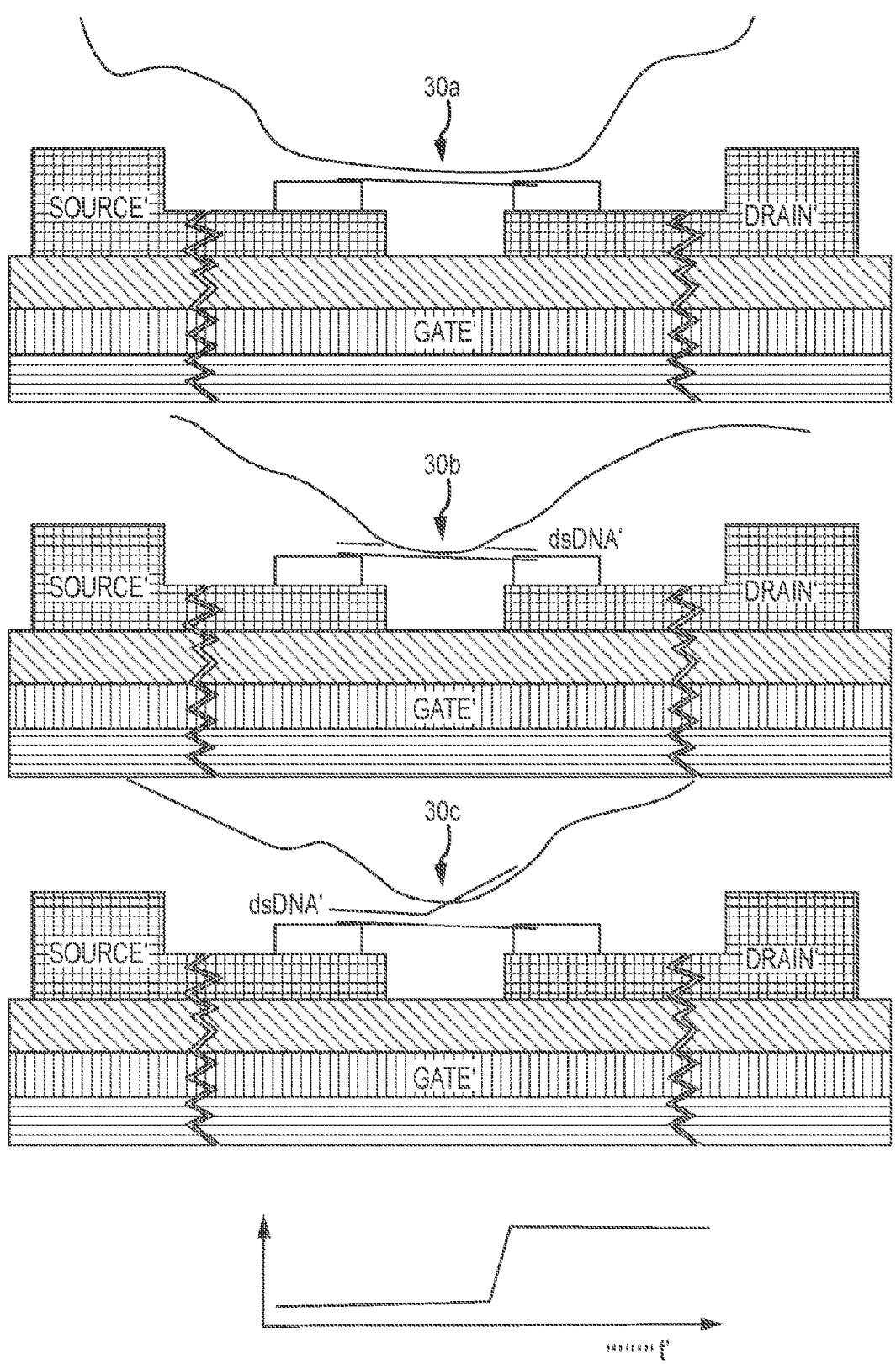
FIG. 30 illustrates various alternative embodiments of incorporating a hybridization probe into a sensor, wherein the probe forms all or part of the bridge molecule.
Figure 31:
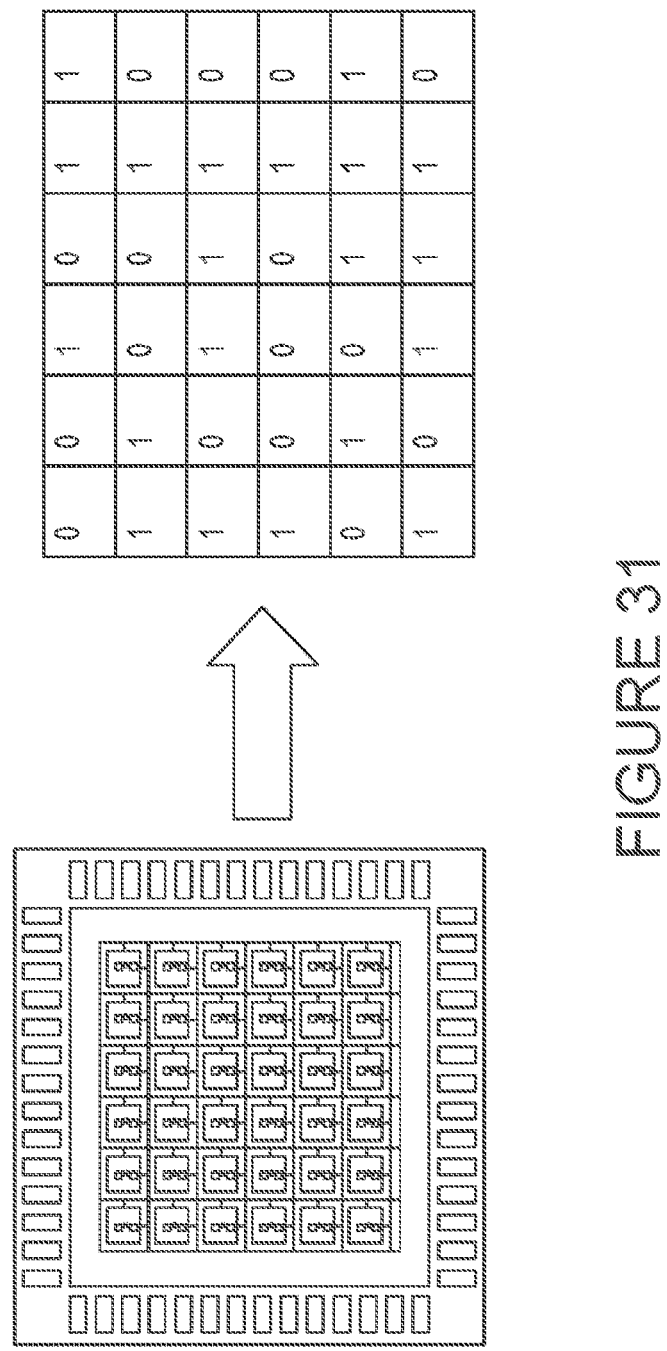
FIG. 31 illustrates an embodiment of a digital hybridization assay.

Another area of application for such a sensor array is in the area of massively parallel hybridization assays, such as indicated in FIGS. 29, 30 and 31. Such assays are historically done using DNA microarray techniques. In DNA microarrays, each probe spot, deposited on glass slide substrate, contain many copies of the same hybridization probe, and provide an analog or continuous measure of hybridization. Such spots are organized into large array layouts, and typically fluorescent imaging of labeled target material is used to obtain signals from the assay. The present invention allows for several improvements over such classical means. Instead, such assays are done in massively parallel single molecule form for digital readout of results from the individual hybridization probes incorporated, using fully electronic processing. Single molecule digital readouts can allow for rapid digital quantification of signals, through direct counting of individual hybridization events. As shown in FIGS. 29 and 30, the probe molecule for this application comprises a nucleic acid hybridization probe, typically comprising a single stranded DNA or RNA molecule (native or modified, such as nucleic mimetics LNA or PNA), available to hybridize to a complementary single strand exposed to the sensor in solution. The sensor produces a signal that indicates whether a proper hybridization event has occurred. In one preferred embodiment, the signal level can be at an expected calibrated level, indicating proper hybridization. This general assay format has applications to the same areas classically performed using DNA microarrays, including mapping of fragments in a pool against probes representing sites on a reference genome, SNP genotyping, gene expression analysis, etc. A unique valuable feature of the present embodiment is that it is single molecule, so it can deconvolute signals from a pool of mixed samples, with direct digital counting of the different singe molecule hybridization events present. This is especially relevant to SNP genotyping. This can support use in forensics, where mixed samples occur, and it is desirable to catalog all the different genotypes present, and quantify in what amounts. The electronic chip based format further uniquely enables point-of-use and portable field applications of such a system, when using portable system embodiments such as that indicated in FIG. 10.

FIG. 29 illustrates use of a DNA hybridization probe in a molecular sensor in place of an attached enzyme, and the detection of hybridization by monitoring a circuit parameter such as current. Hybridization is indicated by a different current level. One preferred embodiment is to couple the DNA hybridization probe to a streptavidin 291 via a biotinylated base located in the probe. This form of probe and detection measurement supports sequencing by hybridization, which is based on aggregating many such measures using a set of informative probes against replicated template molecules.

FIG. 30 illustrates alternative embodiments of incorporating a hybridization probe into the sensor, wherein the probe forms all or part of the bridge molecule. In one embodiment, the DNA containing the probe is coupled to the contact points using gold-thiol linkages, with gold contact points and thiolated nucleotides in the DNA. FIG. 30 illustrates three different ways such a hybridization probe can be configured, 30a, 30b, and 30c, as all or part of a DNA bridge molecule. The variation in these probes is based on the nature of the DNA bridge molecule, such as if single or double stranded DNA, as illustrated. In the lower instance, the hybridization probe 30c can further partially hybridize to the underlying DNA, to set up competitive hybridization with the target for added stringency. Detection of hybridization, versus no or imperfect hybridization, via the electronic sensor signal is indicated below.

FIG. 31 illustrates a digital hybridization assay. Each sensor provides a binary measure of whether the respective molecular hybridization probe found a proper hybridization target, based on the measured signal.

Figure 32:
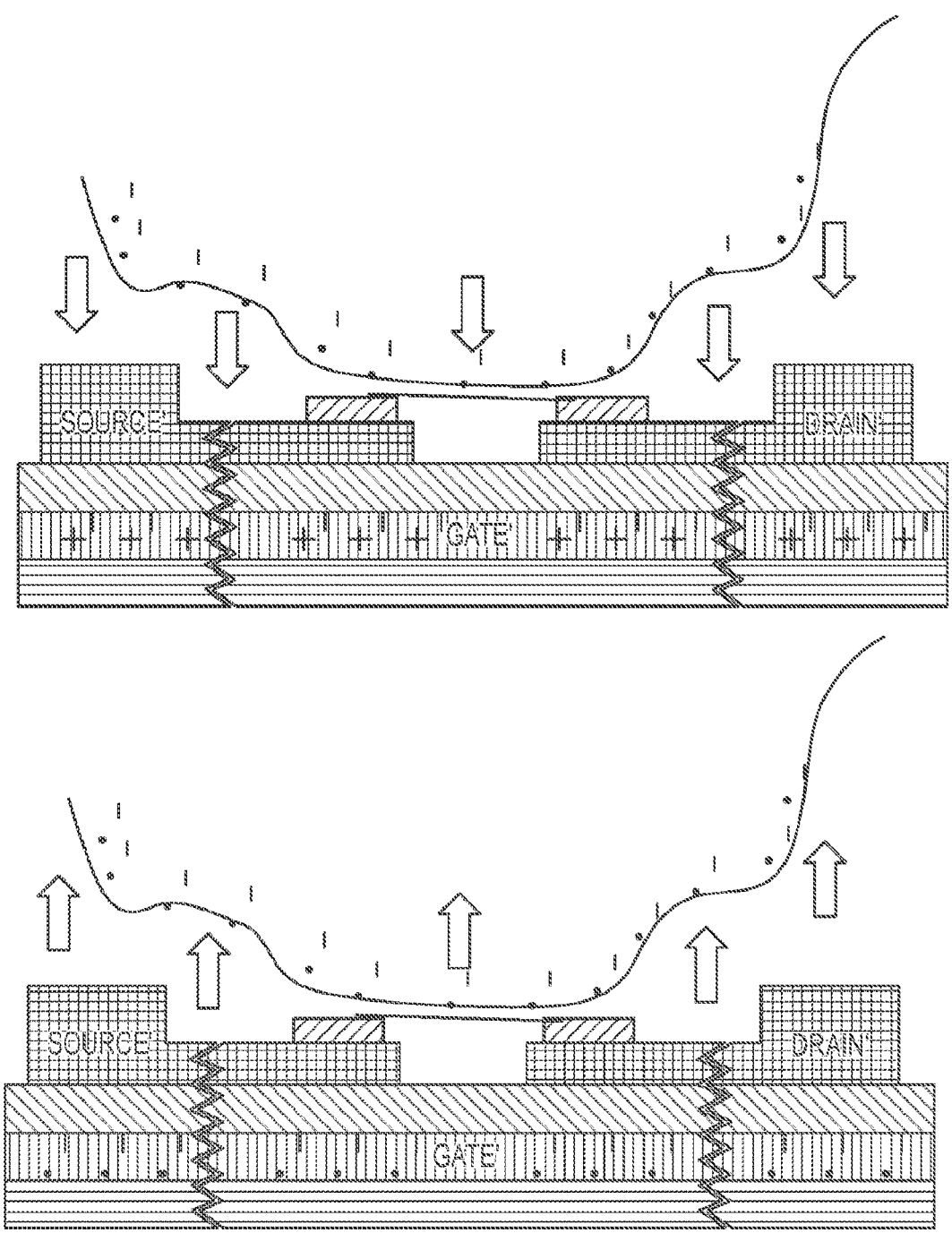
FIG. 32 illustrates an embodiment of electronic acceleration of hybridization, and electronic control over stringency of hybridization.

FIG. 32 illustrates electronic acceleration of hybridization, and electronic control over stringency of hybridization, demonstrating how the sensor voltage controls can be used in various ways to enhance the hybridization assay. One way is use of the sensor voltages, such as the gate voltage or source-drain voltage, to attract the typically negatively charged DNA or RNA targets to the sensor in solution, thereby greatly increasing the local concentration of target DNA or RNA, and increasing hybridization kinetics. This accelerates hybridization reaction kinetics and can therefore be used to both accelerate the detection reaction process, and greatly reduce the amount of target DNA that is put into the assay, since it is concentrated at the sensor sites. Also as shown in FIG. 32, reversing voltage can repel such target fragments, and this can provide a form of stringency to select against or eliminate improperly paired hybridizations (direct mismatches, improper pairing, cross-hybridization, non-specific hybridization) and select for the higher energy binding of perfectly paired hybridization. Thus, this reduces measurement error of proper versus improper hybridization. By sweeping such a voltage, a melting curve can be measured, which can further characterize the nature of the pairing, and also be used to determine the presence of mismatches. In addition, the cyclical combination of attracting and repelling DNA targets can provide for annealing, which improves the quality of final hybridization, favoring proper pairing.

Figure 33:
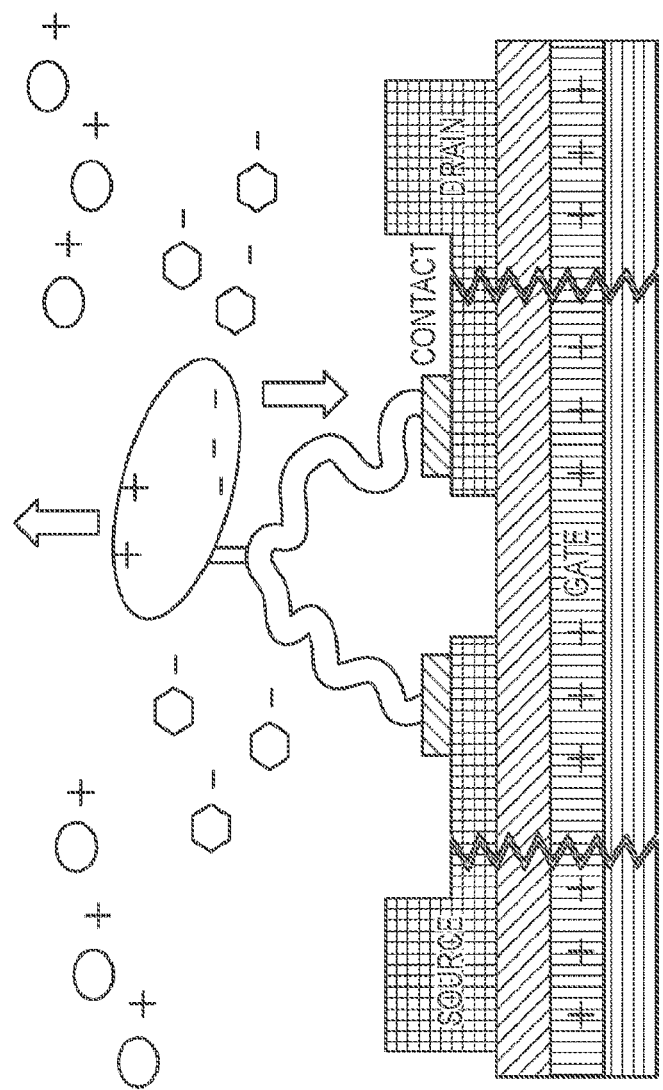
FIG. 33 illustrates an embodiment of electronic modulation of probe/enzyme configuration/function, as well as modulation of local ionic environment, including generation of local acid or base conditions to further modulate probe/enzyme function or performance.

FIG. 33 illustrates electronic modulation of probe/enzyme configuration/function, as well as modulation of local ionic environment, including generation of local acid or base conditions to further modulate probe/enzyme function or performance. Extending the concept exemplified in FIG. 32, the gate voltage, and/or source-drain voltage can be used to achieve these modulations, which may be used to accelerate reactions, alter stringency or specificity, or obtain electronic melting curves or spectroscopy, or survey the effect of different conditions across the array for operating parameter optimization The forms of voltage-directed concentration and repulsion useful for nucleic acid measurements generalizes to voltage directed or enhanced reaction processes that can be used to accelerate or improve the signals from diverse other applications. Sensor device voltages, such as the gate voltage or source drain voltage, can be used to alter the properties of the local bridge/probe molecule, to alter the local ionic environment, and to attract or repel potential interaction targets of the probe molecule. These generally can be used to accelerate reaction kinetics and increase speed of measurement, such as to improve stringency or signal to noise ratios, to provide spectroscopic measures that add a voltage-sweeping dimension to measurements and thereby acquire more data about the target molecules, and to alter the functionality or state of the probe/bridge molecule, directly or through changes in local ionic environment. Environment changes can be achieved through use of voltage-decomposable compounds, which may dissociate into useful molecular components under local voltage control, such as voltage induced acid or pH change of solution. Such means in particular could be used to clean and reset the electrodes, and to completely remove the probe/bridge molecules for device reuse purposes.

Figure 34:
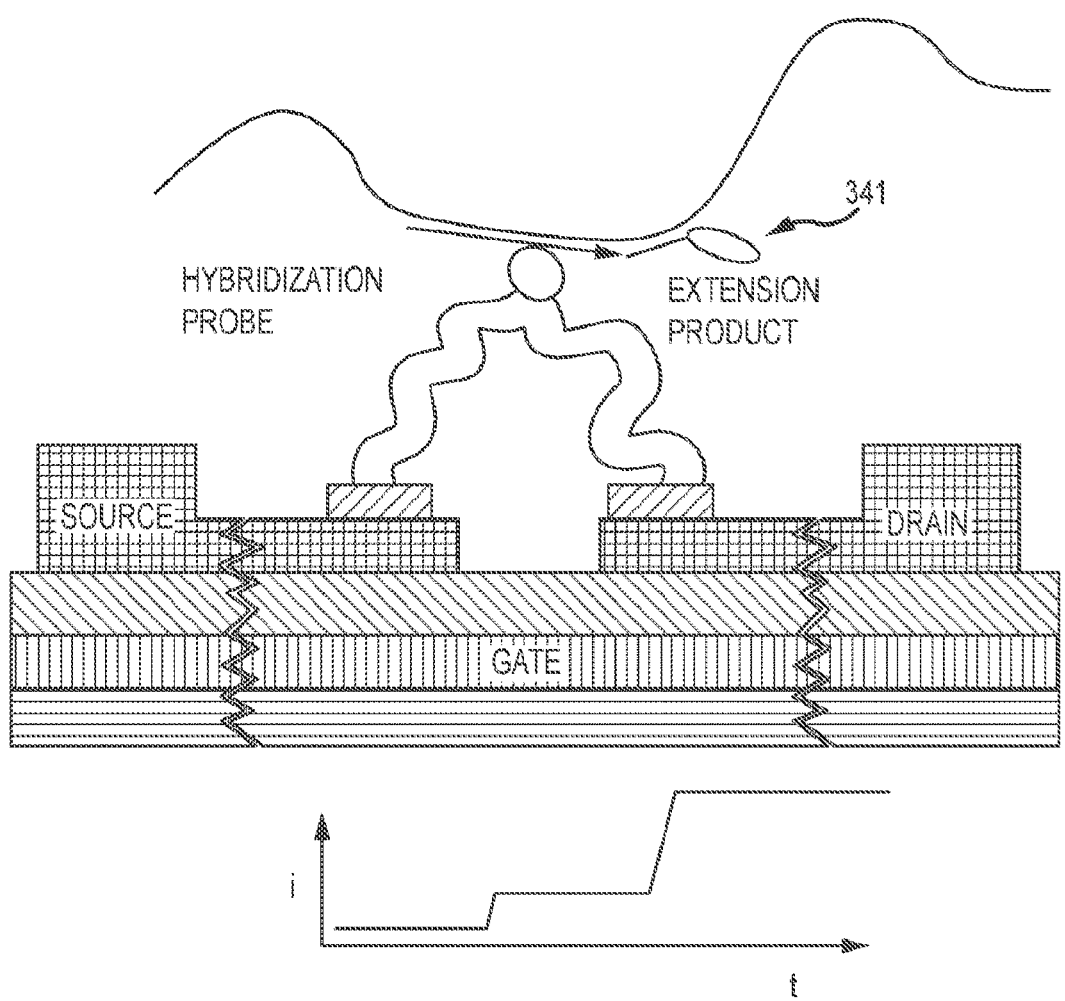
FIG. 34 illustrates an embodiment of enhancing a primary hybridization signal by using enzymatic extension (3' extendible end of the probe indicated by the directional arrow) to incorporate one or more bases, such as including detectable groups ("extension product" shown) to enhance the signal.

FIG. 34 illustrates one example of enhancing the primary hybridization signal, by using enzymatic extension (3' extendible end of the probe indicated by the directional arrow) to incorporate one or more bases, such as including detectable groups 341 to enhance the signal. Such enzymatic extension both adds stringency/checks for proper pairing as well as the means of enhancing the electronic sensor signal, as indicated by the three levels in the current plot (no hybridization, hybridization, extension product present). In the case of single base extension, if the base identity is detectable (either from the four dNTPs together or through a series of individual dNTP extension trials) it can also add one more base of sequence information, enhancing the sequencing capacity of the method. This hybridization reaction, wherein single base extension sequences, allows measuring one base of sequence after the priming site.

Figure 35:
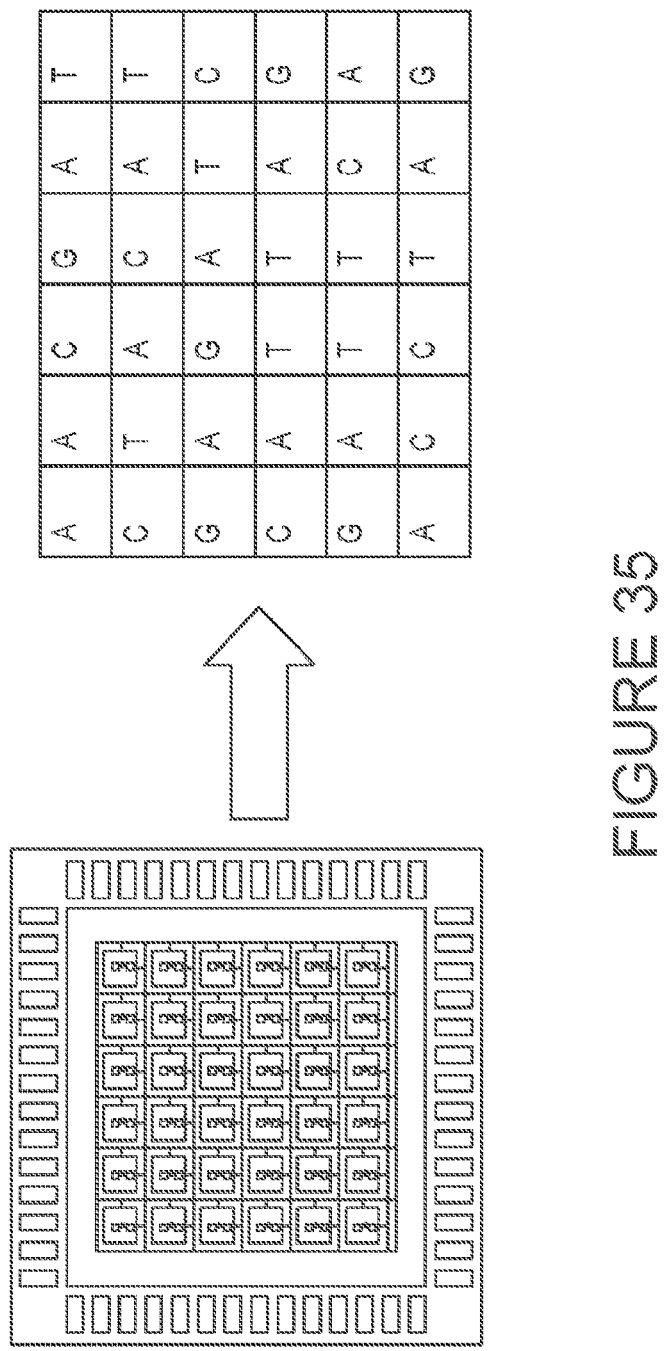
FIG. 35 illustrates an embodiment of digital single base extension genotyping.

FIG. 35 illustrates digital single base extension genotyping. Through the use of single base extension sensing as in FIG. 34, a sample may be genotyped at a large number of markers. When performed in massively parallel fashion on the sensor array chip, this can perform SNP genotyping on a large number of markers, for applications to DNA fingerprinting and identification or genetic analysis. A unique valuable feature of the present embodiment is that it is single molecule, so it can deconvolute signals from a pool of mixed samples, with direct digital counting of the different genotypes present. This can support use in forensics, where mixed samples occur, and it is desirable to catalog all the different genotypes present, and quantify in what amounts. The electronic chip based format further uniquely enables point-of-use and portable field applications of such a system, when using portable system embodiments such as that indicated in FIG. 10.

Array Operating Techniques

Figure 36:
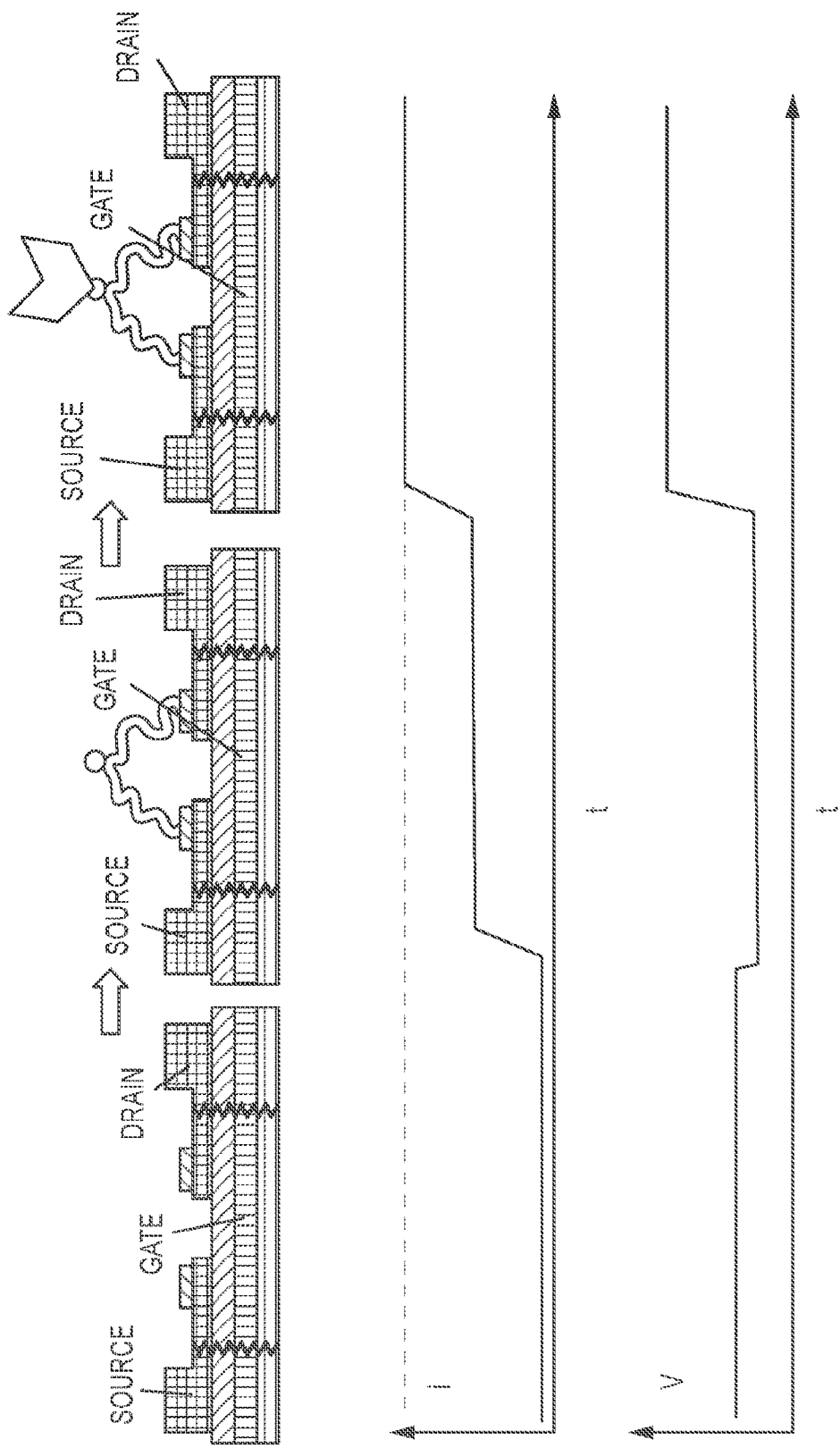
FIG. 36 illustrates an embodiment of voltage monitoring and/or direction of assembly.
Figure 37:
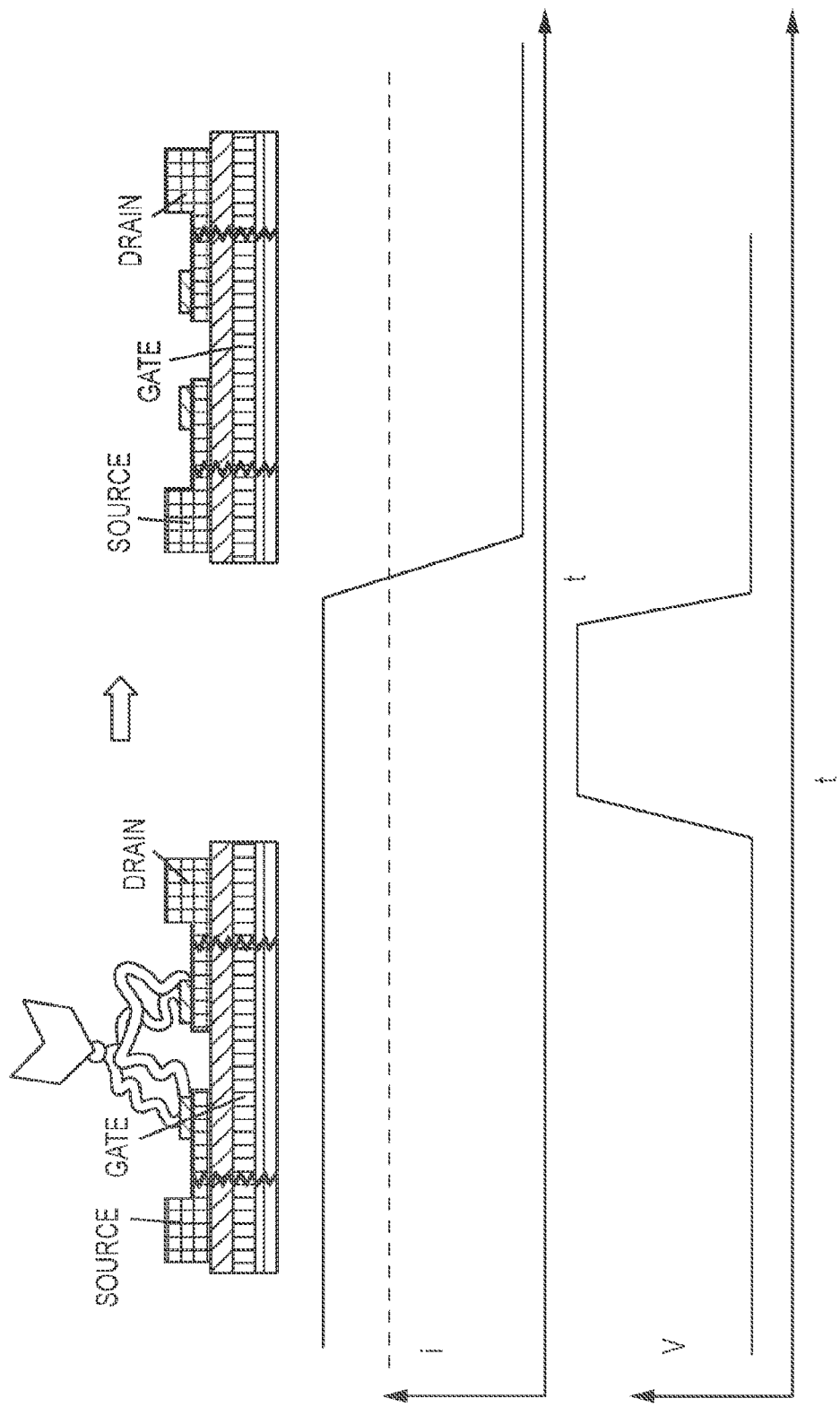
FIG. 37 illustrates an embodiment of voltage directed and monitored reset.
Figure 38:
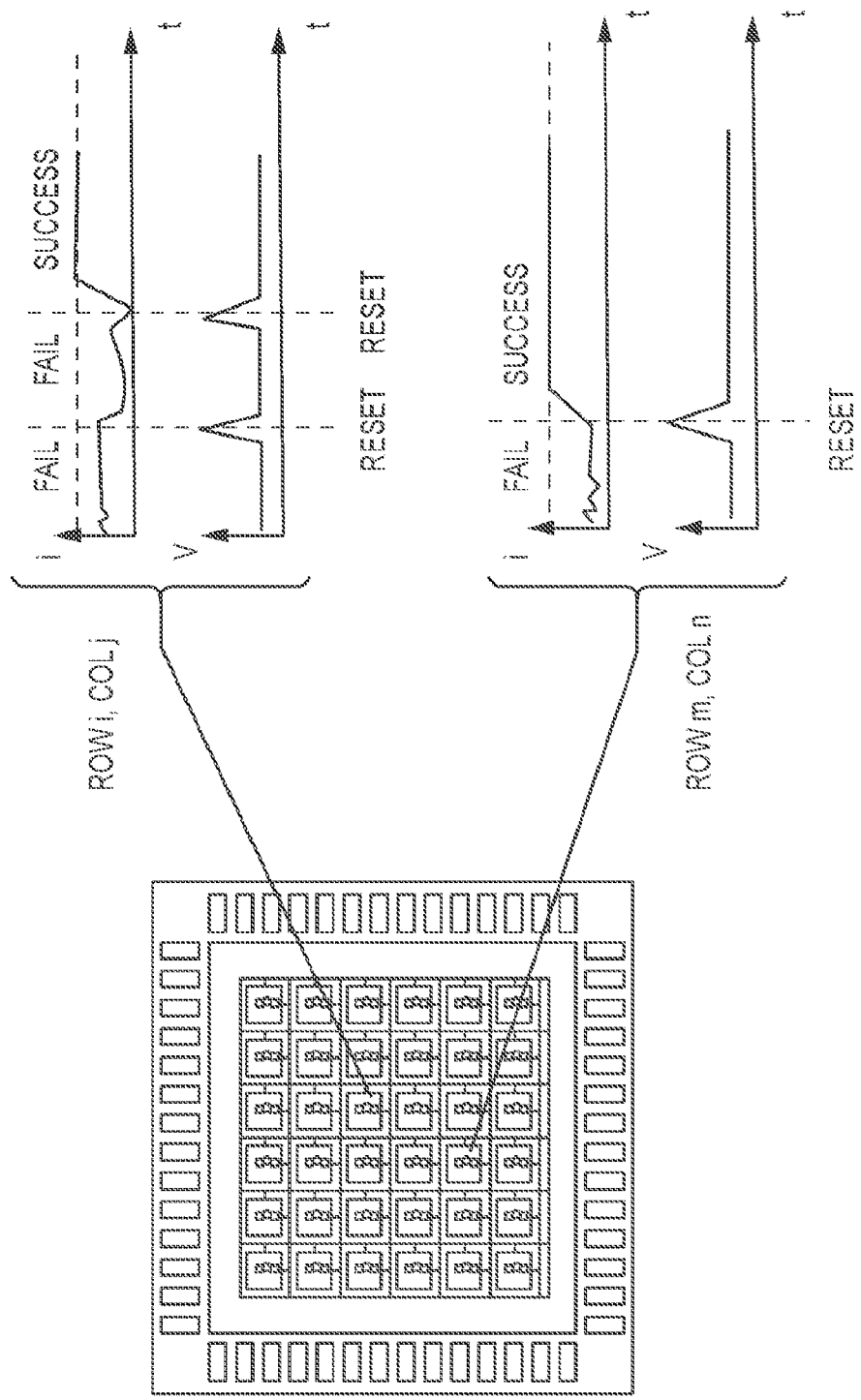
FIG. 38 illustrates an embodiment of chip-level assembly and reset functionality.

FIGS. 36, 37, and 38 illustrate various array operating techniques, such as (i) voltage directed array loading, resetting, and repeated load-reset-hold to achieve super-Poisson loading; (ii) electronic probing of sensors for QC, through major assembly and operations steps, and use of such to pre-identify viable sensors; (iii) calibration runs of individual sensors; and (iv) independent calibration. Also disclosed is voltage-directed reset, such as to remove undesirable configurations.

FIG. 36 illustrates voltage monitoring and/or direction of self-assembly of biomolecules onto electrodes or on one another. Using the gate and/or source-drain voltage, the current can be monitored to detect when bridge and probe biomolecules are properly assembled. Such voltages may also be used to drive or accelerate the assembly.

FIG. 37 illustrates voltage directed and monitored reset. The gate voltage and/or source-drain voltage can be used to eliminate a molecular construct, properly formed or improperly formed, and monitor the process for proper completion. Such a reset may force away the molecules, or induce local degrading environment changes, as indicated in FIG. 33.

FIG. 38 illustrates chip-level assembly and reset functionality. Using the electronic assembly and reset capabilities in the sensor array setting, each pixel can independently go through multiple rounds of assembly trial and reset, until proper assembly is achieved. Similarly, a chip can be recycled for a new use, after previous use, by this form of processing, or potentially pixel configuration error detection and correction could happen in the course of processing a sample. In various aspects, on chip sensor circuits for current sensing, data reduction and encoding, integration into mother board with GPU/CPU or FPGA for data transduction, and integration and combination of signals to achieve greater accuracy of final measures, including redundant or cross-array replicated measures are disclosed herein. In various aspects, all features are embodied in CMOS, or as a process layer post CMOS.

Probe Diversity on One Array:

Array elements may be diverse, such as having many probes, of r=different types, which may inform on multiple aspects of the analyte on one chip. In some aspects, anonymous/partially anonymous probes mediate trinary or higher order interactions to produce information. One preferred embodiment of this is in DNA sequencing, where the probe may be considered to comprise the polymerase, as well as the anonymous bound DNA molecule, and the interacting targets are the four dNTP nucleotides, which are sensed as they are incorporated in the trinary interaction of polymerase, template and dNTP.

Further disclosed are universal array devices that can be coupled to secondary probes/bridges (firm-ware programmable sensor array), as a universal sensor array, and as a molecular processor. The coupling is accomplished via universal contacts with conjugation chemistry, or universal bridge molecules with conjugation chemistry.

Hybridization Assays:

Disclosed herein is the use of hybridization probes for massively parallel electronic hybridization, with applications to quantifying concentration of complex mixtures of DNA or RNA targets. Non-limiting examples include gene expression, SNP genotyping, and universal tag reader arrays. Further disclosed herein is use of combinatorial encoding and decoding of array hybridization probes in this context to identify, after arrays are established, which probes are at which sensors. Disclosed are electronic concentration, electronic stringency, electronic annealing and electronic spectroscopy for detection/characterization. The single-molecule measurement as disclosed enable unique deconvolution abilities in genotyping applications, to process DNA from a mixture of individuals and enumerate the different genotypes present.

Further disclosed is the use of hybridization probes for massively parallel electronic hybridization, in conjunction with steps of enzymatic extension or ligation to achieve single base sequencing, as used in genotyping of SNPs.

Also disclosed is combinatorial decoding of probes deposited anonymously onto the array, by repeatedly binding against code word probes, such as for example, for a decoding step that relies on electronic detection.

Universal Tag Array:

In various embodiments, the hybridization probes may comprise the tag probes of a universal tag array. Such an array can comprise 1000, or 10,000, or 100,000, or 1,000,000, or 10,000,000, or 100,000,000 distinct tags. These tags can be combinatorially encoded with oligo sections tailed on the probes, and then decoded after the array is established to map which probes are at which sensors on the array, as part of the array fabrication process.

Further disclosed is the use of voltage reducible acids or bases, for localized generation of acids or bases to facilitate local stripping or activation.

Further disclosed herein is the use of binding probes for massively parallel, digital binding assays, with applications to digital quantifying concentration of complex mixtures of target molecules. In particular, such binding probes may be peptides, proteins, haptens, aptamers, or antibodies. Such binding probes can also be other chemicals, such as in the use of electronic nose applications, detection of explosives, sensing of volatile compounds, etc.

Enzyme Evolution Selection:

In various embodiments, sensor arrays wherein the probe molecules are enzymes, electronic measurement is made to characterize the enzyme-substrate interaction, and this detailed performance information is then used to select enzymes that have desired performance properties from large enzyme libraries. This may involve combinatorial decoding to identify the enzymes, or other means to capture and identify the successful enzymes.

Figure 39:
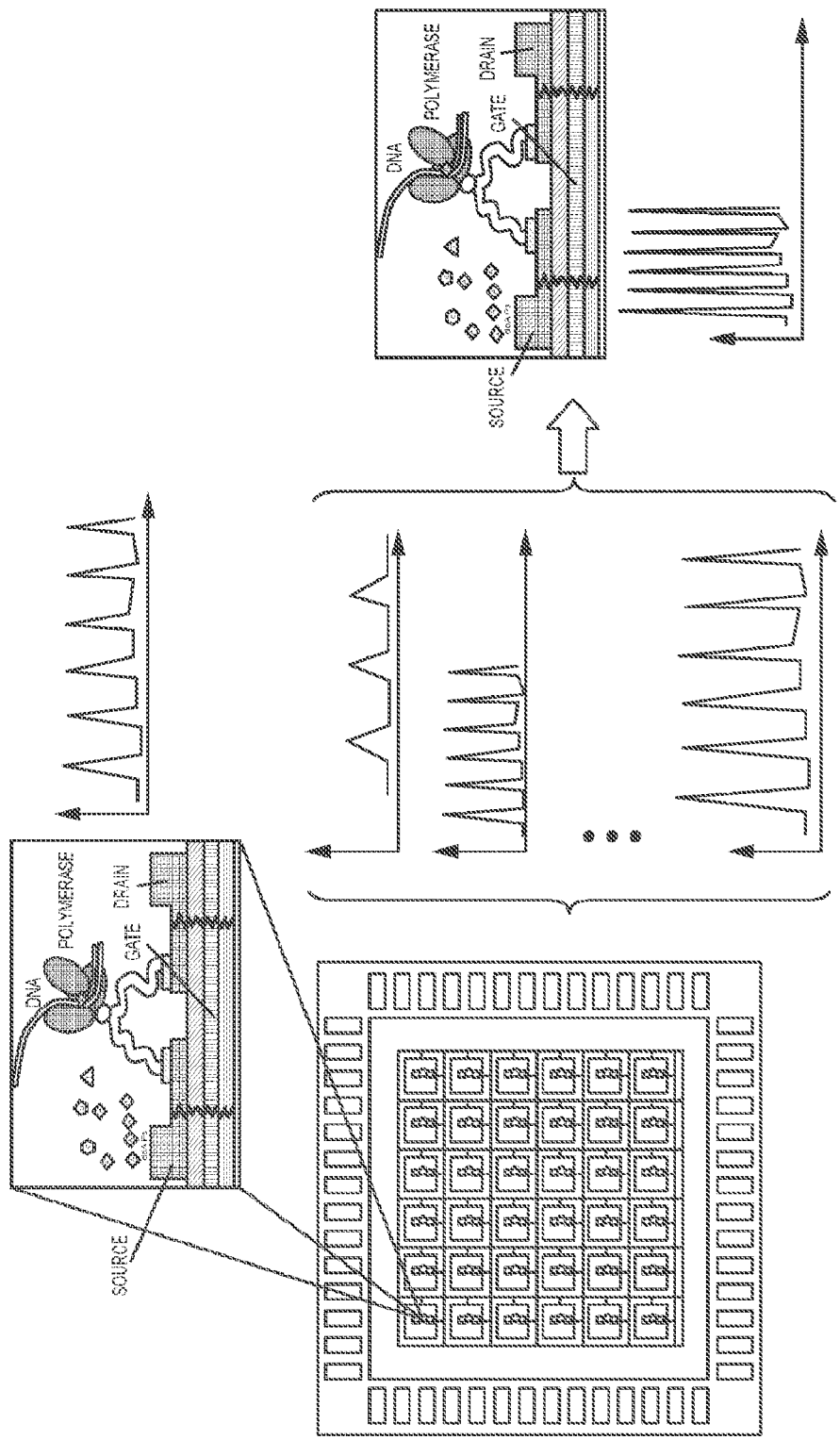
FIG. 39 illustrates an embodiment of quantitative selection of an enzyme having desired performance properties.

FIG. 39 illustrates quantitative selection of enzymes having the desired performance properties. A diversity of enzymes is established on the array, their performance properties measured with quantitative detail, allowing for the most desirable profile/enzyme to be identified. In the case shown, a polymerase is monitored for its incorporation rate, and selected for one with the highest rate of incorporation, and also with the best signal strength within the electronic detection process.

Library Screening:

Further disclosed is the use of sensor arrays for screening libraries of candidate binding molecules in order to select, identify and/or capture successful candidates. This is in contrast to methods such as phage-display library screening that are commonly used to achieve such ends.

Protein Arrays:

In various embodiments, arrays for protein-protein interaction measurement using protein or peptide probes are disclosed. Single protein-cell interactions can also be measured using protein probes, and detection of whether a cell is present is via its impact on the respective sensor or local collection of sensors. Such cell-sensor interactions can be mapped at a spatial resolution of that of the array, which can achieve nanometer scale, which is much smaller than cellular dimensions. In this way, high resolution mapping or imaging of sensor targets in a cellular context can be achieved. Single molecule data have unique advantage to deconvolute and digitize interactions, and all electronic chip based measurement have unique advantages for speed, electronic control of the reaction speed, stringency, and spectroscopic characterization through voltage sweeps.

Protein arrays can more generally be used to achieve high resolution sensor-target imaging of a larger biological complex deposited on the array. Such a complex could be cellular, or could be cell organelles, or could be large intact DNA molecules or whole chromosomes. In various embodiments, an array may be used with molecular fingerprinting methods to do large-scale structural mapping of a collection of fragments, de novo, or relative to a reference.

Further disclosed is concentration measurement, using binding or transient interacting probes against a target molecule or class of molecules. In particular, to measure concentration of DNA, RNA, or proteins.

Figure 40:
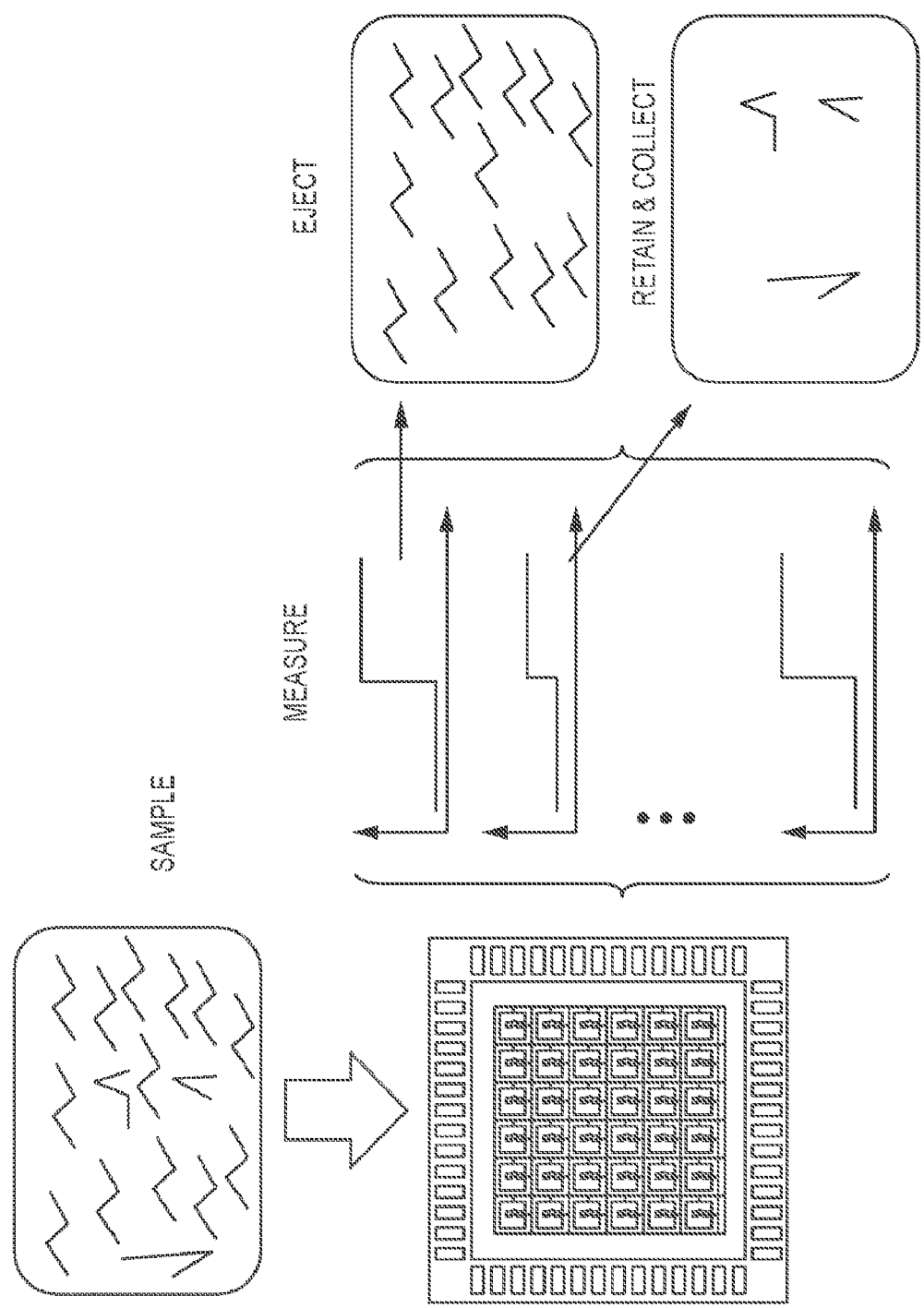
FIG. 40 illustrates an embodiment of electronic assessment and collection of desired population of targets from a solution containing a complex mix of sensor analytes.

Sensor Target Capture:

Exemplary sensor arrays extended to perform capture and collection of desired targets are illustrated in FIG. 40, in which suitable positive-outcome sensors, as determined by the respective sensor measures, are set to retain their targets, while other sensors eject their targets, with retained targets then released for subsequent collection. FIG. 40 illustrates electronic assessment and collection of desired population of targets from a solution containing a complex mixture of sensor analytes. A sample is applied to the sensory array and sensing profiles are collected. Undesirable targets based on particular profiles are electronically released and ejected in a voltage directed manner, and flushed from the system. Remaining targets can then be released and physically collected through an additional flush of the system. This process can be done repeatedly to enrich and purify a desired set of targets, or cumulatively to load the array with only desirable targets, prior to further processing or collection Retention and ejection can be performed by electronic means, such as in a voltage directed manner. This process can be carried out iteratively, with many cycles of capture and release, to accumulate a captured set of targets across many samples run over the array, and/or to repeatedly enrich and fractionate from the same sample to produce a more highly purified final capture. This enables high value molecules, based on sensor analysis, to be retained for further study, characterization, cloning, or amplification. One preferred embodiment is to collect and study DNA fragments with anomalous modifications, such as DNA damage or inclusion of modified nucleotides, such as those that are methylated. Similar applications apply to proteins.

Disclosed herein is aggregation across signals from a chip array, across a diversity of sensors, or a diversity of bridge/enzyme/voltage-measurements. Such aggregation of many signals across the array enable big-data characterization of the sample, so as to characterize a sample containing many fewer attributes or features than sensors used to accumulate measurements. This enables such arrays to be used with the methods of compressive sensing in general. This allows for applications where a very large number of low information sensor measures are aggregated to determine properties of analytes that are otherwise difficult or more costly or more complicated to measure. Sensors of the type here can be adapted for these compressive sensing uses, via the use of such a chip sensor array.

Figure 41:
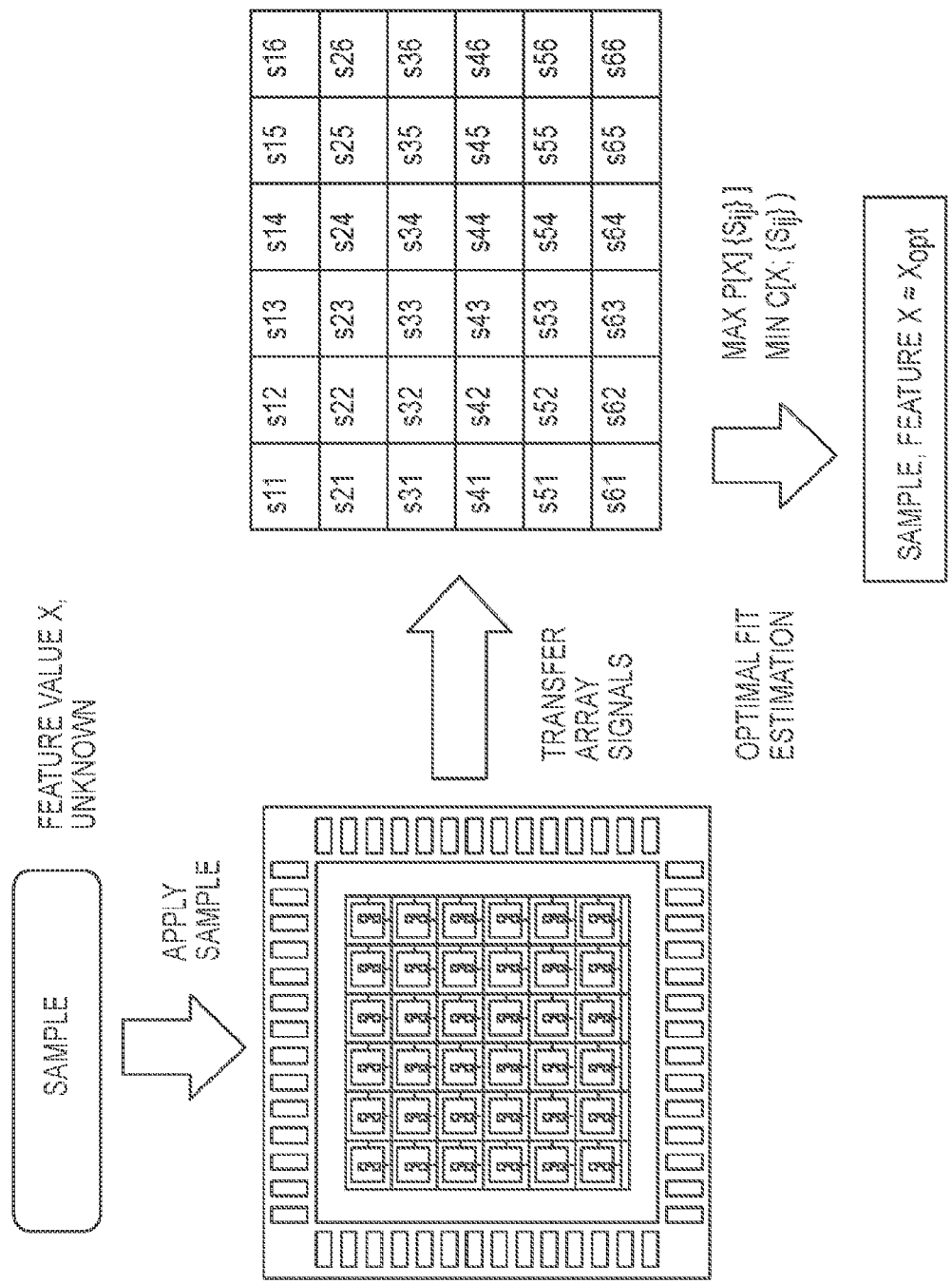
FIG. 41 illustrates exemplary use of high dimensional sensor data to determine low dimensional sample properties.

FIG. 41 illustrates an exemplary use of high dimensional sensor data to determine low dimensional sample properties. As discussed, a sample is applied to the array, and sensor signals are collected. This data is aggregated and used in conjunction with an averaging, or, in preferred embodiments, maximum likelihood or optimization-based parameter estimation algorithm, to obtain the estimate of the single or low dimensional sample feature value.

Figure 42:
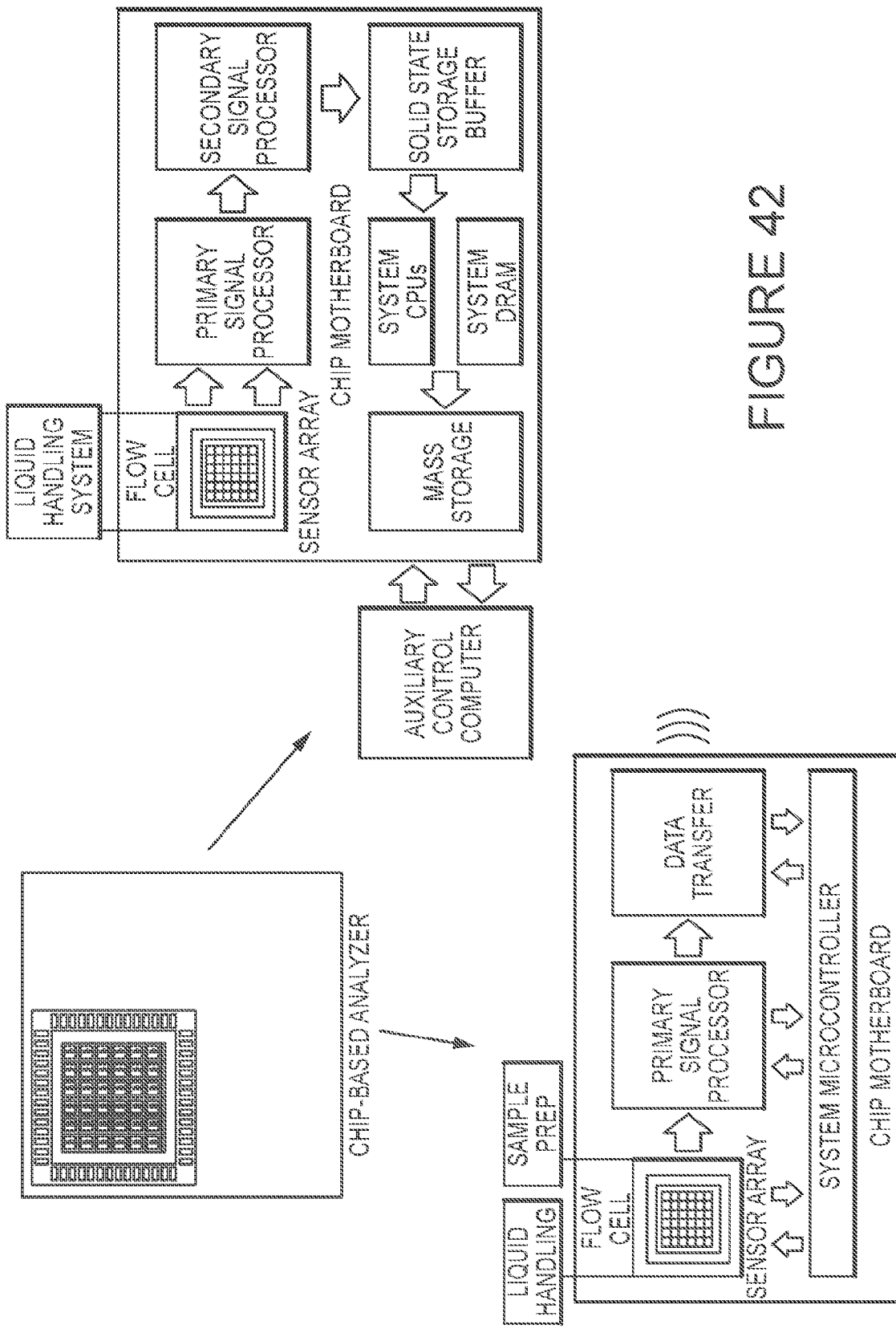
FIG. 42 illustrates examples of preferred embodiments of a chip-based analyzer, such as comprising an extended system or a compact system.

Systems:

FIG. 42 illustrates various embodiments of sensor systems in system-level use, which incorporate the general concept of a chip-based analyzer, which covers these and other system configurations built to support the use of the sensor chip. In various embodiments, the chip-based analyzer can be an extended system, or a compact system. The analyzer can represent either of these, or comparable system configurations, in the system-level applications.

Figure 43:
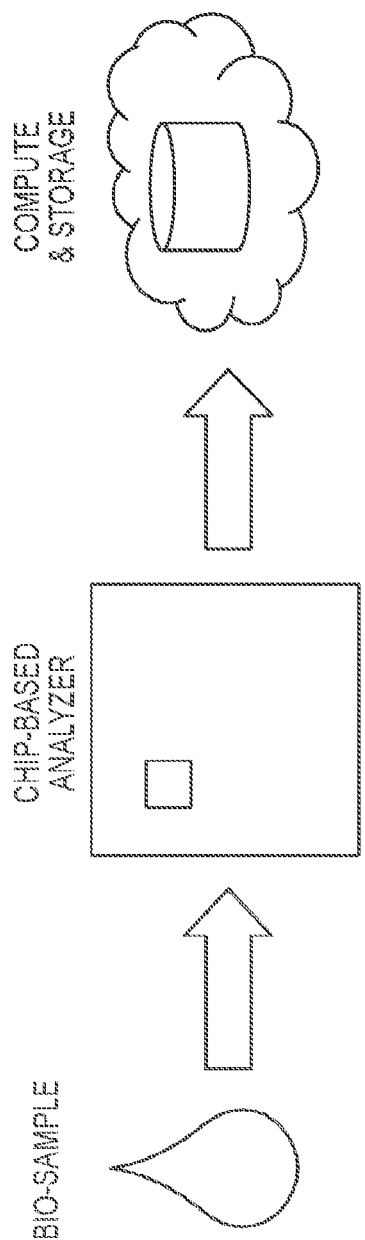
FIG. 43 illustrates an embodiment of a high-level process wherein a bio-sample is processed for introduction to the system, and primary data are further processed and stored such as in a cloud environment.

FIG. 43 illustrates a high-level process. In this example, a bio-sample is processed for introduction to the system, and primary data are further processed and stored. The basic preferred embodiment of an application process is to obtain a bio-sample, suitably prepare it for introduction into the chip-based analyzer ("sample preparation"), and then transfer the primary data to a secondary cloud environment for further processing and storage. Sample preparation may include purification, such as purifying DNA from tissue or blood. In non-limiting examples, the analysis may be DNA fingerprinting, genotyping, or DNA sequencing. The preferred destination environment would be a cloud-computing environment, such as to support scalable data processing needs.

Figure 44:
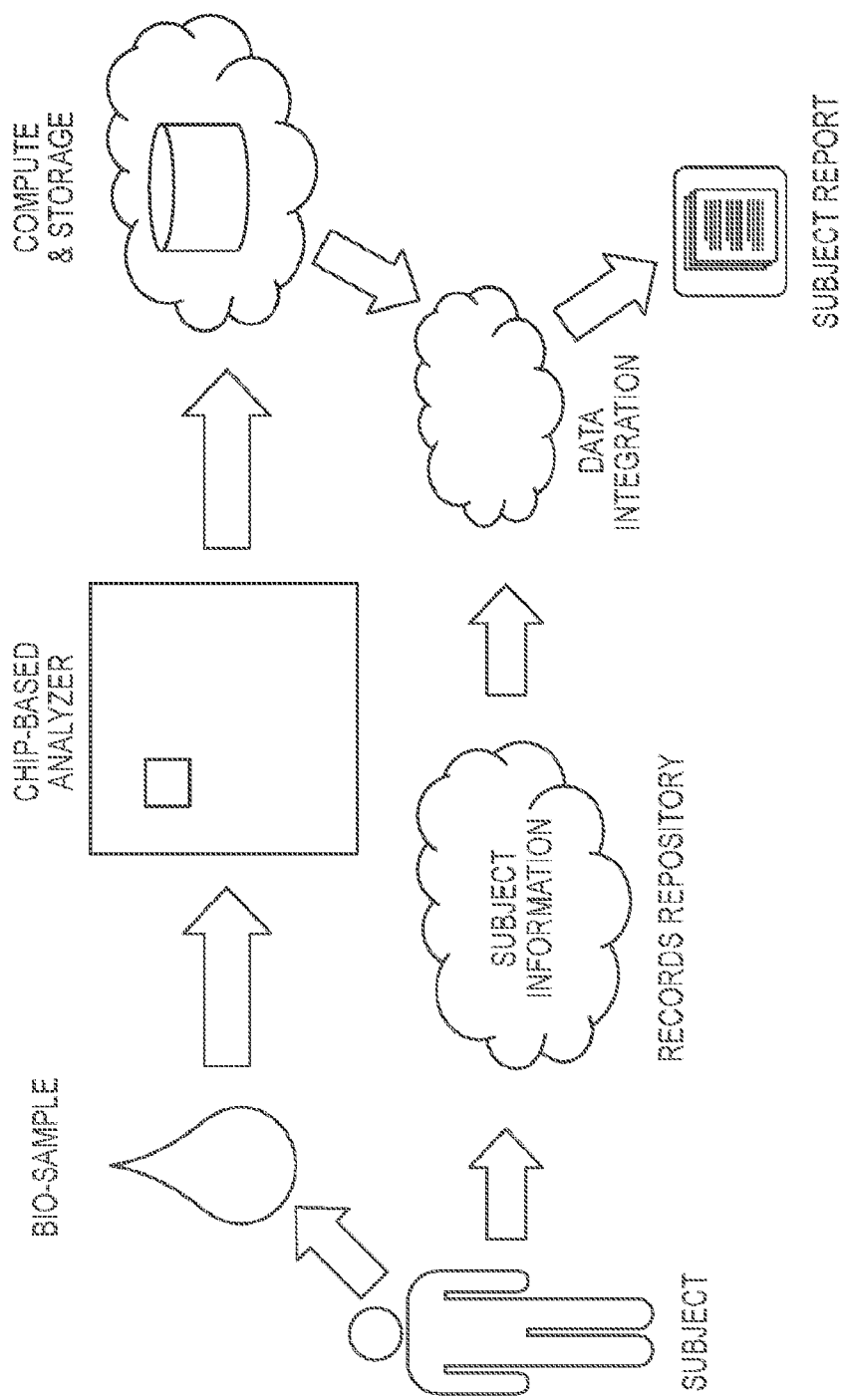
FIG. 44 illustrates an embodiment of integrated analysis of a subject.

FIG. 44 illustrates integrated analysis of a subject. In a preferred embodiment of the basic process of FIG. 43, a subject provides a bio-sample for analysis, along with additional information about the subject, and said information and analyzer results are integrated into a report. Disclosed is a preferred embodiment of the basic measurement process, where the test subject provides the biosample, and also provides other information relevant to their identity or phenotype or other state variables, and such data is processed and aggregated as shown, to produce a report integrating the sensor/analyzer results with the other pertinent information from the subject. In general the subject may be a human, as is the case in preferred embodiments of healthcare-related profiling, or in human identification or forensics, or could be an animal, plant, or any other localized source of bio-sample and affiliated information, such as a soil sample, to be affiliated with a time, location and image of the local conditions. For example, additional information could comprise personal identifiers, health records, or general phenotypic data. Herein the term "subject" is used to indicate all such generalizations. In other embodiments, subjects could be animal, plant, bacteria, virus, or any entity that can be characterized by the chip-based analyzer.

Figure 45:
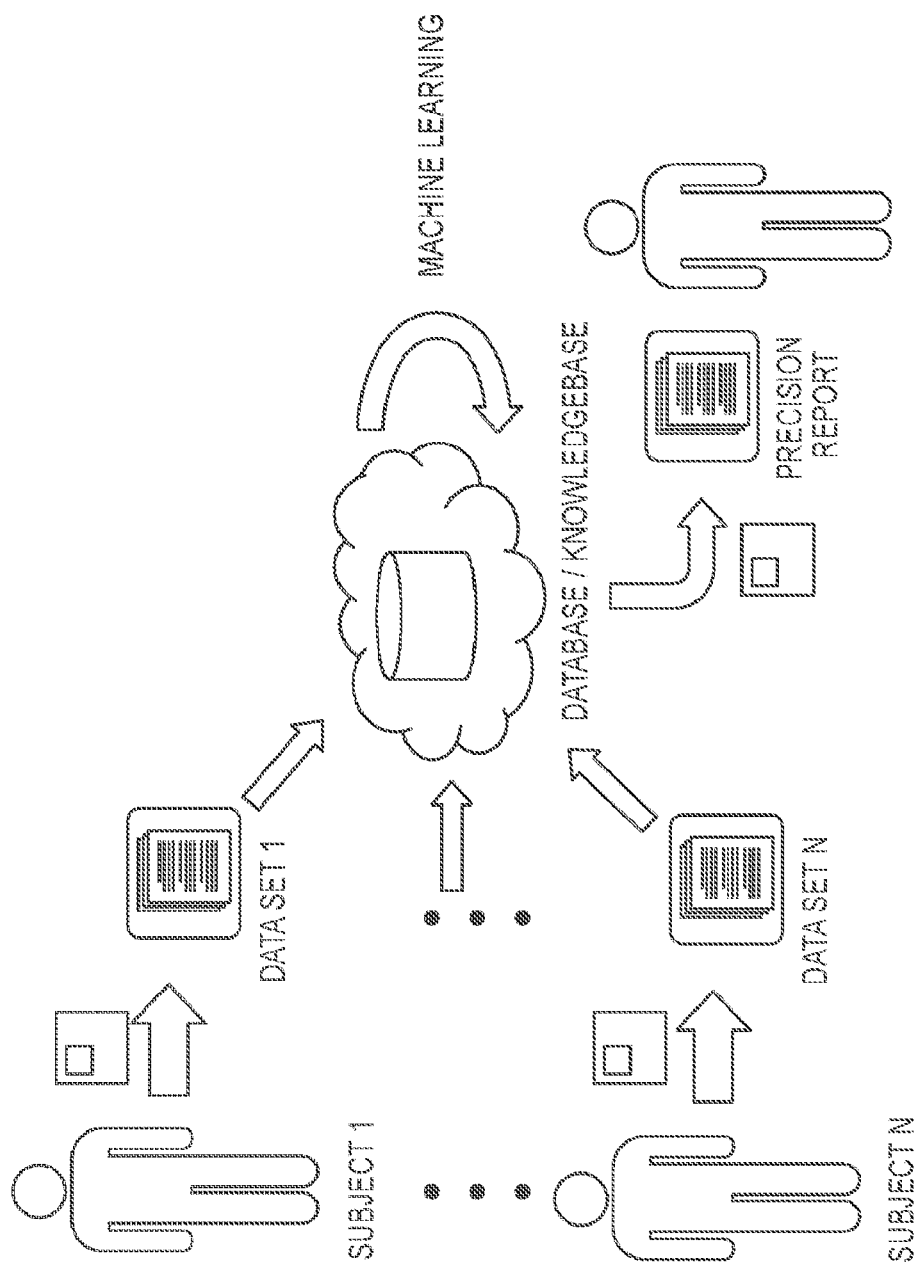
FIG. 45 illustrates an embodiment of creation of database/knowledgebase.

FIG. 45 illustrates an embodiment of the creation of a database/knowledgebase by many instances of applying the analyzer and compiling a database of subject information and analyzer results. The analysis of many subjects, as in FIG. 44, can be done in a distributed fashion to produce a database of such reporting results. This database can further be subject to machine learning techniques. Machine learning can be applied to this to create a knowledgebase with the ability to infer, interpolate or extrapolate results, and to develop means to predict or extrapolate missing or future information from what is available. The resulting database/knowledge base is then used to deliver precision reports, either for the original subjects or new subjects, that contain enhanced and more accurate or more deeply interpreted or predictive information. In preferred embodiments, this is used for healthcare profiling applications. This is also used for human identification or forensics, based on a database of identities and DNA fingerprinting measures. In general, subjects can be an animal, plant, bacteria, virus, or any entity that can be characterized by the chip-based analyzer.

Compact Systems:

In various embodiments, chip devices can be very small with low power consumption, enabling assembly of compact, robust systems amenable to portable and mobile analysis systems. These systems are compatible with coupling to mobile phones or related cellular electronics or WiFi/Bluetooth-class transmitter/receivers, to achieve connected mobile sensor devices. The miniaturization and cellular communication also affords implantable sensor devices that can be implanted into humans or animals, or plants, or cultured cells, to achieve in vivo monitoring. Exemplary devices could be reduced to the 10 micron scale or smaller, at which point they could also be injectable at any sites into an animal or human, including small enough to circulate in the blood stream.

Figure 46:
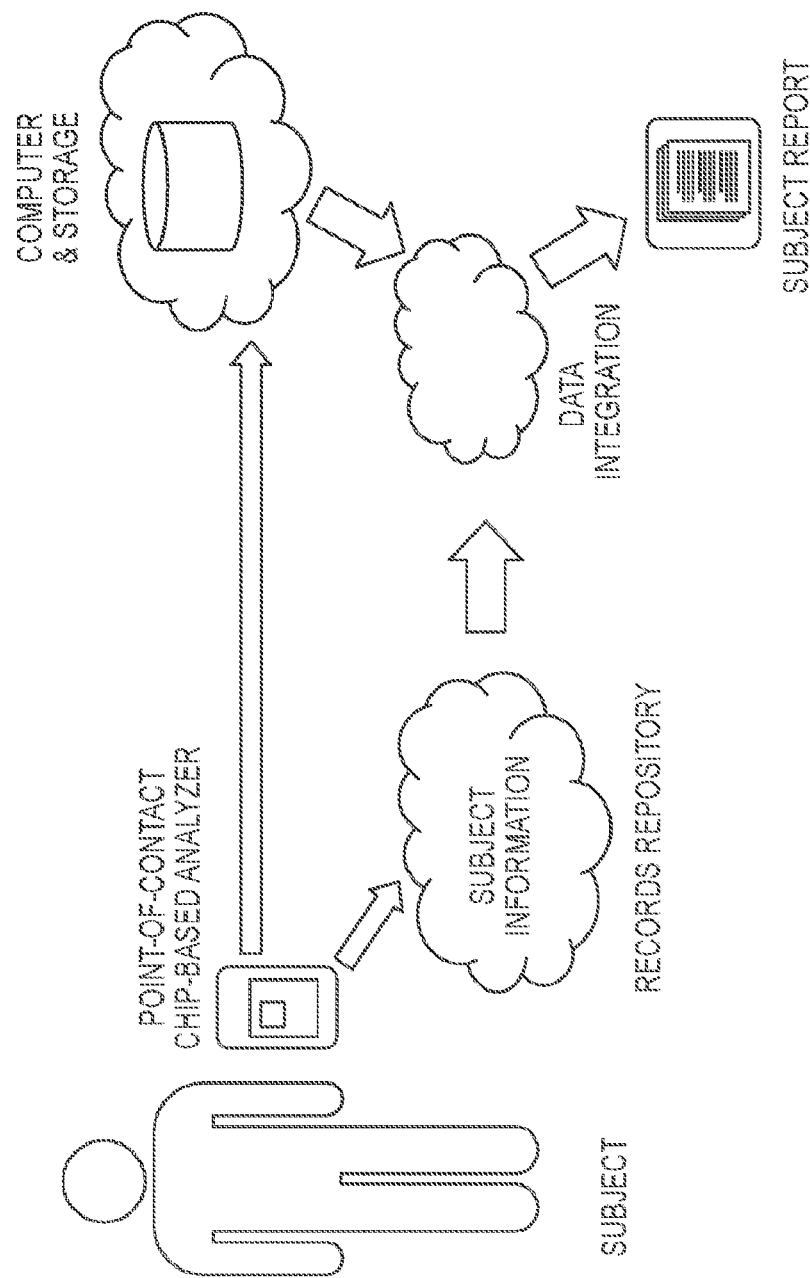
FIG. 46 illustrates an embodiment of a point-of-contact chip based analyzer.

FIG. 46 illustrates an example of a point-of-contact chip based analyzer. The chip format enables mobile, portable or handheld form factor analyzers, for point-of-contact or point-of-care applications, which allow field-base or highly distributed engagement with subjects. This could include, for example, applications to subjects at a border or customs or crime site, or environmental monitoring in the field. Many such applications are enabled by mobile, portable, or handheld devices, and coupling into the above system-level considerations.

Figure 47:
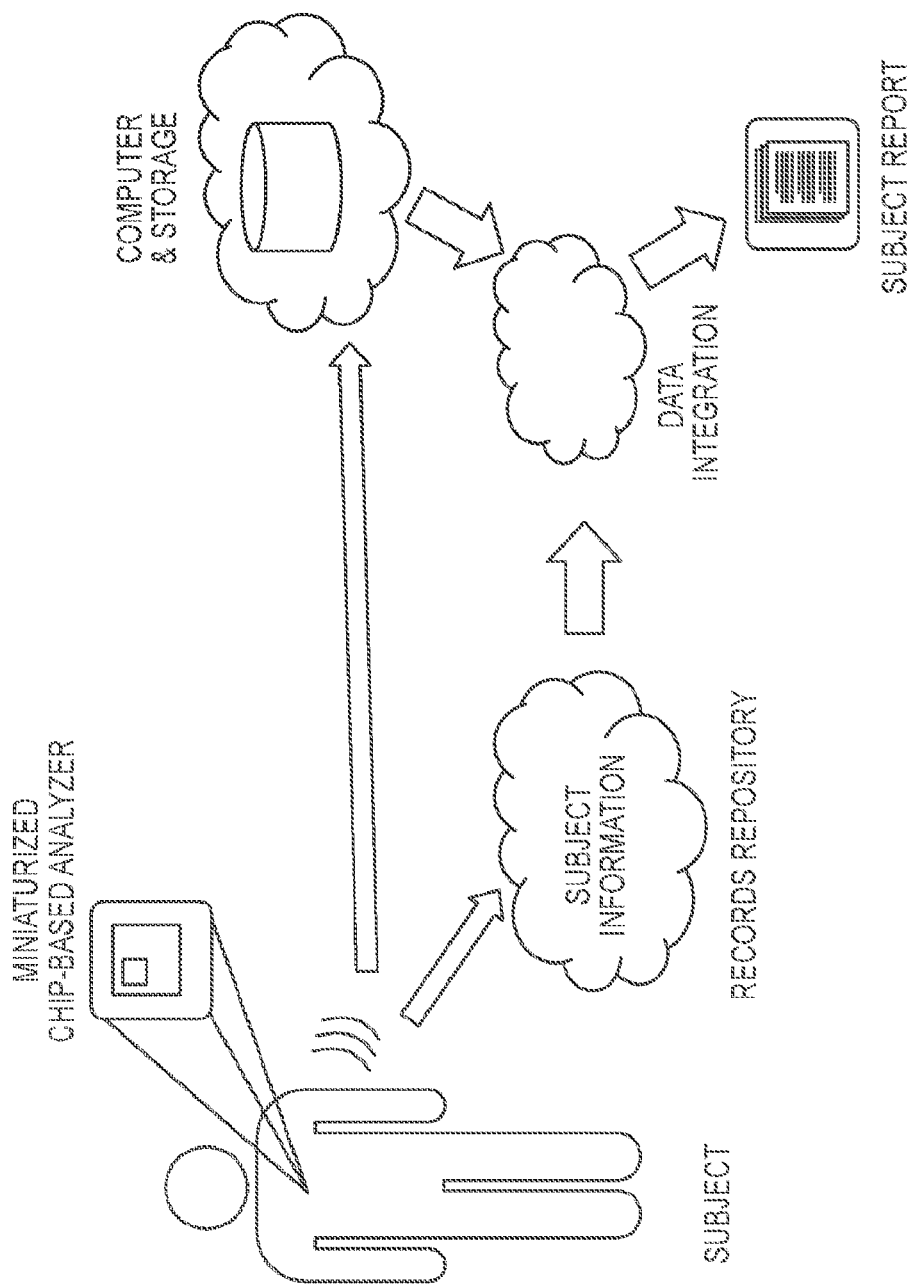
FIG. 47 illustrates an embodiment of a wearable/embeddable analyzer.

FIG. 47 illustrates an embodiment of a wearable and/or embeddable analyzer. The chip format enables a wearable, implantable or in vivo analyzer, through the use of wireless communications of data, and miniaturization down to the scale of centimeters, millimeters, or micrometers. Compact systems can provide for wearable or implantable devices, which enable applications of real-time monitoring of subjects, including localization to critical sensing sites on or within the subject. In the healthcare context, this may enable monitoring of health related variables, such as the content of a micro biome based on DNA sequence monitoring of bacteria present on the skin or in the gut, or as pertains to wound healing and monitoring for infections. Many such applications are enabled by wearable and implantable devices, and coupling into the above system-level considerations.

Figure 48:
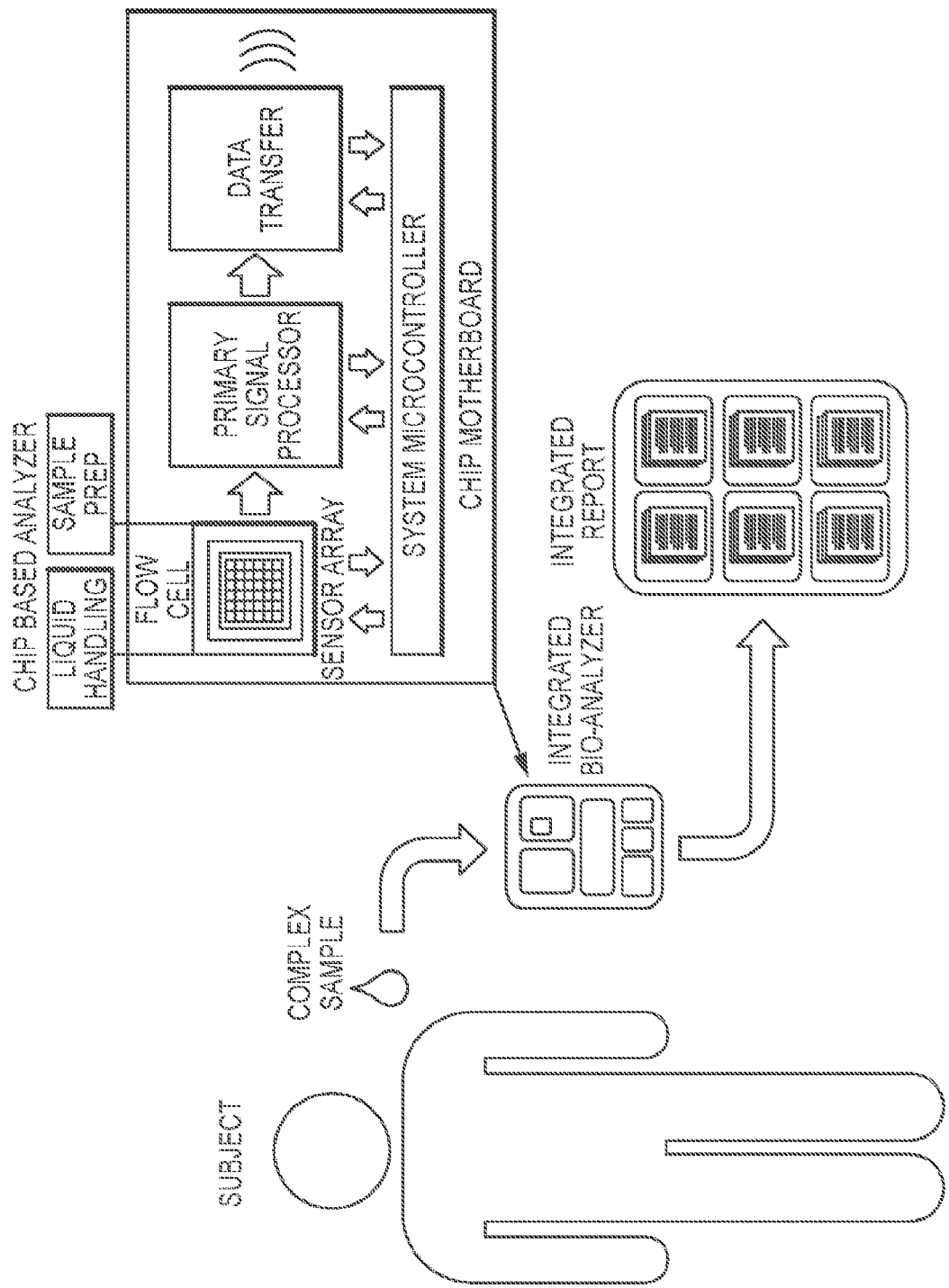
FIG. 48 illustrates an embodiment of a multi-modality integrated bio-analyzer.

FIG. 48 illustrates an embodiment of a multi-modality integrated bio-analyzer. Using the compact system, the chip-based analyzer can be integrated into a system that measures multiple modalities from a bio-sample or set of bio samples, and delivers an integrated, multi-modal report. Compact/miniaturized systems provided by the chip sensor array format also enable embedded systems, where the chip-analyzer is incorporated into a multi-modal sensor system, which itself is preferably compact, portable, mobile, hand-held or point-of-use compatible, or wearable or implantable. In general, subjects could be animal, plant, bacteria, virus, or any entity that can be characterized by the chip-based analyzer. In particular, the chip analyzer in this multi-modal system may provide genetic analysis, in particular in the form of DNA fingerprinting/ID, genotyping, or DNA sequencing.

Figure 49:
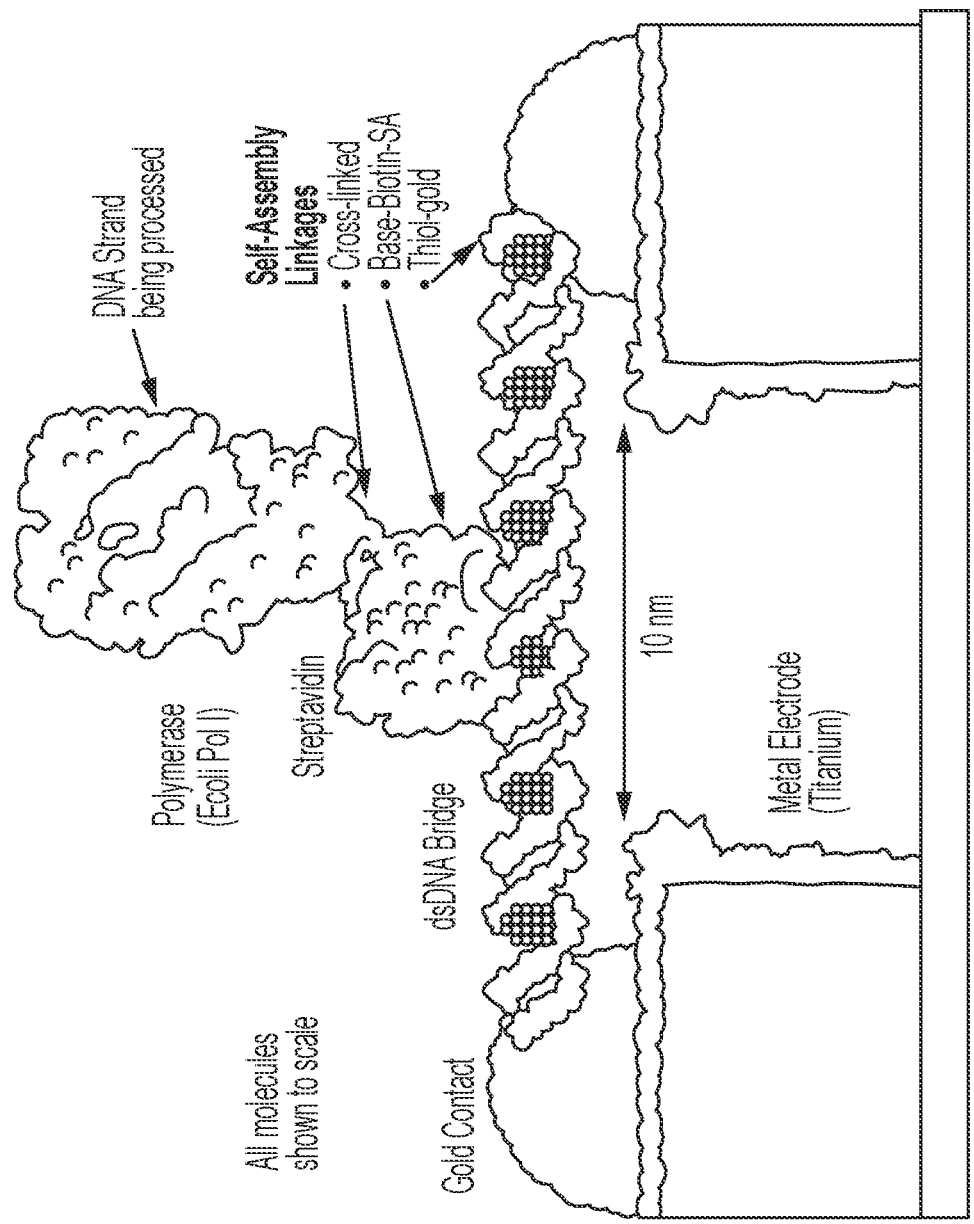
FIG. 49 illustrates an embodiment of a molecular sensor structure used for experimental work.

Referring now to FIG. 49, an embodiment of a molecular sensor structure used for experimental work is illustrated. This illustration shows the bridge and probe molecule structure typically used for experimental work. The bridge shown is a double stranded DNA molecule of 20 nm length (60 bases), having thiol groups at both 5' ends for coupling to gold contacts disposed on metal electrodes. The probe molecule used here is a polymerase, in particular $E.$ $Coli$ Pol I, chemically crosslinked to a streptavidin protein, which in turn is coupled to the bridging at a biotinylated nucleotide in the synthetic DNA oligo. FIG. 49 is shown to scale for the sizes of the molecules and atoms.

Figure 50:
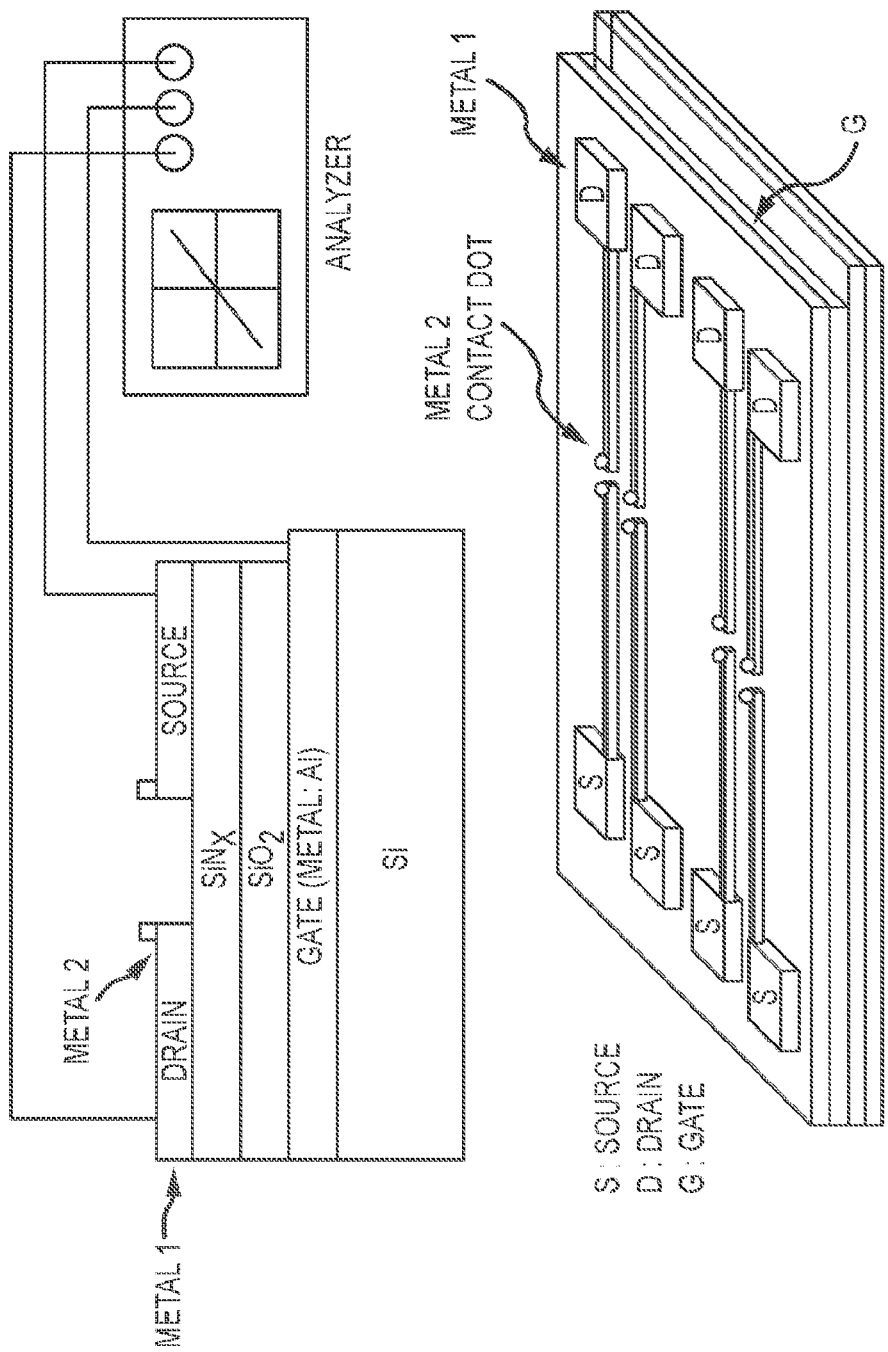
FIG. 50 illustrates an exemplary schematic of a test set-up for taking electrical measurements on molecular sensors.

With reference now to FIG. 50, an exemplary schematic of a test set-up for electrical measurements on molecular sensors is illustrated. In the upper portion of FIG. 50, a cross section of the electrode-substrate structure is illustrated, along with attachment to the analyzer for applying voltages and measuring currents through the bridge molecule. In the lower portion of FIG. 50, a perspective view of an electrode array for bridging circuits is illustrated. In this example, each pair of electrodes comprises contact points of "metal-1" (i.e., a first metal) disposed on electrodes of "metal-2" (i.e. a different metal). In the present experiments, contact points comprise gold beads or gold coated electrode tips, either of which support the self-assembly process wherein thiolated molecules lock in place via thiol-gold bonds.

Figure 51A:
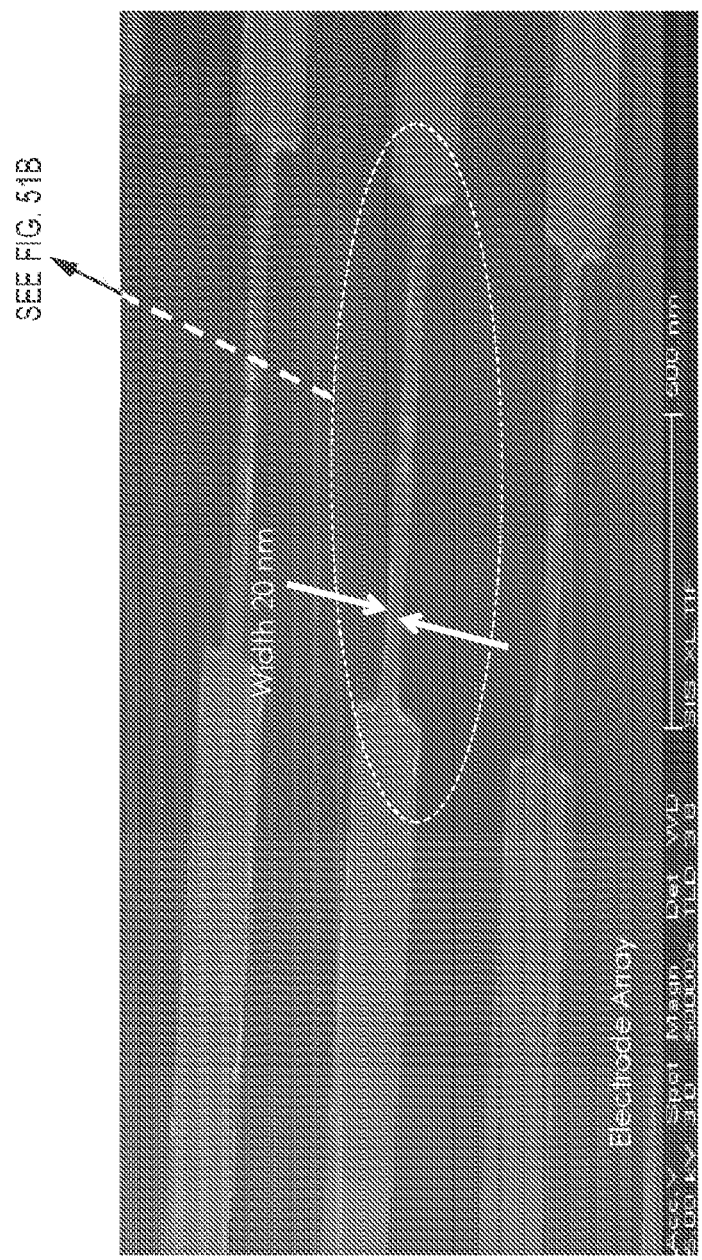
FIGS. 51A, 51B and 51C are electron microscope images of electrodes comprising gold metal dot contacts usable for bridge binding.
Figure 51B:
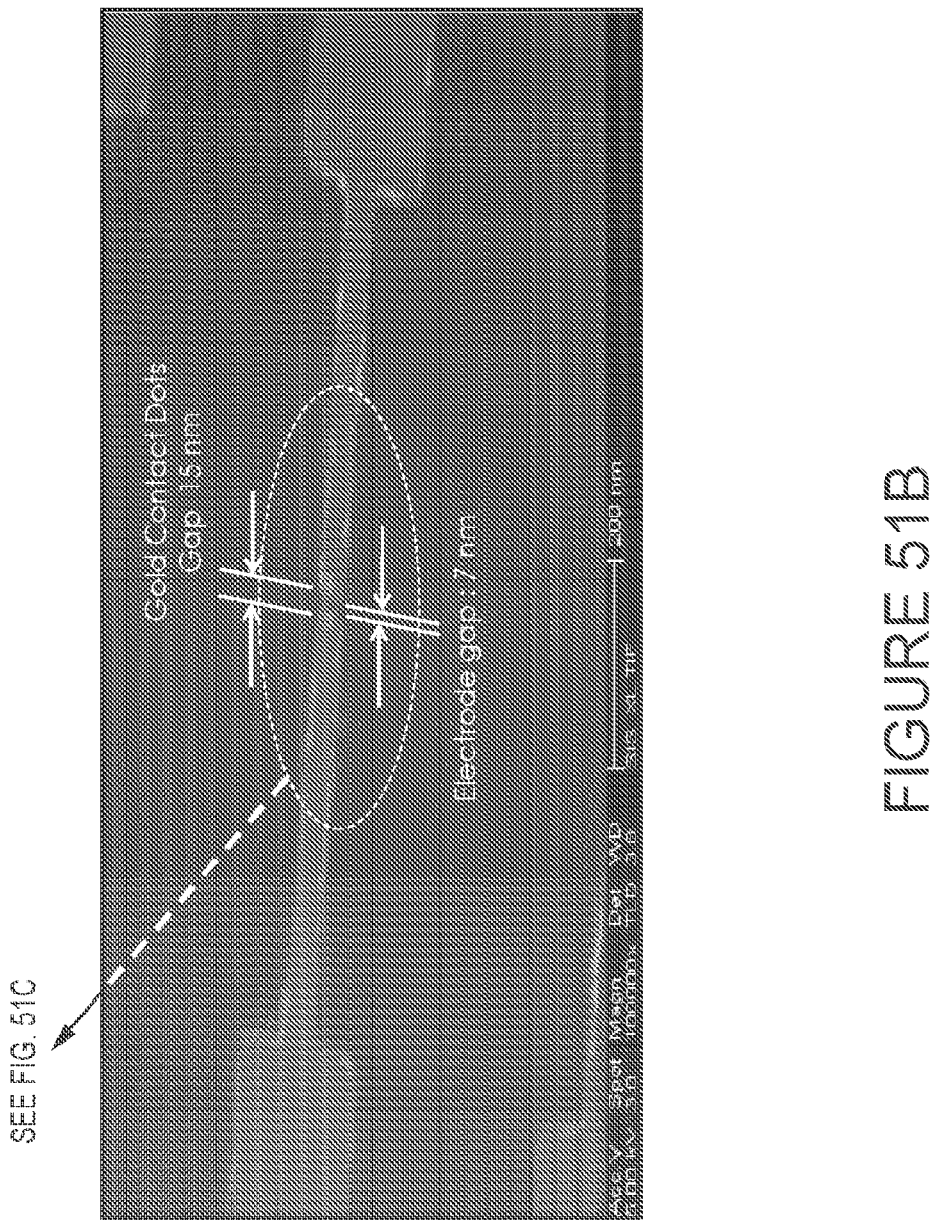
Figure 51C:
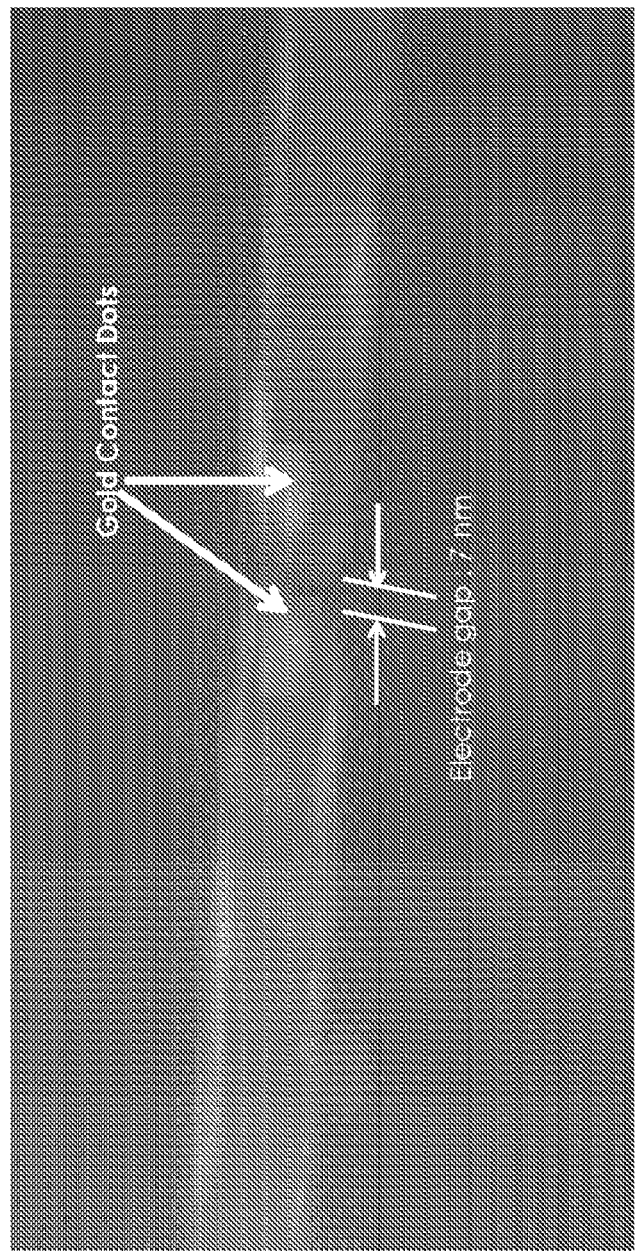

FIGS. 51A, 51B, and 51C are electron microscope images of electrodes comprising gold metal dot contacts usable for bridge binding. In this example, the electrodes were disposed on a silicon substrate, and were produced via e-beam lithography. The EM image of FIG. 51A shows the array of electrodes, in this case titanium with gold dot contacts disposed thereon. FIG. 51B provides a close-up EM image showing an electrode gap of 7 nm with gold dot contacts having a 15 nm gold-to-gold spacing. FIG. 51C is a further close-up EM image showing approximately 10 nm gold dots disposed at the tips of the electrodes.

Figure 52:
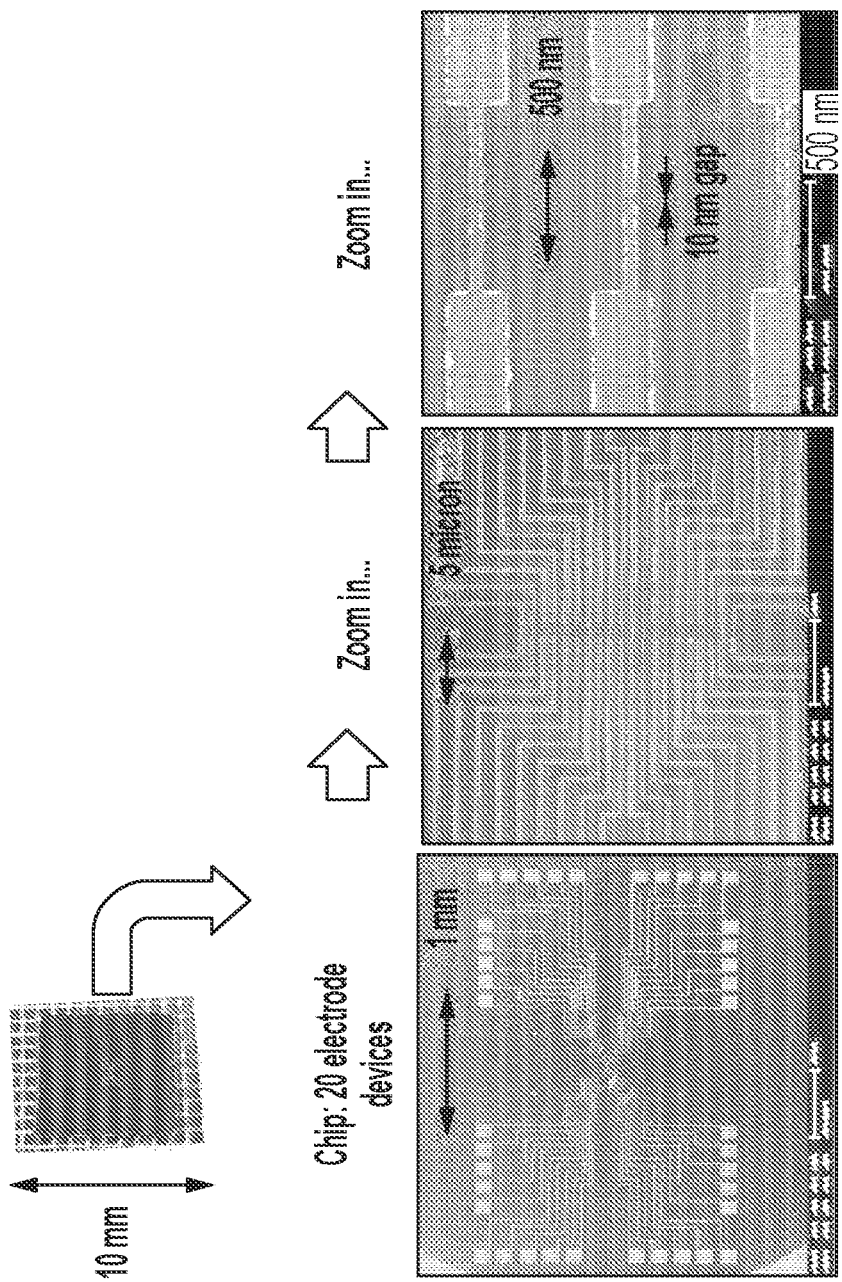
FIG. 52 illustrates an example of electrode test chip architecture.

FIG. 52 illustrates an example of electrode test chip architecture. This electrode array is formed on a 1 cm silicon substrate using e-beam lithography. The series of SEM images shows the 20 electrode pairs at increasing resolution, down to the 10 nm scale of the electrode gap.

Figure 53:
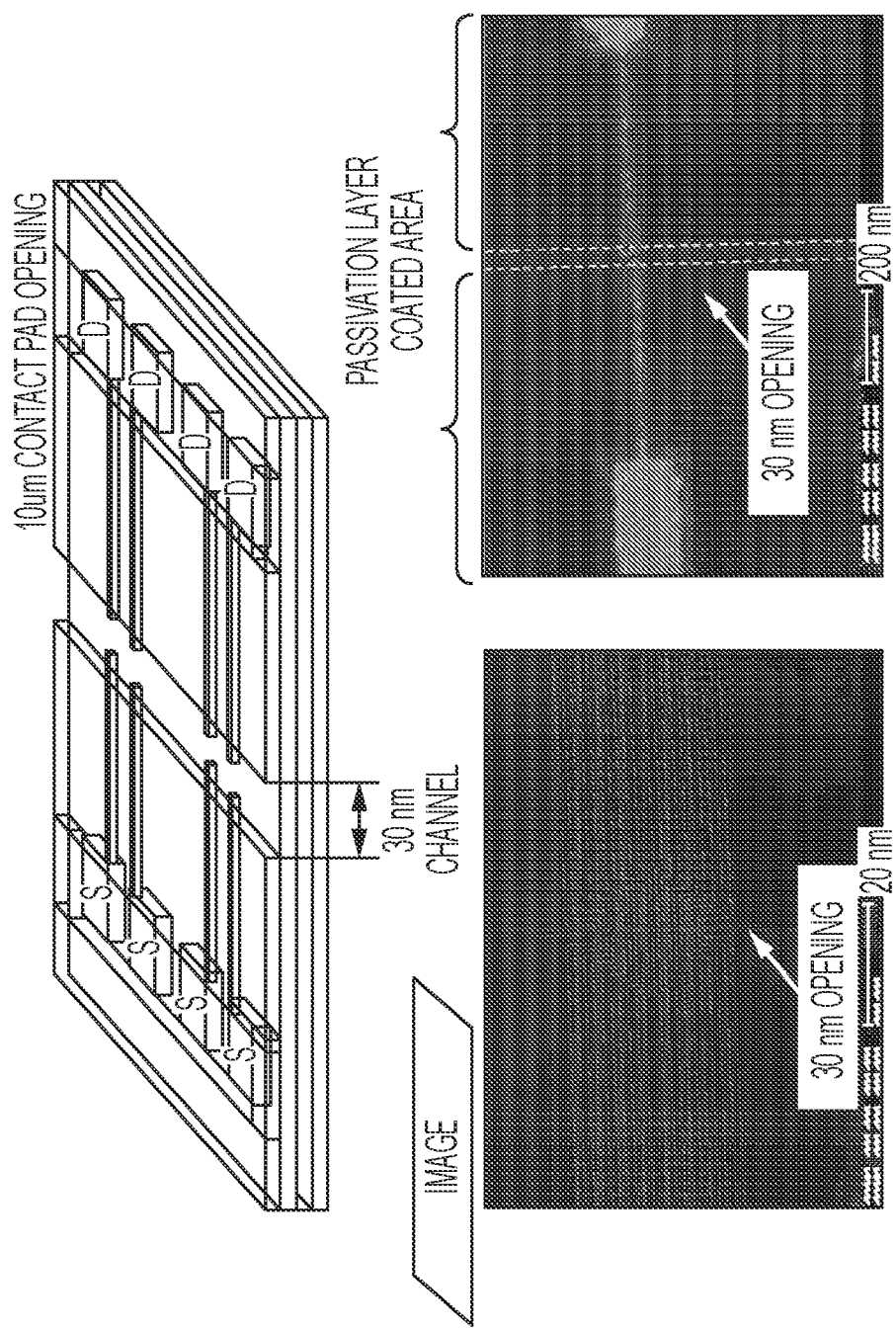
FIG. 53 illustrates use of a passivation layer on the device to protect the electrodes from solution.

FIG. 53 illustrates use of a passivation layer on the device to protect the electrodes from solution. In this example, the passivation layer is $SiO_2$. Openings in the passivation layer exposing electrode areas are of nm scale, and the electrical contact pads are on a 10 micron scale.

Figure 54:
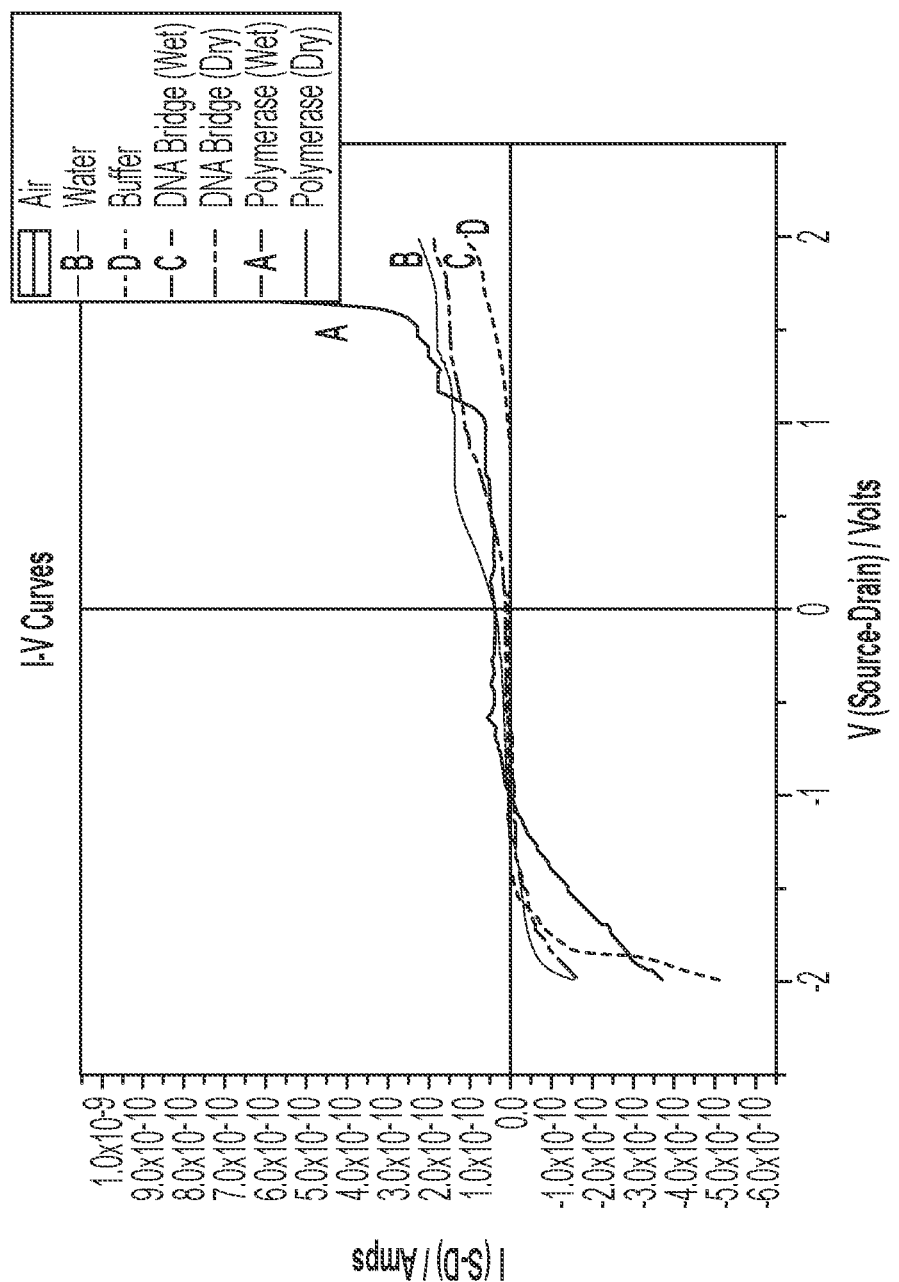
FIG. 54 sets forth plots characterizing conductivity of the assembled sensor complex.

FIG. 54 sets forth plots characterizing conductivity of the assembled sensor complex. The plots are the measured current-versus-voltage (I-V) characteristics of DNA bridge molecules and complete sensor complexes (bridge with polymerase) in wet (dilute salt buffer) and dry (air) conditions, along with controls of open circuit electrodes in air, water and dilute salt buffer. The plots show that the bridge and sensor complex conduct on the order of 100 pico-Amp currents at 1 Volt of applied source-drain voltage. Measurements are done on semiconductor parameter analyzer via an SMU.

Figure 55:
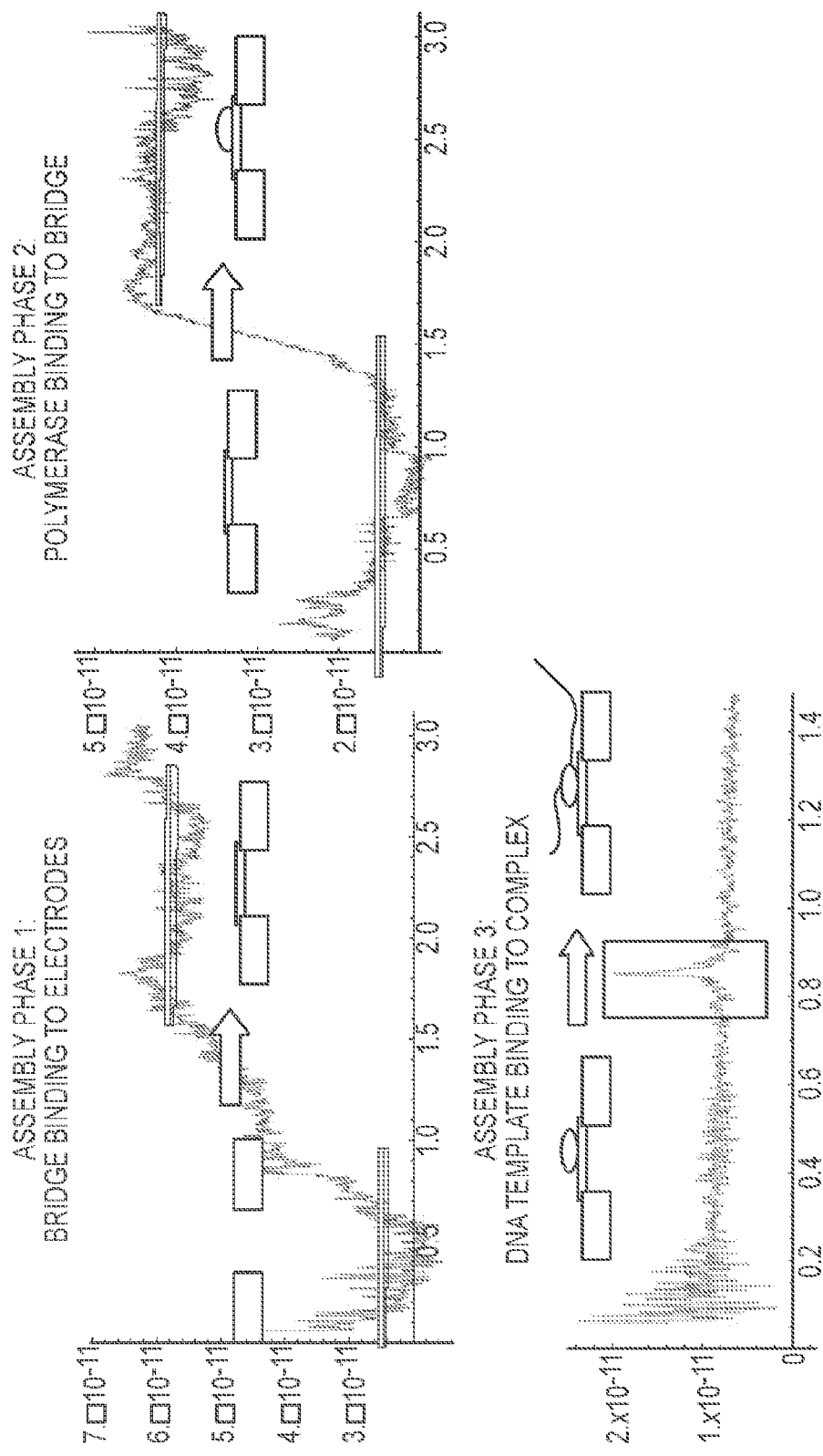
FIG. 55 shows electronic monitoring of the self-assembly of a molecular sensor assembly comprising gold-dot contact electrodes.

With reference now to FIG. 55, molecular sensor assembly onto gold-dot contact electrodes is shown being electronically monitored. Current versus time measurements are used to monitor self-assembly of bridge and molecular sensor complex. The plot at the upper left shows Phase 1 of the self-assembly wherein double stranded DNA bridge assembles with thiol groups on 5' ends onto electrode gold contact point, as evidenced by a jump in current. The plot at the upper right shows Phase 2 of the self-assembly wherein polymerase-streptavidin complex binds to a biotinylated site on the dsDNA bridge, as evidenced by another jump up in current. The plot at the lower left shows Phase 3 of the self-assembly process wherein primed single-stranded DNA template binds to the polymerase to complete the complex, as evidenced by another spike in current versus time.

Figure 56:
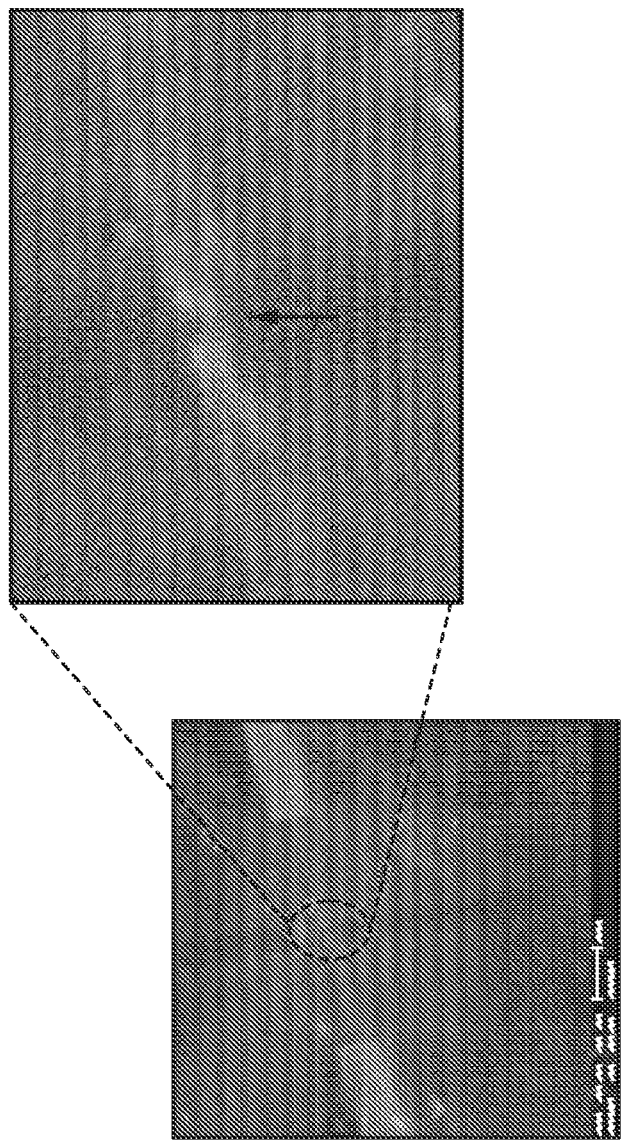
FIG. 56 shows EM images of the assembled structure after the phases of assembly discussed in reference to FIG. 55 are complete.

FIG. 56 shows EM images of the assembled structure after the phases of assembly discussed in reference to FIG. 55 are complete. The EM images show the bridge-complex directly visible without labeling as blurry high contrast region joining electrodes (arrow).

Figure 57:
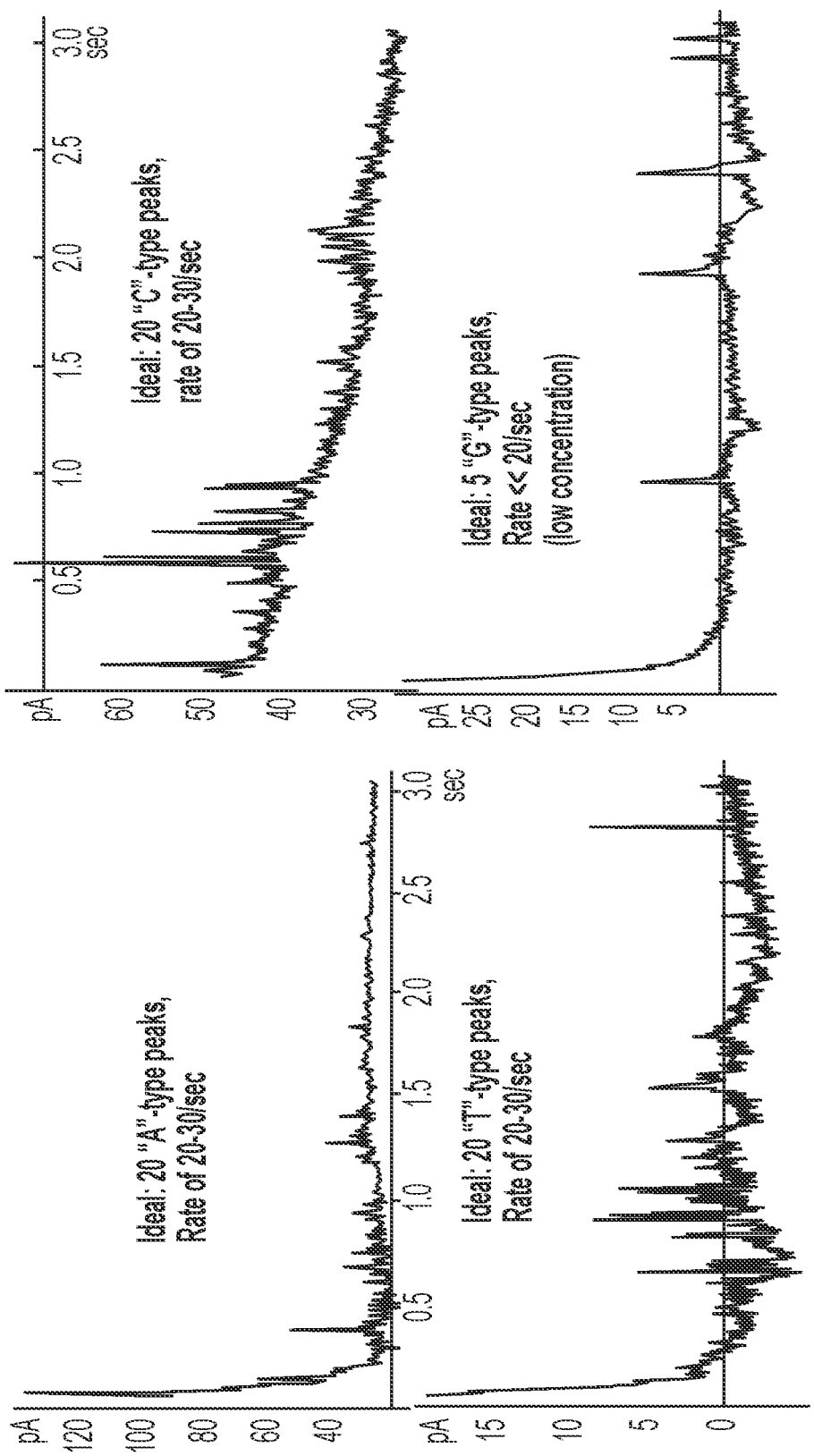
FIG. 57 demonstrates the measuring of molecule incorporation signals with the sensor.

With reference now to FIG. 57, measuring incorporation signals with the sensor is demonstrated. The plots in FIG. 57 show the current signals resulting from the sensor being supplied with various primed, single stranded DNA sequencing templates and dNTPs for incorporation and polymerization. In each case, the major signal spikes represent signals from discrete incorporation events, wherein the polymerase enzyme adds another base to the extending strand. In the plot at the upper left, the template is 20 T bases. In the plot at the upper right, the template is 20 G bases. In the plot at the lower left, the template is 20 A bases. Lastly, in the plot at the lower right, the template is 20 C bases. The approximate rate of incorporation observed is about 10 to 20 bases per second, which is consistent with standard enzyme kinetics except for the lower rate of ~1 base per second presumed due to rate limiting factors (e.g., lower dNTP concentration).

FIGS. 58A and 58B illustrate an embodiment of a sensor based on a peptide alpha-helix bridge molecule. In FIG. 58A, the bridge molecule in one specific preferred embodiment which is reduced to practice is a peptide having the 66 amino acid sequence, CAEAAAREAAAREAAAREAAAREAAAREAAA{Lys-Ahx-Biotin}EAAAREAAAREAAAREAAAREAAAREAAARC, (SEQ ID NO: 1)

which features a 61-amino peptide based on repeats of the motif EAAAR, known to favor an alpha-helix structure. Cysteine amino acids at the termini provide for thiol-gold coupling to the gold contacts disposed on chromium electrodes, A central lysine placed in the peptide is modified to include biotin on an Ahx linker to support binding of a neutravidin protein for coupling purposes. The alpha helical from of the peptide is approximately 9 nm in length. FIG. 58B shows the fully assembled sensor, with the alpha-helix bridge coupled to a neutravidin via the known biotin-neutravidin binding reaction. The polymerase is also attached, in this case with an additional biotin-maleimide linker that has been conjugated to a surface cysteine on the polymerase, via the known maleimide-cysteine covalent coupling reaction.

Figure 59A:
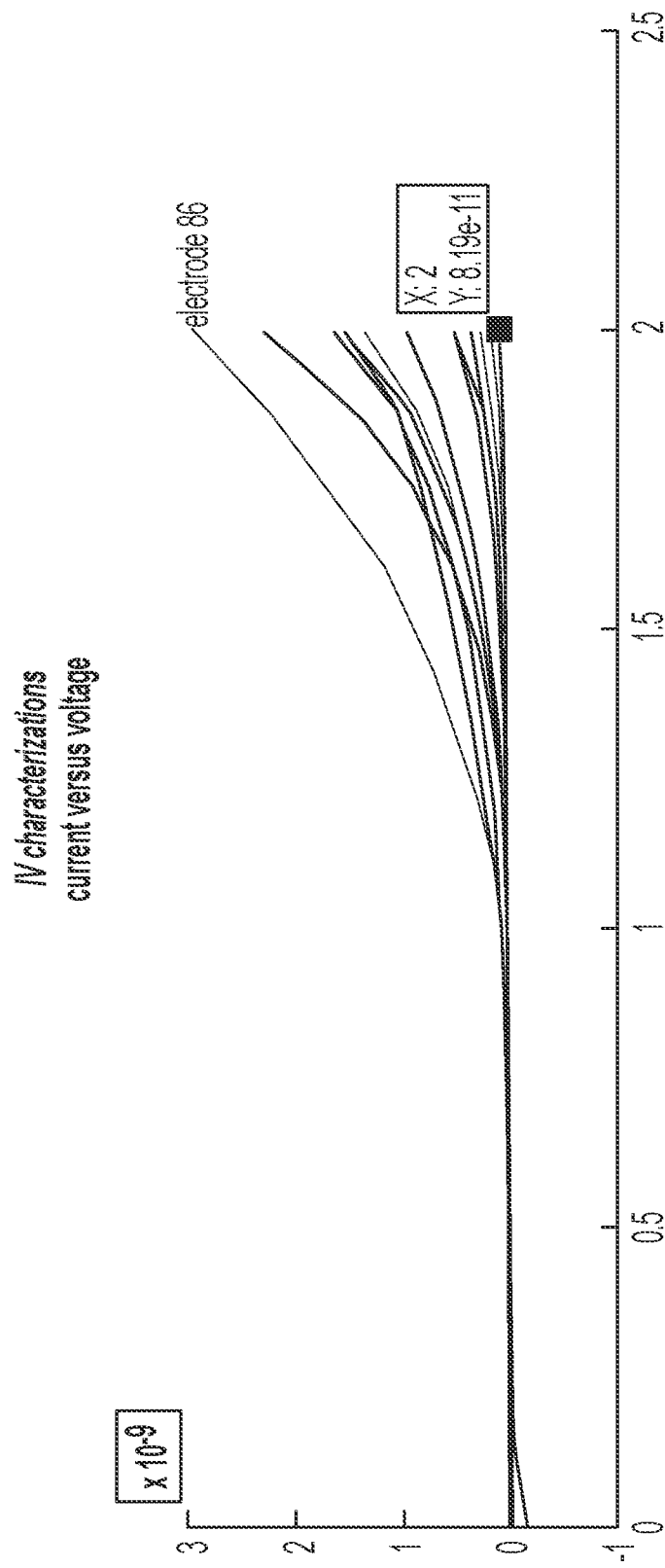
Figure 59B:
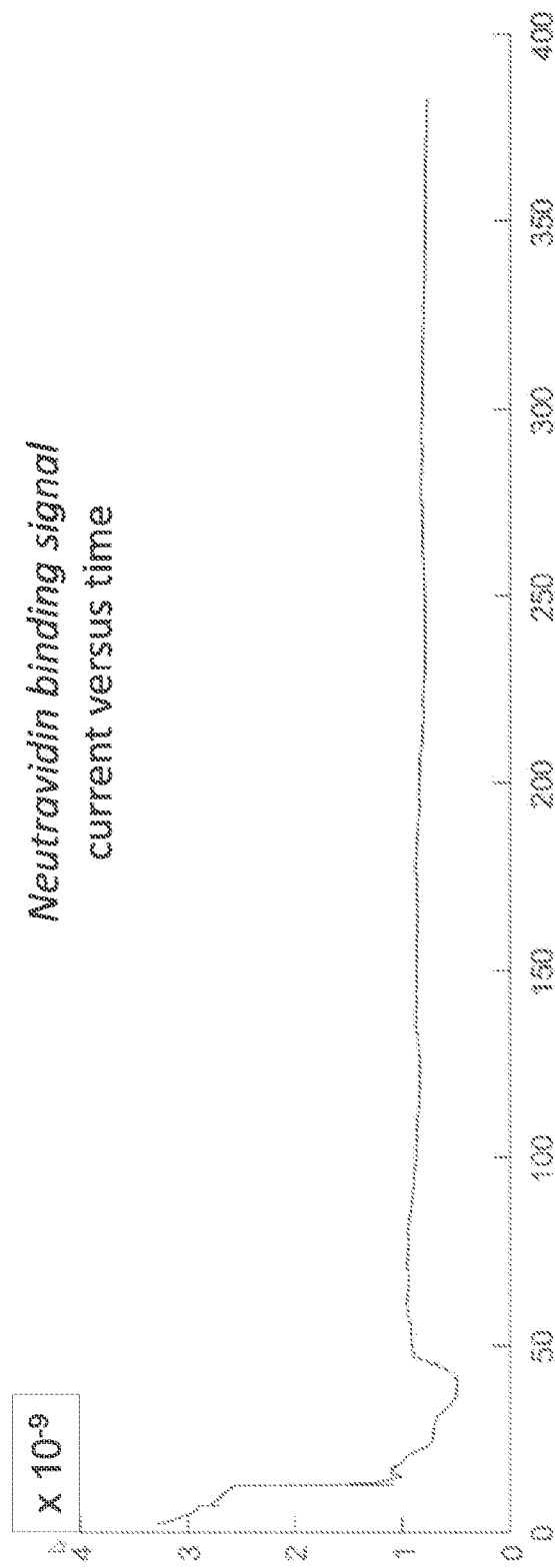
Figure 59D:
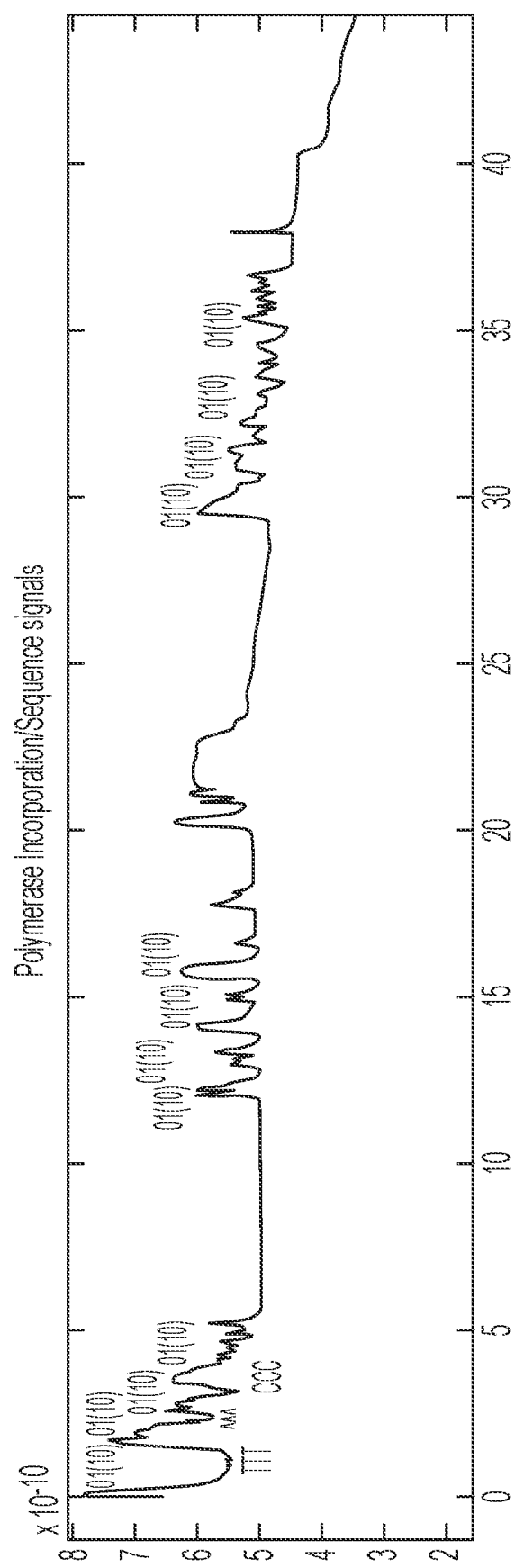

FIGS. 59A, 59B, 59C and 59D set forth data from a sequence sensing experiment using the alpha-helix peptide bridge. Referring now to FIG. 59A, the current-vs-voltage traces are for the electrodes on a test chip that have been incubated with the peptide bridge molecule for 1 hour in PBS buffer, at 1 µM peptide concentration, in order to attach the bridge to the gold contacts. The highest current trace, which achieves a 3 nano-amp current at 2 Volts applied source-drain, indicates an electrode having a bridge molecule bound in place. FIG. 59B is a current-vs-time trace showing the signature of the subsequent neutravidin binding to the bridge, at a time of approximately 10 to 50 seconds, when the bridged sensor is exposed to a neutravidin solution with applied source-drain voltage of 2 Volts. FIG. 59C is a current-vs-time trace showing the signature of the polymerase-maleimide-biotin binding the neutravidin-bridge complex, at the time of about 10 to 20 seconds, when the latter is exposed to a solution of the former. FIG. 59D depicts the resulting sequencing signals when the assembled sensor is provided with a solution containing a template DNA, with the sequence having a series of GT repeats: (10×GT) TTT (10×GT) AAA (10×GT) CCC (10×GT). The signal plot of FIG. 59D is annotated with one possible interpretation of these signals, where major spikes corresponding to the GT repeat tracts of the template, and overall three different template DNA molecules, engage with the sensor during the 45 seconds shown.

Figure 60:
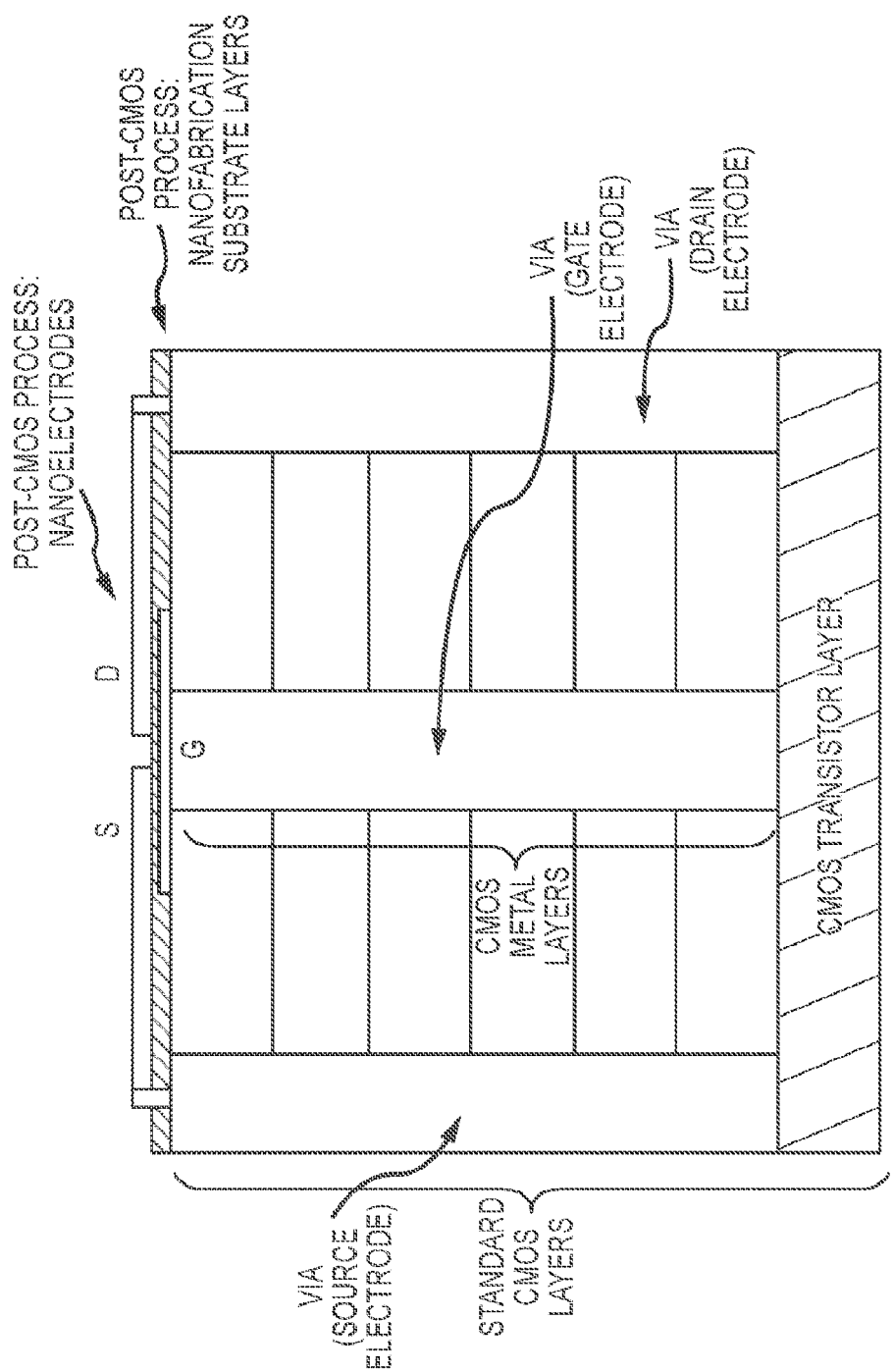
FIG. 60 illustrates an exemplary design for combining nano-electrodes interfaced to a CMOS device measurement pixel.

With reference now to FIG. 60, a design for combining nano-electrodes interfaced to a CMOS device measurement pixel is illustrated. In this embodiment, standard CMOS layers are indicated as consisting of the transistor layer at the bottom, used to implement the transistor circuit elements, along with a series of metal layers used for wiring together the circuit elements. As illustrated, a metal VIA is used to span these layers, from top to bottom, one providing a contact for the source nano-electrode (designated as "S"), another providing the connection for the drain nano-electrode (designated as "D"), and another for the gate nano-electrode (designated as "G"). These VIAs pass from the upper surface where these nanostructures are added during post-CMOS processing to the lower layers where the supporting pixel circuitry resides. These nano-electrodes are added in a post-processing step, which supports the nanoscale fabrication necessary. One preferred option is a different, high-resolution CMOS process, such as a 10 nm CMOS node, which could add these features, but they can alternatively be added by post-processing using other nano-lithography techniques, such as e-beam or nano-imprint lithography. In general the nano-electrodes will reside on a suitable substrate also added during the post-processing, which is both thin and flat on a nanometer scale, and which may provide a suitable surface for the remaining post-processing, and may include insulating layers as well as a metal gate electrode layer. The nanostructures are added on a planarized top layer from the standard CMOS process, which may be available by stopping the standard processing short of adding a typical final passivation layer to the top layer, or alternatively, by etching away such a passivation layer to expose the planarized surface.

Figure 61:
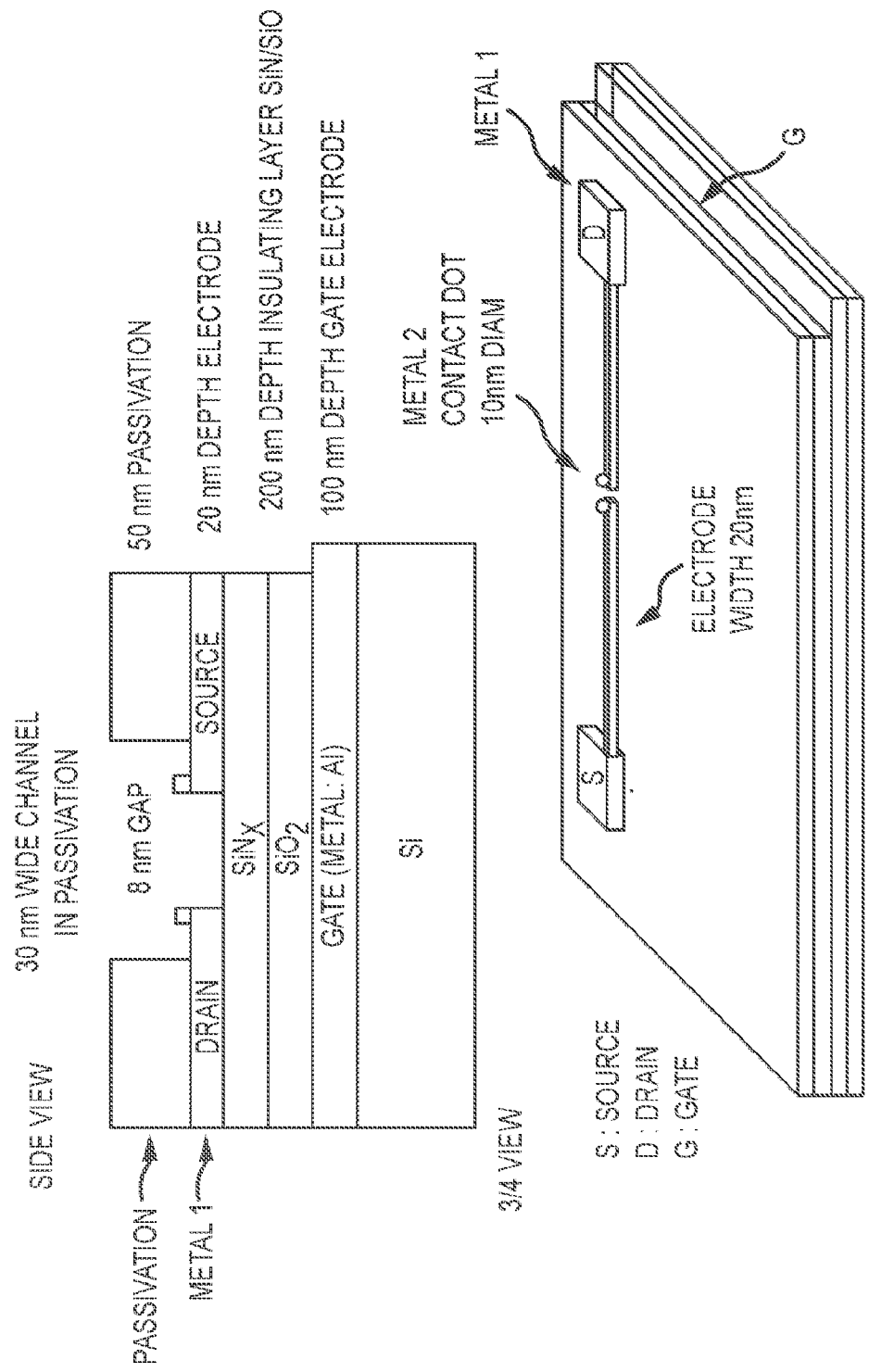
FIG. 61 depicts an example of the nanostructures added to the standard CMOS pixel device in post-processing steps.

Referring now to FIG. 61, an example of the nanostructures added to the standard CMOS pixel device in post-processing steps is depicted. The structures are added on top of the planarized top-metal layer from the CMOS process used to fabricate the pixel circuitry.

Figure 62:
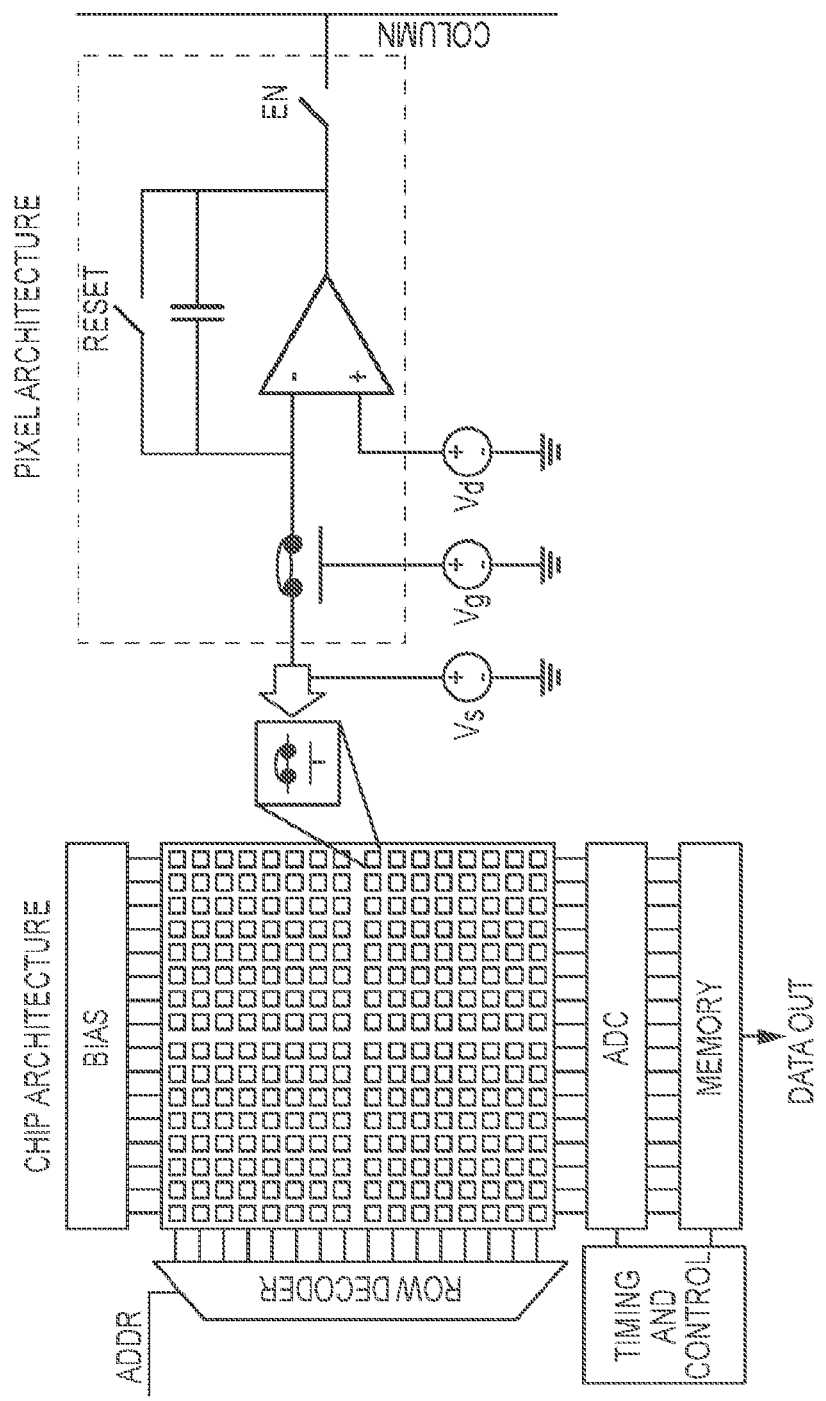
FIG. 62 shows an exemplary CMOS chip high-level architecture.

FIG. 62 shows an exemplary CMOS chip high-level architecture. The left portion of FIG. 62 illustrates high level architecture of the entire pixel array chip. The right portion of FIG. 62 illustrates high level architecture of the sensor pixel, with the molecular electronic nanosensor indicated. The chip contains a scalable array of sensor pixels, with associated power and control circuitry. In this embodiment, the sensor pixel contains an amplifier, a reset switch, and circuitry for supplying the source, gate and drain voltages, and for providing a readout of results.

Figure 63:
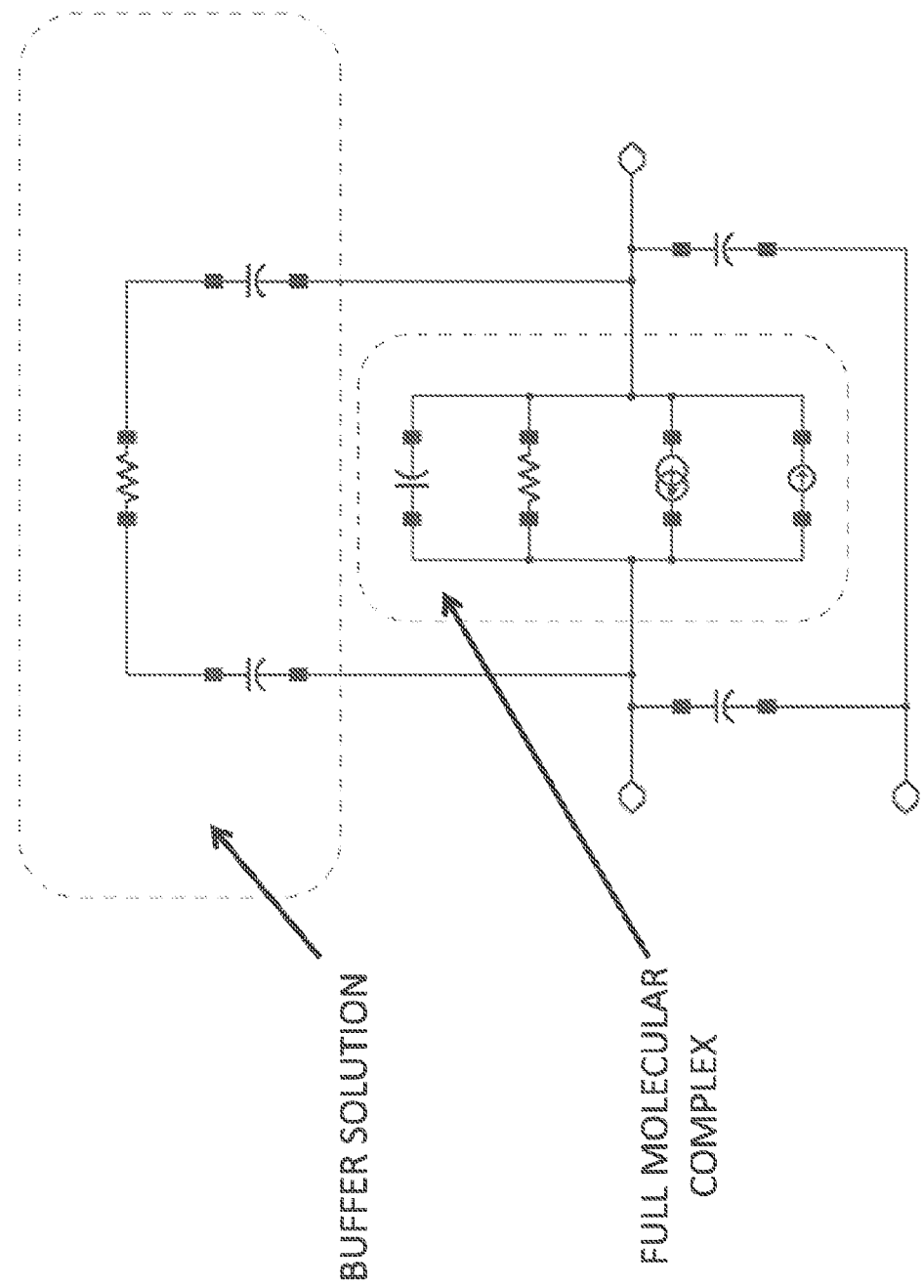
FIG. 63 illustrates an exemplary sensor electrical model.

With reference to FIG. 63, an exemplary sensor electrical model is illustrated. This figure shows a lumped electrical model of the sensor, including the regions surrounded the buffer solution and the molecular and nano-electrode structures. This system is approximated as shown for circuit modeling as a sub-circuit consisting of various resistors and capacitors. The molecular bridge presents a 2.5 Tera-Ohm resistance in this model, while the buffer solution has only a 1 kilo-Ohm resistance, but it is also isolated from the primary bridge connection via capacitive couplings including 100 aF (atto-Farad) capacitors, as shown.

Figure 64:
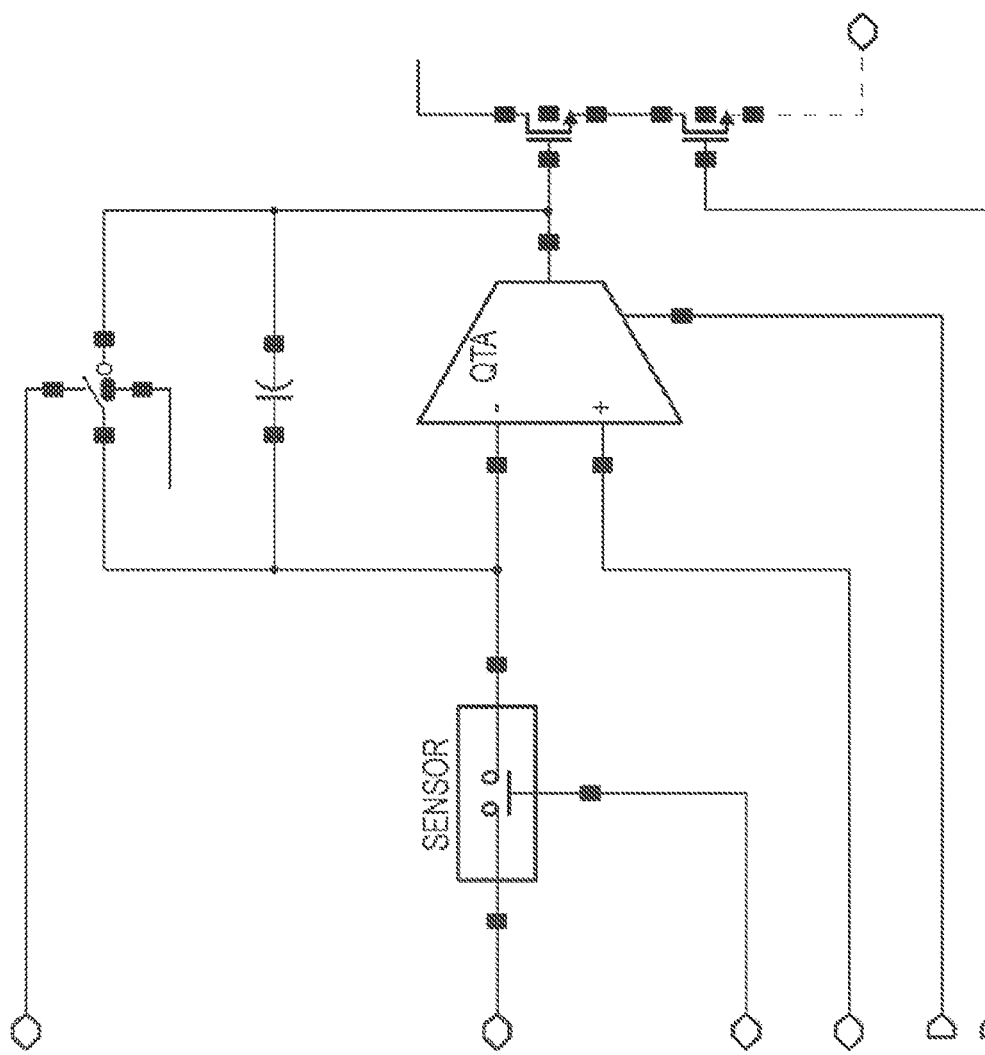
FIG. 64 illustrates an exemplary pixel circuit schematic.

Turning to FIG. 64, an exemplary pixel circuit schematic is provided. This is a detailed schematic of just one non-limiting embodiment of the pixel circuit. The sensor model is indicated as one sub-circuit of this exemplary circuit.

Figure 65:
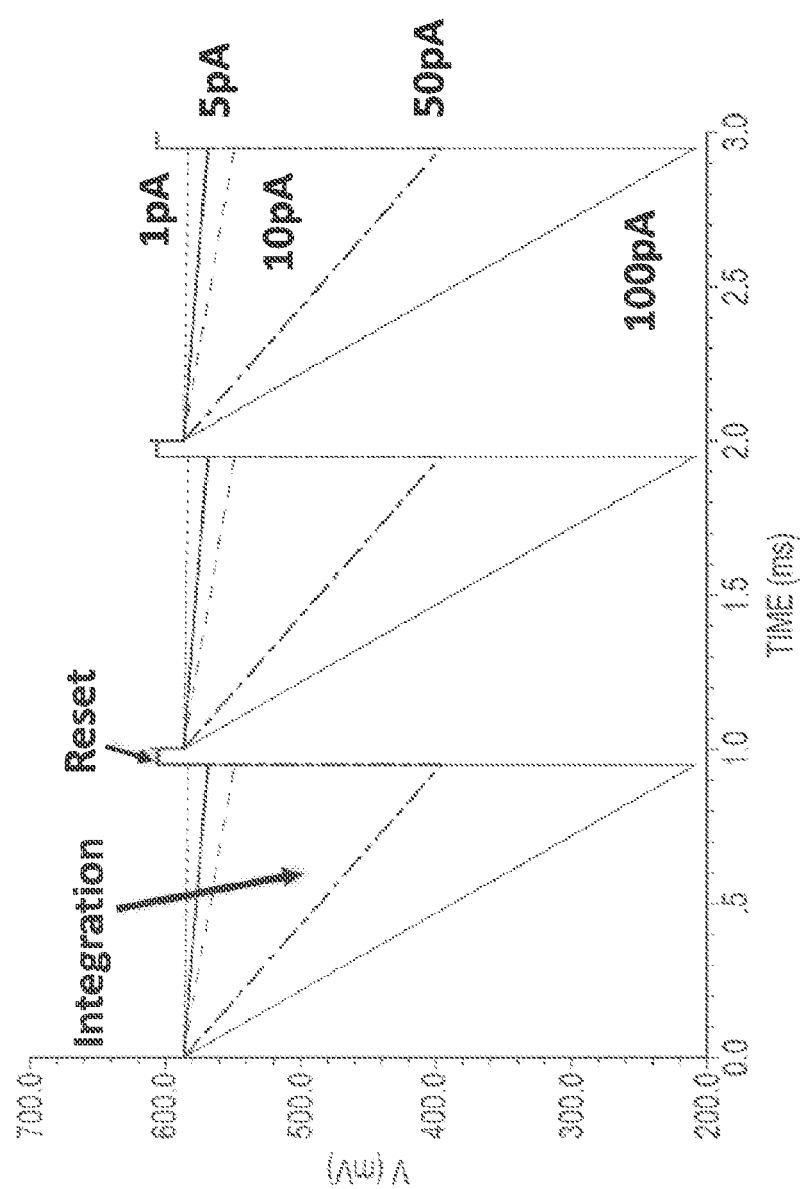
FIG. 65 sets forth the results of a pixel circuit simulation.

FIG. 65 sets forth the results of a pixel circuit simulation. These results are the detailed simulations of the pixel circuit performance. The simulation shows the amplifier output voltage (in millivolts) as a function of time (in milliseconds) for a sensor producing a current pulse of 1 ms duration, at different levels as indicated (1, 5, 10, 50 and 100 pA). For example and as shown, a 100 pA signal will produce a voltage spike of 400 mV in amplitude (moving from 200 mV to 600 mV=400 mV spike).

The table provided in FIG. 66 summarizes exemplary parameters for pixel switch performance.

Figure 67:
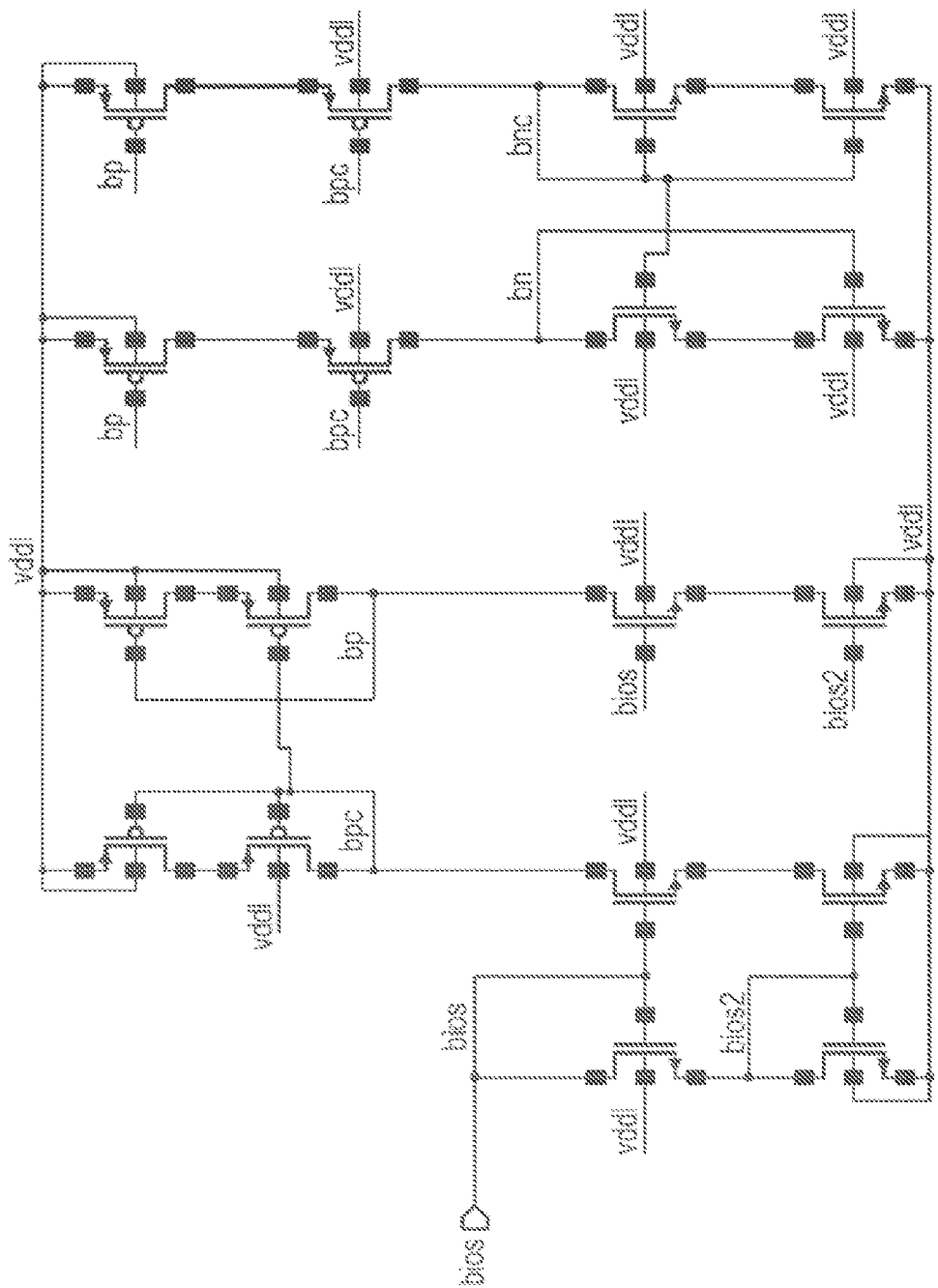
FIG. 67 illustrates an embodiment of a detailed circuit design for a pixel amplifier.

With reference now to FIG. 67, an embodiment of a detailed circuit design for a pixel amplifier is illustrated. This non-limiting example comprises a transistor-based pixel amplifier.

Figure 68:
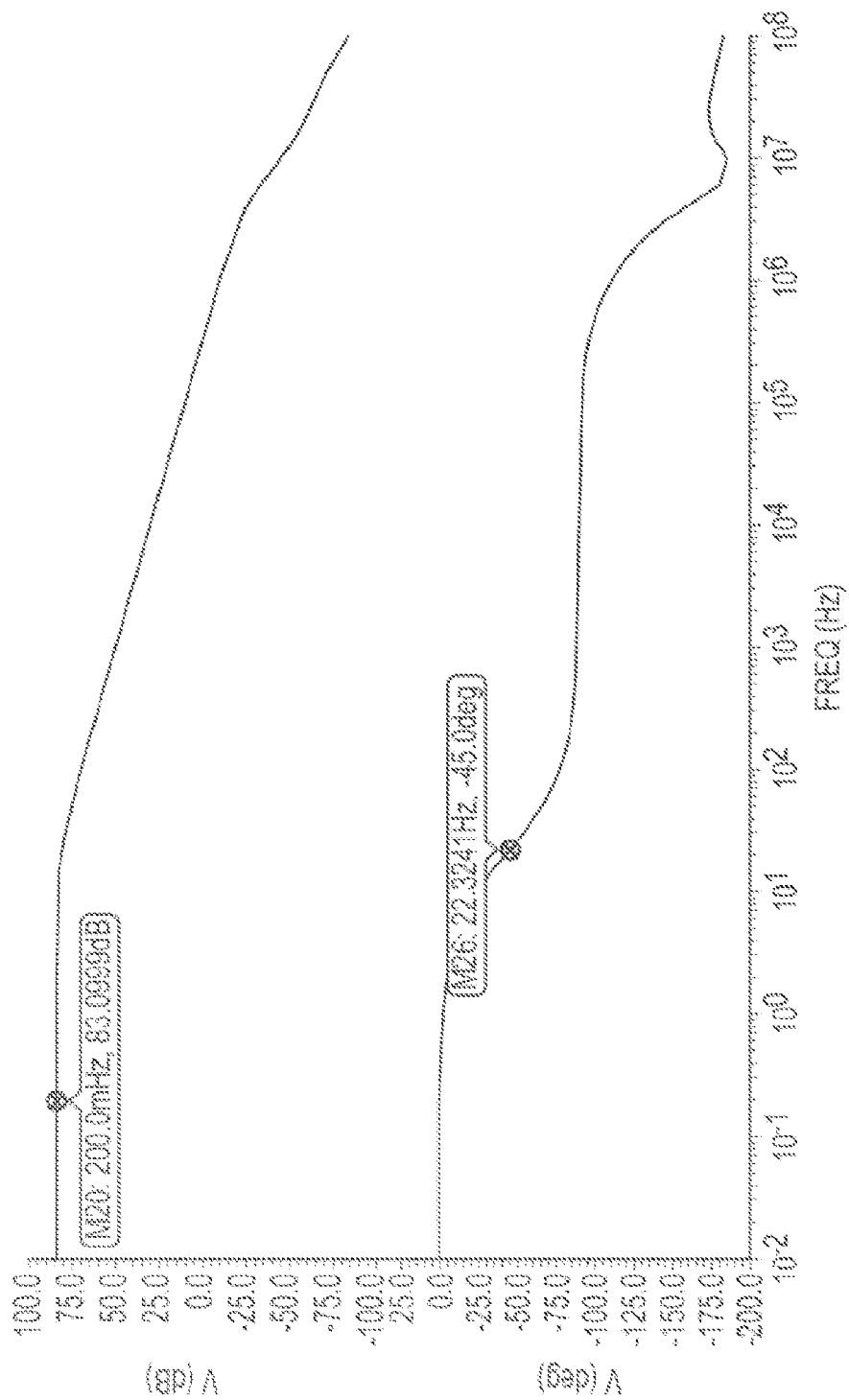
FIG. 68 provide simulation results for the amplifier frequency response.

FIG. 68 shows the actual simulation results for the amplifier frequency response. The plots show the results of detailed circuit simulation, for the gain of the amplifier as a function of measurement frequency, and the amplifier phase shift as a function of frequency. As seen in the plots, the amplifier begins to lose gain at a frequency of about 10 kHz.

FIG. 69 shows a table summarizing the parameters for pixel amplifier performance.

Figure 70:
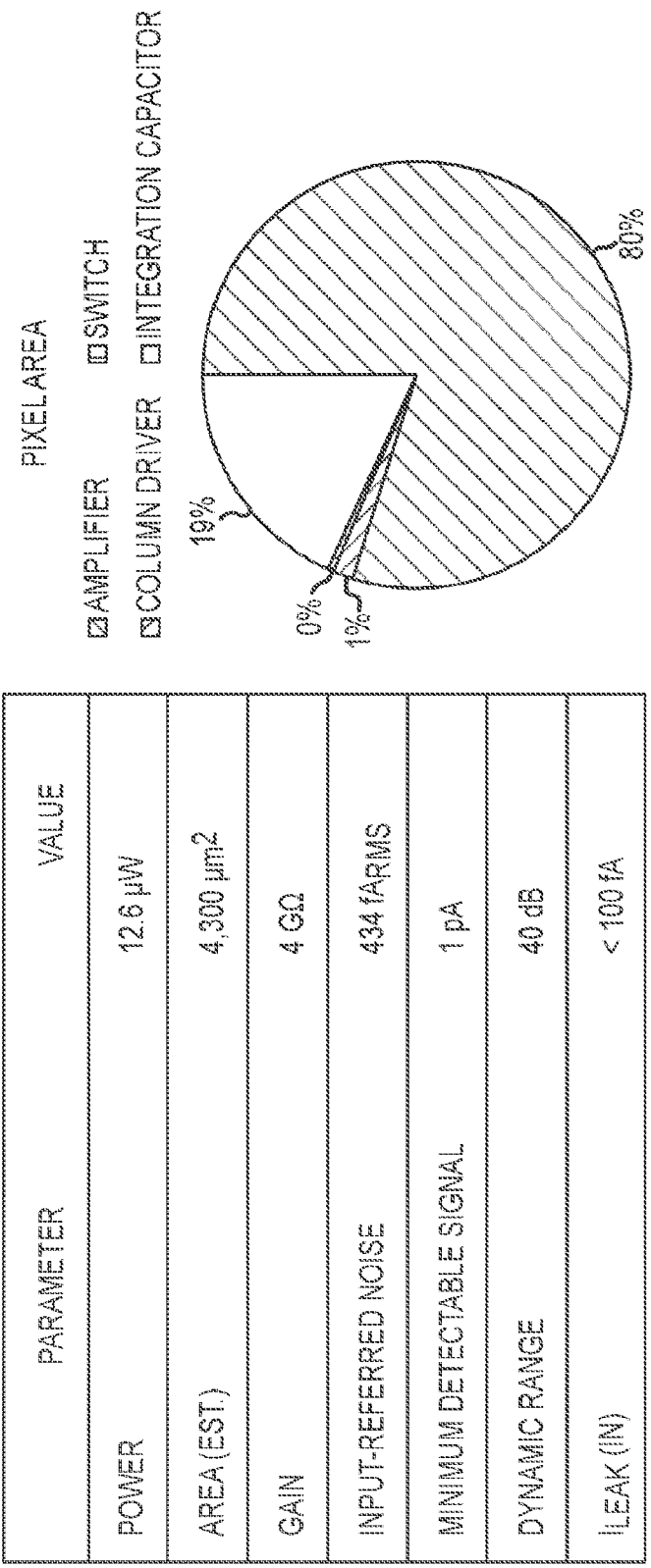
FIG. 70 summarizes the parameters for the sensor pixel, based on detailed circuit simulations along with a pie-chart showing a layout area budget for different elements of the pixel.

FIG. 70 summarizes the parameters for the sensor pixel, based on detailed circuit simulations. At the left of FIG. 70 are the performance parameters set forth in a table. The pie-chart at the right of FIG. 70 shows a layout area budget for different elements of the pixel. As indicated, 80% of the pixel layout area is dedicated to the amplifier.

Figure 71:
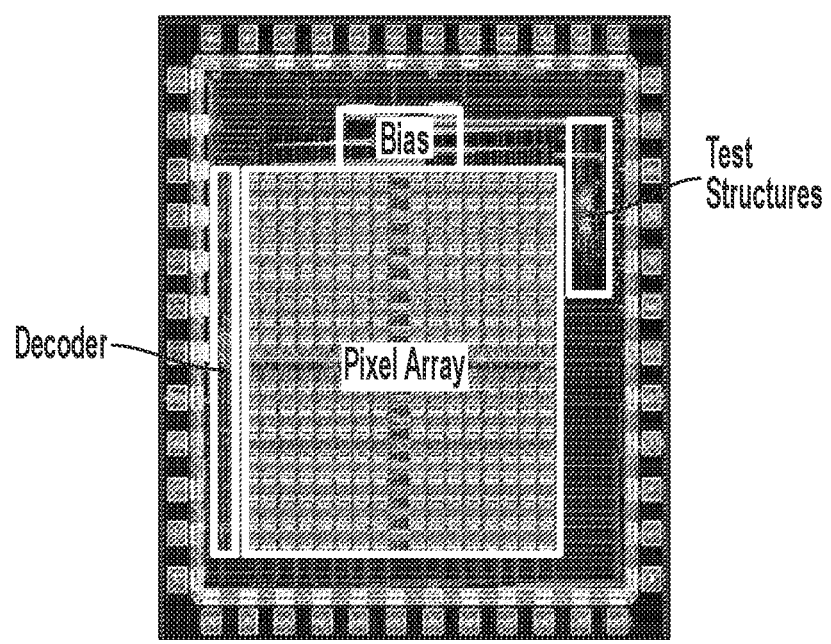
FIG. 71 is an image of an embodiment of an annotated complete chip design.

With reference now to FIG. 71, an image of an embodiment of an annotated complete chip design is provided. This image is of a complete design of the CMOS chip, which high level annotations of the different functional elements of the chip. The image is produced from a complete GDS (Geometric Data Stream) file, which specifies the complete, detailed layout of the chip, for all layers. This specific design is for an Electronics Industry Standard 180 nm CMOS node, with 6 metal layers.

Figure 72:
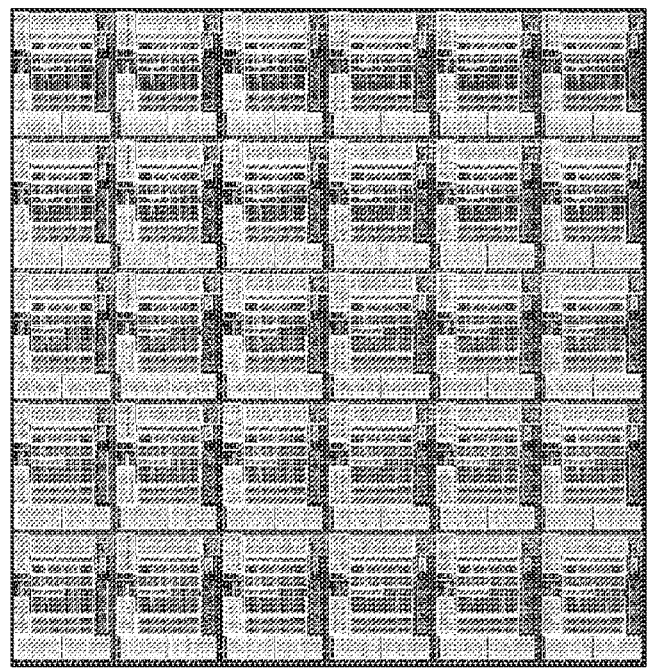
FIG. 72 is an exemplary pixel array design seen in close-up image of the detailed GDS design file for a 5×5 portion of the pixel array.

FIG. 72 is an exemplary pixel array design seen in close-up image of the detailed GDS design file for a 5×5 portion of the pixel array.

Figure 73:
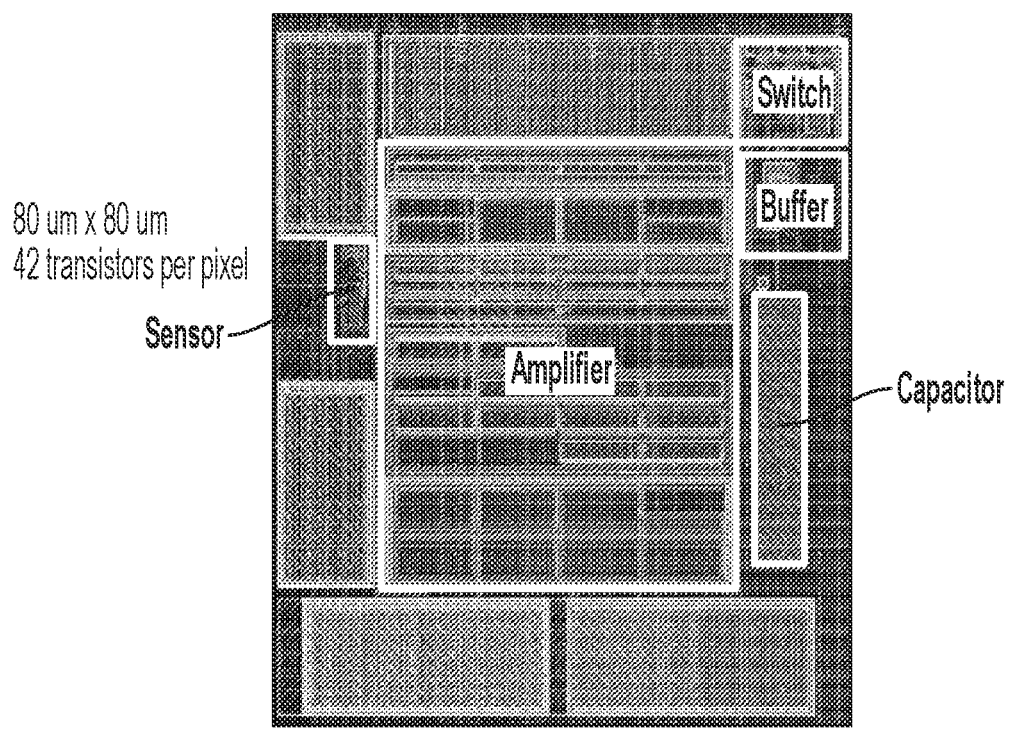
FIG. 73 sets forth an exemplary annotated complete pixel design.

FIG. 73 is an annotated complete pixel design. The image is a final pixel design taken from the GDS file, annotated to indicate the location of the amplifier circuits, the switch, and other elements. The molecular electronic nano-sensor was added by post-processing in the indicated area labeled "Sensor". The pixel is 80 micron×80 micron in size, and contains 42 total transistors.

Figure 74:
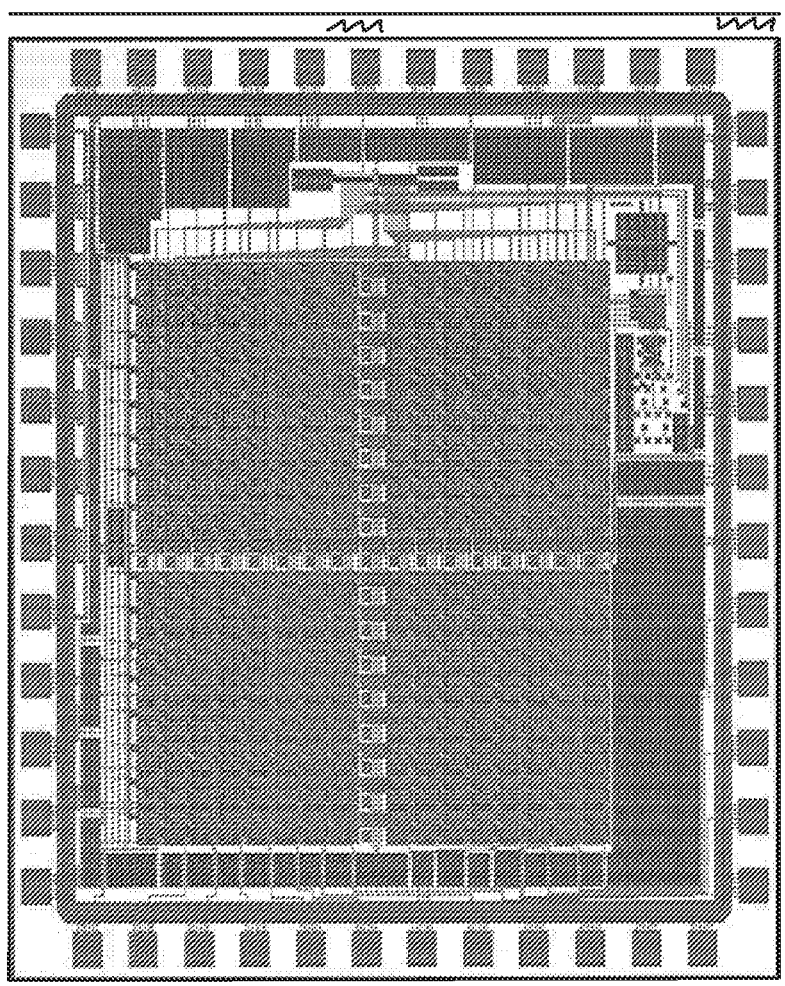
FIG. 74 is a white-light microscope image of the finished chip, after fabrication.

FIG. 74 is a white-light microscope image of the finished chip, after fabrication, comprising an example of a fabricated device.

Figures 75A, 75B:
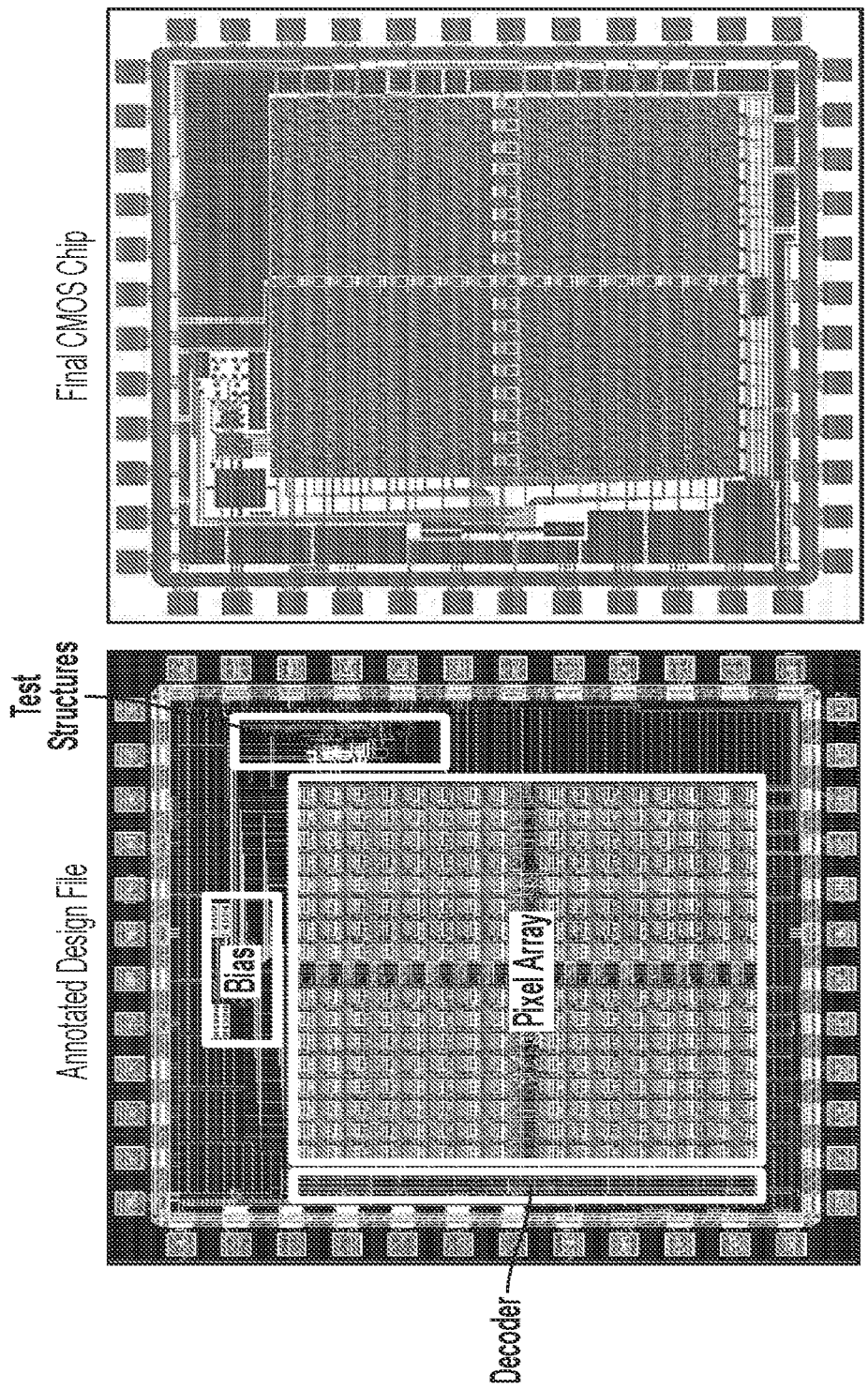
FIGS. 75A and 75B provide a comparison of the layout file and finished chip.

FIGS. 75A and 75B provide a comparison of the layout file and finished chip. FIG. 75A is the annotated image of the rendered layout (GDS) file for the chip design. FIG. 75B is an image of the finished chip produced with the TSMC 180 nm CMOS process, with no passivation layer.

Figure 76:
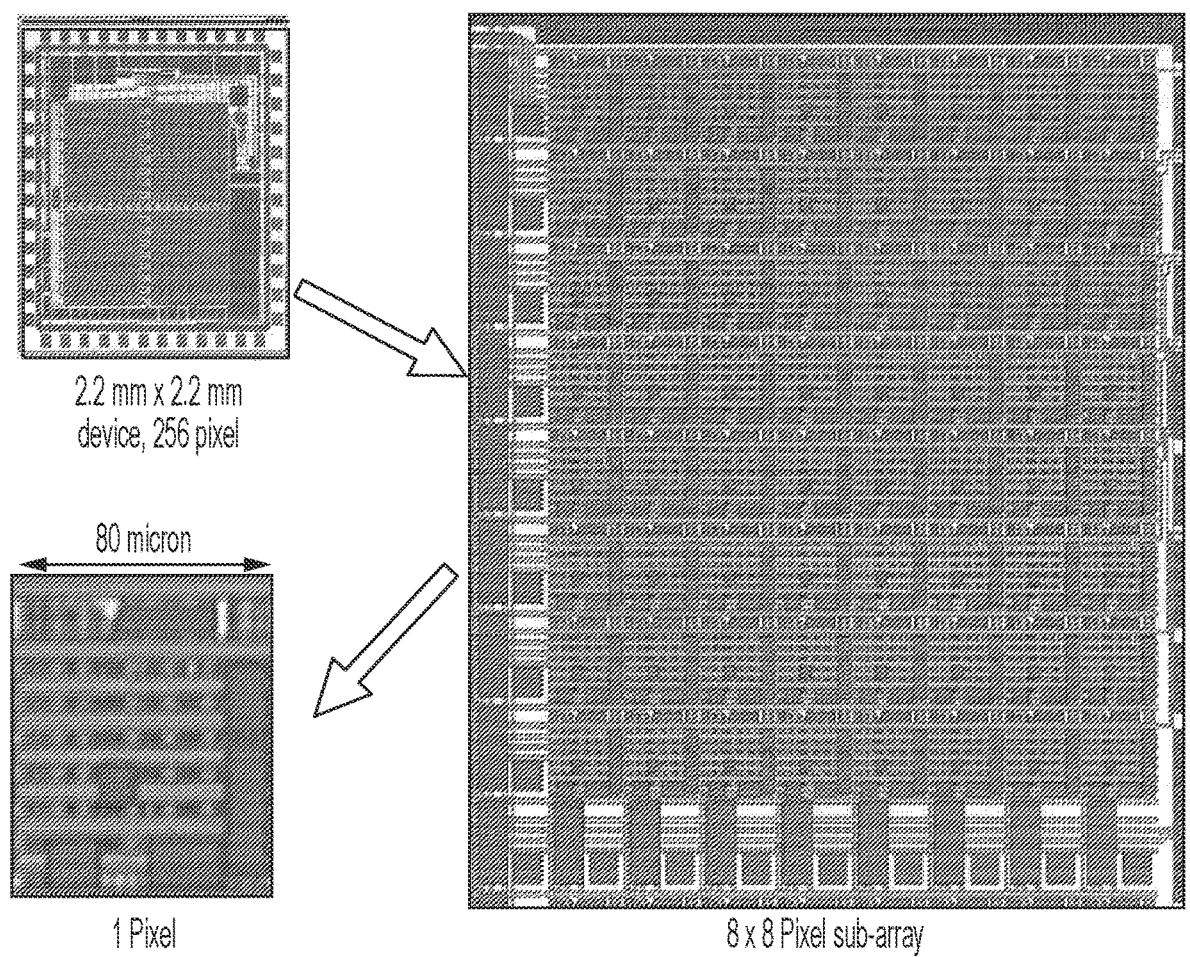
FIG. 76 provides a collection of pixel array images.

FIG. 76 provides a collection of pixel array images. The figure shows a series of close-up images of the CMOS chip, showing the pixel array and single pixel. Images are from a white-light microscope image of un-passivated CMOS chip.

Figures 77A, 77B:
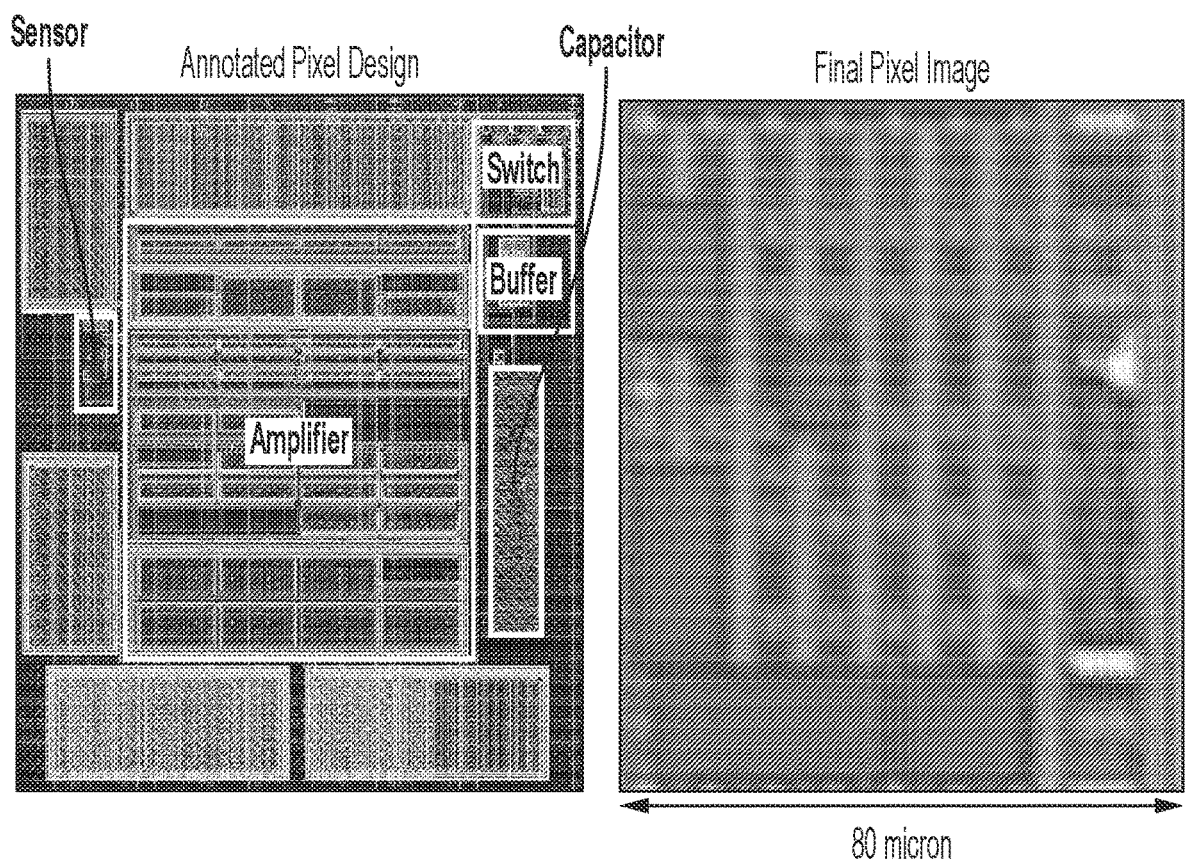
FIGS. 77A and 77B provide comparison of the layout file and finished chip pixel.

FIGS. 77A and 77B provide comparison of the layout file and finished chip pixel. FIG. 77A is an annotated image of the rendered layout (GDS) file for a single pixel, whereas FIG. 77B is an image of a finished chip single pixel, produced with the TSMC 180 nm CMOS process, with no passivation layer.

Figure 78A:
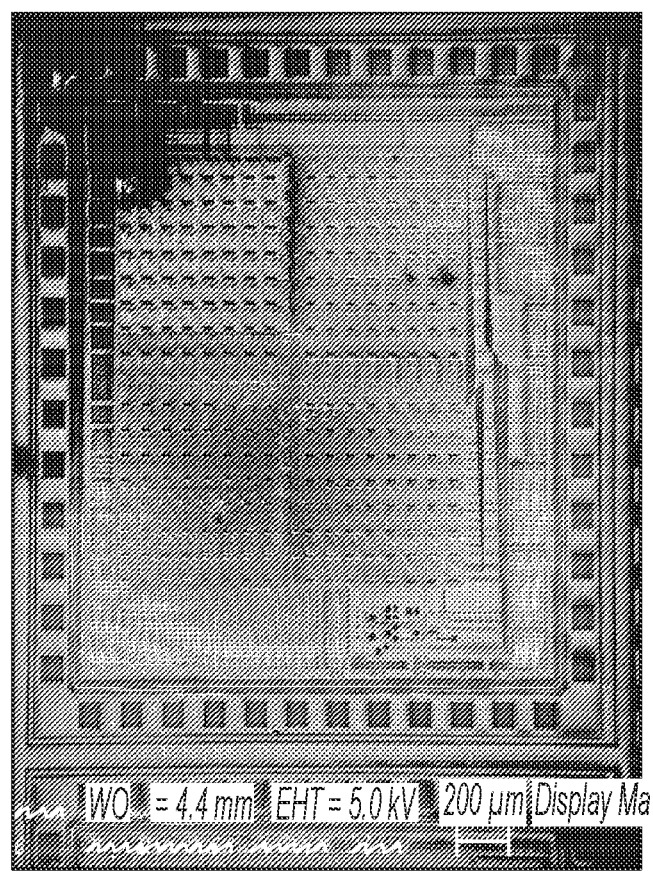

FIGS. 78A and 78B are electron microscope images of a finished CMOS chip and pixel. FIG. 78A is a Scanning Electron Microscope (SEM) image of the CMOS chip, with no top passivation layer, and exposed planarized metal 6 layer. FIG. 78B is an SEM image of a single pixel showing the surface structure details. These figures show the exposed VIAs where the nano-electrodes for source, drain and gate are to be added in post-CMOS nanofabrication processing steps.

Figure 79:
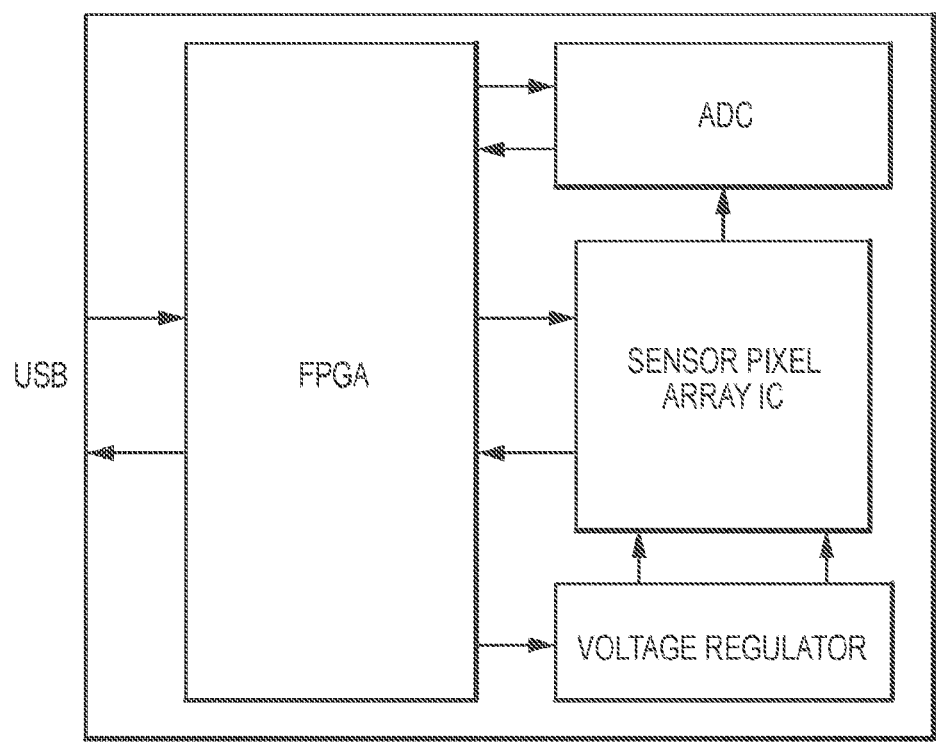
FIG. 79 illustrates an exemplary schematic design of a motherboard for the sensor chip.

Lastly, FIG. 79 illustrates an exemplary schematic design of a motherboard for the sensor chip. This figure illustrates the connection of the chip to an FPGA, ADC and voltage regulator to produce a motherboard for USB connection to a data acquisition computer for collection and analysis of signals from sensor chip pixels.

We claim:

1. A molecular electronics sensor array chip comprising:
   (a) an integrated circuit semiconductor chip; and
   (b) a plurality of molecular electronic sensor devices disposed thereon, each sensor device comprising:
      (i) a pair of nanoscale source and drain electrodes separated by a nanogap,
      (ii) a gate electrode;
      (iii) a peptide alpha-helix bridge molecule comprising an amino acid sequence according to SEQ ID NO:1 spanning the nanogap and connecting the source and drain electrodes, wherein the peptide alpha-helix comprises a coupling group having a central lysine modified to include biotin on a linker for binding of a neutravidin protein; and
      (iv) a polymerase enzyme coupled to the central lysine of the peptide alpha-helix bridge molecule by a linker conjugated to the polymerase and connected to the coupling group of the bridge molecule by a biotin-neutravidin binding reaction;
   wherein the sensor devices are organized into an array of sensor pixels.

2. The molecular electronics sensor array chip of claim 1, wherein the linker conjugated to the polymerase enzyme comprises a biotin-maleimide linker conjugated to a surface cysteine on the polymerase.

3. The molecular electronics sensor array chip of claim 1, wherein the chip comprises at least 100 sensor devices.

4. The molecular electronics sensor array chip of claim 1, wherein device voltages are used to monitor and/or facilitate molecular self-assembly of each bridge molecule to each source and drain electrode pair and/or a molecular self-assembly of each probe molecule to each bridge molecule, including the use of a voltage-directed reset to restore the sensor to pre-molecular state as needed for successive trials.

5. The molecular electronics sensor array chip of claim 1, wherein the source and drain electrodes comprise gold contacts on electrodes comprising chromium.

6. The molecular electronics sensor array chip of claim 5, wherein the peptide alpha-helix bridge molecule comprising SEQ ID NO:1 has cysteine amino acids at the terminal for thiol-gold coupling to the gold contacts on the electrodes.

7. The molecular electronics sensor array chip of claim 1, wherein the polymerase enzyme comprises a DNA polymerase.

8. The molecular electronics sensor array chip of claim 1, wherein the polymerase enzyme comprises a *E. Coli* Klenow fragment of a DNA polymerase.

9. The molecular electronics sensor array chip of claim 1, wherein each sensor pixel further comprises a readout capacitor or readout resistor connected to each sensor device.

10. The molecular electronics sensor array chip of claim 9, wherein each sensor pixel further comprises a transistor-based output switch.

11. The molecular electronics sensor array chip of claim 10, wherein each sensor pixel further comprises a transistor-based reset switch.

12. The molecular electronics sensor array chip of claim 11, wherein each sensor pixel further comprises a row select line and a column readout line connected thereto, and the array of sensor pixels comprises an integrated row select column-readout array architecture, whereby the row select lines energize the sensor pixels.

13. The molecular electronics sensor array chip of claim 12, wherein the row select lines control the output switches.

14. The molecular electronics sensor array chip of claim 13, wherein each sensor pixel further comprises a row-reset line and a column-reset line for controlling each reset switch.

15. The molecular electronics sensor array chip of claim 14, wherein each reset switch is controlled by a combination of the row select line and the column-reset line, such as to provide direct control over the reset of each sensor pixel.

16. A process for measuring signals of incorporation for a multiplicity of replicate primed DNA fragments applied to a chip, said process comprising:
provideing at least one molecular electronics sensor array chip of claim 1;
applying a mixture of deoxynucleotide triphosphates and specific base terminators to the molecular electronics sensor array chip; and
measuring the specific base locations along the DNA fragments.

17. The process of claim 16, wherein at least four (4) molecular electronics sensor array chips are utilized, one for each base reaction.

18. The process of claim 16, used to perform a digital fragment length assay.

19. A chip-based analyzer system for sample analysis, said system comprising:
at least one molecular electronics sensor array chip of claim 1;
a motherboard in which the at least one molecular electronics sensor array chip is integrated;
a liquid handling system configured to control introduction of at least the sample to the plurality of molecular electronic sensor devices;
at least one signal processor; and
a CPU.

20. The chip-based analyzer system of claim 19, wherein the chip-based analyzer is integrated into a multi-modality bio-analyzer, thereby producing a multi-modality integrated report from the sample.

21. The chip-based analyzer system of claim 19, configured as a hand-held, wearable, or implantable system.

22. A process of analyzing a bio-sample, said method rising the steps of:
providing the chip-based analyzer system of claim 19;
collecting the bio-sample from a subject;
processing the bio-sample through the chip-based analyzer system to obtain data relevant to an analysis of the bio-sample; and
transferring the data to a storage server or cloud.

23. The process of claim 22, wherein the bio-sample is collected from a subject in conjunction with information pertaining to the subject, and analyzed to produce an integrated report comprising both the information.

24. A molecular electronics sensor array chip comprising:
a) an integrated circuit semiconductor chip; and
b) a plurality of molecular electronic sensor devices disposed thereon, each sensor device comprising:
(i) a pair of nanoscale source and drain electrodes separated by a nanogap,
(ii) a gate electrode;
(iii) a peptide alpha-helix bridge molecule spanning the nanogap and connecting the source and drain electrodes, wherein the peptide alpha-helix comprises a coupling group having an amino acid modified to include biotin on a linker to support binding of a neutravidin protein; and
(iv) a polymerase coupled to an amino acid of the peptide alpha-helix bridge molecule by a linker conjugated to a surface amino acid on the polymerase and connected to the coupling group of the bridge molecule by a biotin-neutravidin binding reaction;
wherein the sensor devices are organized into an array of sensor pixels.

25. The molecular electronics sensor array chip of claim 24, wherein the peptide alpha-helix bridge molecule is approximately 9 nm in length.

* * * * *